(12) United States Patent
Tolkowsky et al.

(10) Patent No.: US 11,064,964 B2
(45) Date of Patent: Jul. 20, 2021

(54) DETERMINING A CHARACTERISTIC OF A LUMEN BY MEASURING VELOCITY OF A CONTRAST AGENT

(71) Applicant: SYNC-RX, LTD., Netanya (IL)

(72) Inventors: David Tolkowsky, Tel Aviv (IL); Alexander Steinberg, Ra'anana (IL); Eldad Klaiman, Herzlia (IL); Ran Cohen, Petah Tikva (IL)

(73) Assignee: SYNC-RX, LTD, Netanya (IL)

( * ) Notice: Subject to any disclaimer, the term of this patent is extended or adjusted under 35 U.S.C. 154(b) by 70 days.

(21) Appl. No.: 14/142,082

(22) Filed: Dec. 27, 2013

(65) Prior Publication Data
US 2014/0121513 A1    May 1, 2014

Related U.S. Application Data

(63) Continuation of application No. PCT/IL2013/050549, filed on Jun. 26, 2013, and a
(Continued)

(51) Int. Cl.
*A61B 6/00* (2006.01)
*G06K 9/36* (2006.01)
(Continued)

(52) U.S. Cl.
CPC ............ *A61B 6/5217* (2013.01); *A61B 5/021* (2013.01); *A61B 5/026* (2013.01);
(Continued)

(58) Field of Classification Search
None
See application file for complete search history.

(56) References Cited

U.S. PATENT DOCUMENTS 3,871,360 A    3/1975    Van Horn et al.
3,954,098 A    5/1976    Dick et al.
(Continued)

FOREIGN PATENT DOCUMENTS

EP    2312531        4/2011
EP    2 570 079 A1    3/2013
(Continued)

OTHER PUBLICATIONS

"Sen et al.," Development and validation of a new adenosine-independent index of stenosis severity from coronary wave-intensity analysis: results of ADVISE study, J. Am Coll Cardiol. vol. 59, No. 15 pp. 1392-1402 (online publication Dec. 7, 2011).*
(Continued)

*Primary Examiner* — Patricia J Park

(57) ABSTRACT

Apparatus and methods are described for use with a plurality of angiographic image frames of a moving lumen of a subject, including aligning the image frames with each other. Using the aligned image frames, a time it takes a contrast agent to travel a known distance through the lumen is determined. At least partially in response thereto, a characteristic of the lumen is determined, and, in response to the determined characteristic, an output is generated on a display. Other applications are also described.

21 Claims, 8 Drawing Sheets

Related U.S. Application Data continuation-in-part of application No. 12/075,244, filed on Mar. 10, 2008, now abandoned.

(60) Provisional application No. 61/690,393, filed on Jun. 26, 2012, provisional application No. 61/741,105, filed on Jul. 12, 2012, provisional application No. 61/692,280, filed on Aug. 23, 2012, provisional application No. 61/704,570, filed on Sep. 24, 2012, provisional application No. 60/906,091, filed on Mar. 8, 2007, provisional application No. 60/924,609, filed on May 22, 2007, provisional application No. 60/929,165, filed on Jun. 15, 2007, provisional application No. 60/935,914, filed on Sep. 6, 2007, provisional application No. 60/996,746, filed on Dec. 4, 2007.

(51) Int. Cl.
  *G06K 9/62* (2006.01)
  *G06K 9/46* (2006.01)
  *G06T 7/20* (2017.01)
  *A61B 5/02* (2006.01)
  *A61B 6/12* (2006.01)
  *A61B 5/021* (2006.01)
  *A61B 5/026* (2006.01)
  *A61B 17/22* (2006.01)
  *A61B 17/00* (2006.01)
  *A61B 8/08* (2006.01)
  *A61B 5/0215* (2006.01)
  *A61B 8/00* (2006.01)
  *A61B 5/00* (2006.01)
  *A61F 2/958* (2013.01)

(52) U.S. Cl.
  CPC ............ *A61B 5/02007* (2013.01); *A61B 6/12* (2013.01); *A61B 6/481* (2013.01); *A61B 6/486* (2013.01); *A61B 6/504* (2013.01); *A61B 6/507* (2013.01); *A61B 6/541* (2013.01); *G06T 7/20* (2013.01); *A61B 5/0215* (2013.01); *A61B 5/7264* (2013.01); *A61B 5/7289* (2013.01); *A61B 6/503* (2013.01); *A61B 8/0883* (2013.01); *A61B 8/0891* (2013.01); *A61B 8/543* (2013.01); *A61B 2017/00252* (2013.01); *A61B 2017/00694* (2013.01); *A61B 2017/00703* (2013.01); *A61B 2017/22044* (2013.01); *A61B 2017/22094* (2013.01); *A61B 2576/00* (2013.01); *A61F 2/958* (2013.01)

(56) References Cited

U.S. PATENT DOCUMENTS

| | | |
|---|---|---|
| 4,016,871 A | 4/1977 | Schiff |
| 4,031,884 A | 6/1977 | Henzel |
| 4,245,647 A | 1/1981 | Randall |
| 4,270,143 A | 5/1981 | Morris |
| 4,316,218 A | 2/1982 | Gay |
| 4,382,184 A | 5/1983 | Wernikoff |
| 4,545,390 A | 10/1985 | Leary |
| 4,709,385 A | 11/1987 | Pfeiler |
| 4,712,560 A | 12/1987 | Schaefer et al. |
| 4,723,938 A | 2/1988 | Goodin et al. |
| 4,741,328 A | 5/1988 | Gabbay |
| 4,758,223 A | 7/1988 | Rydell |
| 4,770,184 A * | 9/1988 | Greene et al. ............... 600/454 |
| 4,849,906 A | 7/1989 | Chodos et al. |
| 4,865,043 A | 9/1989 | Shimoni |
| 4,878,115 A | 10/1989 | Elion |
| 4,920,413 A | 4/1990 | Nakamura |
| 4,991,589 A | 2/1991 | Hongo et al. |
| 4,994,965 A | 2/1991 | Crawford et al. |
| 5,020,516 A | 6/1991 | Biondi |
| 5,054,045 A | 10/1991 | Whiting et al. |
| 5,054,492 A | 10/1991 | Scribner |
| 5,056,524 A | 10/1991 | Oe |
| 5,062,056 A | 10/1991 | Lo et al. |
| 5,150,292 A * | 9/1992 | Hoffmann ............... A61B 6/481 |
| | | 250/303 |
| 5,176,619 A | 1/1993 | Segalowitz |
| 5,177,796 A | 1/1993 | Feig et al. |
| 5,293,574 A | 3/1994 | Roehm et al. |
| 5,295,486 A | 3/1994 | Wollschlager et al. |
| 5,330,496 A | 7/1994 | Alferness |
| 5,357,550 A | 10/1994 | Asahina et al. |
| 5,429,144 A | 7/1995 | Wilk |
| 5,457,728 A | 10/1995 | Whiting et al. |
| 5,457,754 A | 10/1995 | Han et al. |
| 5,486,192 A | 1/1996 | Walinsky et al. |
| 5,537,490 A | 7/1996 | Yukawa |
| 5,538,494 A | 7/1996 | Matsuda |
| 5,577,502 A | 11/1996 | Darrow et al. |
| 5,586,201 A | 12/1996 | Whiting et al. |
| 5,596,990 A | 1/1997 | Yock |
| 5,613,492 A | 3/1997 | Feinberg |
| 5,619,995 A | 4/1997 | Lobodzinski |
| 5,630,414 A | 5/1997 | Horbaschek |
| 5,674,217 A | 10/1997 | Walhstrom et al. |
| 5,724,977 A | 3/1998 | Yock |
| 5,764,723 A | 6/1998 | Weinberger |
| 5,766,208 A | 6/1998 | McEwan |
| 5,792,157 A | 8/1998 | Mische et al. |
| 5,807,327 A | 9/1998 | Green et al. |
| 5,809,105 A | 9/1998 | Roehm et al. |
| 5,822,391 A | 10/1998 | Whiting et al. |
| 5,830,222 A | 11/1998 | Makower |
| 5,879,305 A | 3/1999 | Yock |
| 5,885,218 A | 3/1999 | Teo |
| 5,885,244 A | 3/1999 | Leone et al. |
| 5,916,194 A | 6/1999 | Jacobsen et al. |
| 5,921,934 A | 7/1999 | Teo |
| 5,971,976 A | 10/1999 | Wang et al. |
| 6,088,488 A | 7/2000 | Hardy et al. |
| 6,095,976 A | 8/2000 | Nachtomy |
| 6,120,455 A | 9/2000 | Teo |
| 6,120,523 A | 9/2000 | Crocker et al. |
| 6,126,608 A | 10/2000 | Kemme et al. |
| 6,148,095 A | 11/2000 | Prause et al. |
| 6,152,878 A | 11/2000 | Nachtomy |
| 6,195,445 B1 | 2/2001 | Dubuisson-Jolly et al. |
| 6,233,478 B1 | 5/2001 | Liu |
| 6,246,898 B1 | 6/2001 | Vesely et al. |
| 6,254,541 B1 | 7/2001 | Teo |
| 6,267,727 B1 | 7/2001 | Teo |
| 6,278,767 B1 | 8/2001 | Hsieh |
| 6,331,181 B1 | 12/2001 | Tierney et al. |
| 6,370,417 B1 | 4/2002 | Horbaschek et al. |
| 6,377,011 B1 | 4/2002 | Ben-Ur |
| 6,442,415 B1 | 8/2002 | Bis et al. |
| 6,454,715 B2 | 9/2002 | Teo |
| 6,454,776 B1 | 9/2002 | Tajima et al. |
| 6,473,635 B1 | 10/2002 | Rasche |
| 6,491,636 B2 | 12/2002 | Chenal |
| 6,493,575 B1 | 12/2002 | Kesten et al. |
| 6,496,716 B1 | 12/2002 | Langer et al. |
| 6,532,380 B1 | 3/2003 | Close et al. |
| 6,538,634 B1 | 3/2003 | Chui et al. |
| 6,546,271 B1 | 4/2003 | Reisfeld |
| 6,576,007 B2 | 6/2003 | Dehdashtian et al. |
| 6,589,176 B2 | 7/2003 | Jago |
| 6,616,596 B1 | 9/2003 | Milbocker |
| 6,643,533 B2 | 11/2003 | Knoplioch |
| 6,659,953 B1 | 12/2003 | Sumanaweera et al. |
| 6,666,863 B2 | 12/2003 | Wentzel et al. |
| 6,704,593 B2 | 3/2004 | Stainsby |
| 6,708,052 B1 | 3/2004 | Mao et al. |
| 6,711,436 B1 | 3/2004 | Duhaylongsod |
| 6,718,055 B1 | 4/2004 | Suri |
| 6,726,675 B1 | 4/2004 | Beyar |
| 6,728,566 B1 | 4/2004 | Subramanyan |

(56) References Cited

U.S. PATENT DOCUMENTS

| | | |
|---|---|---|
| 6,731,973 B2 | 5/2004 | Voith |
| 6,786,896 B1 | 9/2004 | Madhani et al. |
| 6,788,827 B1 | 9/2004 | Makram-Ebeid |
| 6,796,972 B1 | 9/2004 | Sinofsky et al. |
| 6,835,177 B2 | 12/2004 | Fritz et al. |
| 6,858,003 B2 | 2/2005 | Evans et al. |
| 6,912,471 B2 | 6/2005 | Heigl |
| 6,937,696 B1 | 8/2005 | Mostafavi |
| 6,959,266 B1 | 10/2005 | Mostafavi |
| 6,973,202 B2 | 12/2005 | Mostafavi |
| 6,980,675 B2 | 12/2005 | Evron et al. |
| 6,996,430 B1 | 2/2006 | Gilboa et al. |
| 6,999,852 B2 | 2/2006 | Green |
| 7,031,504 B1 | 4/2006 | Argiro et al. |
| 7,070,555 B2 | 7/2006 | Siess |
| 7,085,342 B2 | 8/2006 | Younis et al. |
| 7,134,994 B2 | 11/2006 | Alpert |
| 7,155,046 B2 | 12/2006 | Aben et al. |
| 7,155,315 B2 | 12/2006 | Niemeyer et al. |
| 7,180,976 B2 | 2/2007 | Wink et al. |
| 7,191,100 B2 | 3/2007 | Mostafavi |
| 7,209,779 B2 | 4/2007 | Kaufman |
| 7,215,802 B2 | 5/2007 | Klingensmith |
| 7,221,973 B2 | 5/2007 | Nitz |
| 7,269,457 B2 | 9/2007 | Shafer |
| 7,289,652 B2 | 10/2007 | Florent et al. |
| 7,321,677 B2 | 1/2008 | Evron et al. |
| 7,339,585 B2 | 3/2008 | Verstraelen et al. |
| 7,343,032 B2 | 3/2008 | Oakley et al. |
| 7,343,195 B2 | 3/2008 | Strommer et al. |
| 7,359,554 B2 | 4/2008 | Klingensmith |
| 7,369,691 B2 | 5/2008 | Kondo et al. |
| 7,397,935 B2 | 7/2008 | Kimmel |
| 7,398,116 B2 | 7/2008 | Edwards |
| 7,517,318 B2 | 4/2009 | Altmann |
| 7,545,967 B1 | 6/2009 | Prince et al. |
| 7,546,154 B2 | 6/2009 | Hornegger et al. |
| 7,587,074 B2 | 9/2009 | Zarkh et al. |
| 7,599,730 B2 | 10/2009 | Hunter |
| 7,604,601 B2 | 10/2009 | Altmann |
| 7,650,179 B2 | 1/2010 | Redel et al. |
| 7,653,426 B2 | 1/2010 | Yatsuo et al. |
| 7,668,362 B2 | 2/2010 | Olson et al. |
| 7,693,349 B2 | 4/2010 | Gering |
| 7,697,974 B2 | 4/2010 | Jenkins |
| 7,713,210 B2 | 5/2010 | Byrd |
| 7,729,743 B2 | 6/2010 | Sabczynski et al. |
| 7,729,746 B2 | 6/2010 | Redel et al. |
| 7,740,584 B2 | 6/2010 | Donaldson |
| 7,742,629 B2 | 6/2010 | Zarkh et al. |
| 7,773,787 B2 | 8/2010 | Tek et al. |
| 7,773,792 B2 | 8/2010 | Kimmel |
| 7,778,488 B2 | 8/2010 | Nord |
| 7,778,688 B2 | 8/2010 | Strommer |
| 7,822,291 B2 | 10/2010 | Guetter |
| 7,831,076 B2 | 11/2010 | Altmann |
| 7,844,126 B2 | 11/2010 | Mory et al. |
| 7,848,553 B2 | 12/2010 | Hertel |
| 7,877,132 B2 | 1/2011 | Rongen |
| 7,889,905 B2 | 2/2011 | Higgins et al. |
| 7,892,177 B2 | 2/2011 | Rold et al. |
| 7,914,442 B1 | 3/2011 | Gazdzinski |
| 7,916,912 B2 | 3/2011 | Abramov et al. |
| 7,925,064 B2 | 4/2011 | Cloutier et al. |
| 7,925,069 B2 | 4/2011 | Ortyn et al. |
| 7,925,327 B2 | 4/2011 | Weese |
| 7,927,275 B2 | 4/2011 | Kuban |
| 7,930,014 B2 | 4/2011 | Huennekens et al. |
| 7,935,055 B2 | 5/2011 | Burckhardt |
| 7,961,926 B2 | 6/2011 | Viswanathan |
| 7,965,905 B2 | 6/2011 | Allon et al. |
| 7,970,187 B2 | 6/2011 | Puts |
| 7,978,916 B2 | 7/2011 | Klingensmith |
| 7,992,100 B2 | 8/2011 | Lundstrom |
| 8,025,622 B2 | 9/2011 | Rold et al. |
| 8,029,447 B2 | 10/2011 | Kanz |
| 8,052,605 B2 | 11/2011 | Muller |
| 8,055,327 B2 | 11/2011 | Strommer et al. |
| 8,077,939 B2 | 12/2011 | Le Bezet et al. |
| 8,080,474 B2 | 12/2011 | Chen |
| 8,086,000 B2 | 12/2011 | Weijers |
| 8,126,241 B2 | 2/2012 | Zarkh et al. |
| 8,155,411 B2 | 4/2012 | Hof |
| 8,157,742 B2 | 4/2012 | Taylor |
| 8,165,361 B2 | 4/2012 | Li |
| 8,172,763 B2 | 5/2012 | Nelson |
| 8,189,886 B2 | 5/2012 | Huo et al. |
| 8,199,981 B2 | 6/2012 | Koptenko et al. |
| 8,200,040 B2 | 6/2012 | Pfister |
| 8,208,995 B2 | 6/2012 | Tearney et al. |
| 8,213,676 B2 | 7/2012 | Bendall |
| 8,233,718 B2 | 7/2012 | Klingensmith |
| 8,260,395 B2 | 9/2012 | Markowitz et al. |
| 8,271,068 B2 | 9/2012 | Khamene |
| 8,275,201 B2 | 9/2012 | Rangawala et al. |
| 8,289,284 B2 | 10/2012 | Glynn |
| 8,295,577 B2 | 10/2012 | Zarkh et al. |
| 8,298,147 B2 | 10/2012 | Huennekens |
| 8,303,503 B2 | 11/2012 | Nair |
| 8,364,242 B2 | 1/2013 | Li |
| 8,396,276 B2 | 3/2013 | Gatta |
| 8,396,533 B2 | 3/2013 | Barbu et al. |
| 8,409,098 B2 | 4/2013 | Olson |
| 8,411,927 B2 | 4/2013 | Chang et al. |
| 8,428,318 B2 | 4/2013 | Zhuo |
| 8,428,691 B2 | 4/2013 | Byrd |
| 8,433,115 B2 | 4/2013 | Chen |
| 8,457,374 B2 | 6/2013 | Lendl |
| 8,478,387 B2 | 7/2013 | Xu |
| 8,483,488 B2 | 7/2013 | Richter |
| 8,515,146 B2 | 8/2013 | Zhu et al. |
| 8,565,859 B2 | 10/2013 | Wang et al. |
| 8,605,976 B2 | 12/2013 | Diamant et al. |
| 8,625,865 B2 | 1/2014 | Zarkh et al. |
| 8,700,128 B2 | 4/2014 | Assis et al. |
| 8,731,642 B2 | 5/2014 | Zarkh et al. |
| 8,861,830 B2 | 10/2014 | Brada et al. |
| 2001/0031919 A1 | 2/2001 | Strommer et al. |
| 2001/0055418 A1 | 12/2001 | Nakamura |
| 2002/0049375 A1 | 4/2002 | Strommer et al. |
| 2002/0058869 A1 | 5/2002 | Axelsson et al. |
| 2002/0087089 A1 | 7/2002 | Ben-Haim |
| 2002/0090119 A1 | 7/2002 | Saito et al. |
| 2002/0114497 A1 | 8/2002 | Wetzel et al. |
| 2002/0188307 A1 | 12/2002 | Pintor et al. |
| 2002/0193686 A1 | 12/2002 | Gilboa |
| 2003/0014100 A1 | 1/2003 | Maria Meens et al. |
| 2003/0018251 A1 | 1/2003 | Solomon |
| 2003/0021381 A1 | 1/2003 | Koppe et al. |
| 2003/0023141 A1 | 1/2003 | Stelzer et al. |
| 2003/0139772 A1 | 3/2003 | Fisher et al. |
| 2003/0069499 A1 | 4/2003 | Lienard et al. |
| 2003/0088179 A1 | 5/2003 | Seeley et al. |
| 2003/0095710 A1 | 5/2003 | Tessadro |
| 2003/0129750 A1 | 7/2003 | Schwartz |
| 2003/0157073 A1 | 8/2003 | Peritt |
| 2004/0034380 A1 | 2/2004 | Woolfson et al. |
| 2004/0077941 A1 | 4/2004 | Reddy et al. |
| 2004/0097805 A1* | 5/2004 | Verard et al. ............... 600/428 |
| 2004/0133129 A1 | 7/2004 | Harari et al. |
| 2004/0165756 A1 | 8/2004 | Mielekamp |
| 2004/0176681 A1 | 9/2004 | Mao et al. |
| 2004/0215235 A1 | 10/2004 | Jackson et al. |
| 2004/0249270 A1 | 12/2004 | Kondo et al. |
| 2004/0254570 A1 | 12/2004 | Hadjicostis et al. |
| 2004/0267113 A1 | 12/2004 | Thomson |
| 2005/0004503 A1 | 1/2005 | Samson et al. |
| 2005/0008210 A1 | 1/2005 | Evron et al. |
| 2005/0015009 A1* | 1/2005 | Mourad et al. ............... 600/438 |
| 2005/0031176 A1 | 2/2005 | Hertel |
| 2005/0033199 A1 | 2/2005 | van der Steen |
| 2005/0043614 A1 | 2/2005 | Huizenga et al. |
| 2005/0054916 A1 | 3/2005 | Mostafavi |
| 2005/0067568 A1 | 3/2005 | Harding et al. |

(56) References Cited

U.S. PATENT DOCUMENTS

| | | |
|---|---|---|
| 2005/0080336 A1 | 4/2005 | Byrd et al. |
| 2005/0089143 A1 | 4/2005 | Nakano et al. |
| 2005/0090737 A1 | 4/2005 | Burrel et al. |
| 2005/0201510 A1 | 4/2005 | Mostafavi |
| 2005/0228359 A1 | 4/2005 | Doyle |
| 2005/0096589 A1 | 5/2005 | Shachar |
| 2005/0107679 A1 | 5/2005 | Geiger et al. |
| 2005/0107688 A1 | 5/2005 | Strommer |
| 2005/0107808 A1 | 5/2005 | Evans et al. |
| 2005/0111719 A1 | 5/2005 | Pesatore et al. |
| 2005/0113685 A1 | 5/2005 | Maschke et al. |
| 2005/0137661 A1 | 6/2005 | Sra |
| 2005/0141766 A1 | 6/2005 | Nagakashi et al. |
| 2005/0143777 A1 | 6/2005 | Sra |
| 2005/0154281 A1 | 7/2005 | Xue et al. |
| 2005/0182295 A1 | 8/2005 | Soper et al. |
| 2005/0197557 A1 | 9/2005 | Strommer et al. |
| 2005/0197559 A1 | 9/2005 | Boese et al. |
| 2005/0197566 A1 | 9/2005 | Strommer et al. |
| 2005/0203375 A1 | 9/2005 | Willis et al. |
| 2005/0216039 A1 | 9/2005 | Lederman |
| 2005/0234331 A1 | 10/2005 | Sendai |
| 2005/0273050 A1 | 12/2005 | Yokoyama et al. |
| 2005/0288577 A1 | 12/2005 | Weese |
| 2006/0007188 A1* | 1/2006 | Reiner ............ 345/179 |
| 2006/0120581 A1 | 2/2006 | Eck et al. |
| 2006/0165270 A1 | 2/2006 | Borgert et al. |
| 2006/0058647 A1 | 3/2006 | Strommer et al. |
| 2006/0074285 A1 | 4/2006 | Zarkh et al. |
| 2006/0106318 A1 | 5/2006 | Davidson |
| 2006/0129142 A1 | 6/2006 | Reynolds |
| 2006/0147897 A1 | 7/2006 | Grinvald |
| 2006/0149134 A1 | 7/2006 | Soper et al. |
| 2006/0155327 A1 | 7/2006 | Briganti et al. |
| 2006/0159318 A1 | 7/2006 | Alyassin et al. |
| 2006/0173287 A1 | 8/2006 | Sabszynski et al. |
| 2006/0184016 A1 | 8/2006 | Glossop |
| 2006/0188135 A1 | 8/2006 | Zarkh et al. |
| 2006/0193505 A1 | 8/2006 | Glukhovsky et al. |
| 2006/0224188 A1 | 10/2006 | Libbus et al. |
| 2006/0224232 A1 | 10/2006 | Chobotov |
| 2006/0241369 A1 | 10/2006 | Lienard et al. |
| 2006/0241445 A1 | 10/2006 | Altmann |
| 2006/0241465 A1* | 10/2006 | Huennekens et al. ........ 600/458 |
| 2006/0241478 A1 | 10/2006 | Lewis |
| 2006/0253024 A1 | 11/2006 | Altmann |
| 2006/0253029 A1 | 11/2006 | Altmann |
| 2006/0253031 A1 | 11/2006 | Altmann |
| 2006/0257006 A1 | 11/2006 | Bredno et al. |
| 2006/0259137 A1 | 11/2006 | Artof et al. |
| 2006/0269108 A1 | 11/2006 | Viswanathan |
| 2006/0287595 A1 | 12/2006 | Maschke |
| 2007/0021816 A1 | 1/2007 | Rudin |
| 2007/0038061 A1 | 2/2007 | Huennekens et al. |
| 2007/0038081 A1 | 2/2007 | Eck et al. |
| 2007/0043292 A1 | 2/2007 | Camus |
| 2007/0053558 A1 | 3/2007 | Puts et al. |
| 2007/0055128 A1 | 3/2007 | Glossop |
| 2007/0055148 A1 | 3/2007 | Klingenbeck-Regn |
| 2007/0055359 A1 | 3/2007 | Messer et al. |
| 2007/0060798 A1 | 3/2007 | Krupnik et al. |
| 2007/0088431 A1 | 4/2007 | Bourang et al. |
| 2007/0106146 A1 | 5/2007 | Altmann et al. |
| 2007/0116342 A1 | 5/2007 | Zarkh et al. |
| 2007/0123771 A1 | 5/2007 | Redel et al. |
| 2007/0135707 A1 | 6/2007 | Redel et al. |
| 2007/0142907 A1 | 6/2007 | Moaddeb et al. |
| 2007/0147706 A1 | 6/2007 | Sasaki et al. |
| 2007/0165916 A1 | 7/2007 | Cloutier et al. |
| 2007/0173861 A1 | 7/2007 | Strommer |
| 2007/0198008 A1 | 8/2007 | Hauck et al. |
| 2007/0208388 A1 | 9/2007 | Jahns |
| 2007/0219546 A1 | 9/2007 | Mody et al. |
| 2007/0219630 A1 | 9/2007 | Chu |
| 2007/0232896 A1 | 10/2007 | Gilboa et al. |
| 2007/0238999 A1 | 10/2007 | Specht |
| 2007/0248253 A1 | 10/2007 | Manzke et al. |
| 2007/0255139 A1 | 11/2007 | Deschinger |
| 2007/0269135 A1 | 11/2007 | Ono |
| 2007/0276216 A1 | 11/2007 | Beyar et al. |
| 2008/0008366 A1 | 1/2008 | Desh |
| 2008/0015677 A1 | 1/2008 | Glossop et al. |
| 2008/0021331 A1 | 1/2008 | Grinvald |
| 2008/0051648 A1 | 2/2008 | Suri et al. |
| 2008/0221439 A1 | 3/2008 | Iddan et al. |
| 2008/0221440 A1 | 3/2008 | Iddan et al. |
| 2008/0221442 A1 | 3/2008 | Tolkowsky et al. |
| 2008/0082049 A1 | 4/2008 | Evans et al. |
| 2008/0089566 A1 | 4/2008 | Node-Langlois |
| 2008/0114238 A1 | 5/2008 | Lloyd |
| 2008/0118117 A1 | 5/2008 | Gauldie et al. |
| 2008/0119922 A1 | 5/2008 | Alkhatib |
| 2008/0137923 A1 | 6/2008 | Spahn |
| 2008/0137935 A1 | 6/2008 | Spahn |
| 2008/0146923 A1 | 6/2008 | Mejia |
| 2008/0146928 A1 | 6/2008 | Dala-Krishna |
| 2008/0146942 A1 | 6/2008 | Dala-Krishna |
| 2008/0177183 A1 | 7/2008 | Courtney |
| 2008/0188739 A1 | 8/2008 | Rongen et al. |
| 2008/0247621 A1 | 10/2008 | Zarkh et al. |
| 2008/0253686 A1 | 10/2008 | Bayer |
| 2008/0262346 A1 | 10/2008 | Assis et al. |
| 2008/0267475 A1 | 10/2008 | Lendl |
| 2008/0283771 A1 | 11/2008 | Li |
| 2008/0294038 A1* | 11/2008 | Weese ............ A61B 6/481 600/431 |
| 2008/0300487 A1 | 12/2008 | Govari |
| 2009/0016587 A1* | 1/2009 | Strobel ............ A61B 6/469 382/130 |
| 2009/0074284 A1 | 3/2009 | Zeineh et al. |
| 2009/0093676 A1 | 4/2009 | Davidson |
| 2009/0103682 A1 | 4/2009 | Chen et al. |
| 2009/0105579 A1 | 4/2009 | Garibaldi |
| 2009/0116715 A1* | 5/2009 | Bredno ............ A61B 6/481 382/130 |
| 2009/0136099 A1 | 5/2009 | Boyden et al. |
| 2009/0299195 A1 | 5/2009 | Muller et al. |
| 2009/0306547 A1 | 6/2009 | Iddan et al. |
| 2009/0171201 A1 | 7/2009 | Olson |
| 2009/0177444 A1 | 7/2009 | Wiemker et al. |
| 2009/0216112 A1 | 8/2009 | Assis et al. |
| 2009/0245601 A1 | 10/2009 | Cohen et al. |
| 2009/0257631 A1 | 10/2009 | Baumgart |
| 2009/0264752 A1 | 10/2009 | Markowitz et al. |
| 2009/0264753 A1 | 10/2009 | Von Schulthes |
| 2009/0275831 A1 | 11/2009 | Hall |
| 2009/0281418 A1 | 11/2009 | Ruijters et al. |
| 2009/0304593 A1 | 12/2009 | Frinking et al. |
| 2010/0041949 A1 | 2/2010 | Tolkowsky |
| 2010/0049034 A1 | 2/2010 | Eck et al. |
| 2010/0054573 A1 | 3/2010 | Shekhara |
| 2010/0067768 A1 | 3/2010 | Ionasec et al. |
| 2010/0094124 A1 | 4/2010 | Schoonenberg et al. |
| 2010/0094127 A1 | 4/2010 | Xu |
| 2010/0099979 A1 | 4/2010 | Schoonenberg et al. |
| 2010/0111396 A1 | 5/2010 | Boucheron |
| 2010/0114289 A1 | 5/2010 | Camus |
| 2010/0123715 A1 | 5/2010 | Hansegard |
| 2010/0220917 A1 | 5/2010 | Steinberg et al. |
| 2010/0222671 A1 | 5/2010 | Cohen et al. |
| 2010/0228076 A1 | 5/2010 | Blank et al. |
| 2010/0134517 A1 | 6/2010 | Saikaly et al. |
| 2010/0135546 A1 | 6/2010 | Cziria |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161022 A1 | 6/2010 | Tolkowsky |
| 2010/0161023 A1 | 6/2010 | Cohen et al. |
| 2010/0171819 A1 | 7/2010 | Tolkowsky et al. |
| 2010/0172556 A1 | 7/2010 | Cohen et al. |
| 2010/0174192 A1 | 7/2010 | Azuma |
| 2010/0191102 A1 | 7/2010 | Steinberg et al. |
| 2010/0198063 A1 | 8/2010 | Huber |
| 2010/0246910 A1 | 9/2010 | Wiemker |

(56) References Cited

U.S. PATENT DOCUMENTS

| | | |
|---|---|---|
| 2010/0272340 A1 | 10/2010 | Bar-Aviv et al. |
| 2010/0290693 A1 | 11/2010 | Cohen et al. |
| 2010/0310140 A1 | 12/2010 | Schneider |
| 2010/0312100 A1 | 12/2010 | Zarkh et al. |
| 2010/0318115 A1 | 12/2010 | Chanduszko et al. |
| 2010/0331670 A1 | 12/2010 | Strommer et al. |
| 2011/0015520 A1 | 1/2011 | Meetz et al. |
| 2011/0026786 A1 | 2/2011 | Mohamed |
| 2011/0033094 A1 | 2/2011 | Zarkh |
| 2011/0034801 A1 | 2/2011 | Baumgart |
| 2011/0052030 A1 | 3/2011 | Bruder et al. |
| 2011/0071404 A1 | 3/2011 | Schmidtt et al. |
| 2011/0075912 A1 | 3/2011 | Rieber et al. |
| 2011/0087104 A1 | 4/2011 | Moore |
| 2011/0096969 A1 | 4/2011 | Zheng et al. |
| 2011/0112398 A1 | 5/2011 | Zarkh et al. |
| 2011/0118825 A1 | 5/2011 | Hunter et al. |
| 2011/0150309 A1 | 6/2011 | Barfett et al. |
| 2011/0157154 A1 | 6/2011 | Bernard et al. |
| 2011/0228992 A1 | 9/2011 | Wels et al. |
| 2011/0230758 A1 | 9/2011 | Eichler |
| 2011/0235889 A1 | 9/2011 | Spahn |
| 2011/0274333 A1 | 11/2011 | Prevrhal et al. |
| 2011/0286627 A1 | 11/2011 | Takacs et al. |
| 2011/0293163 A1 | 12/2011 | Kargar et al. |
| 2011/0319752 A1 | 12/2011 | Steinberg et al. |
| 2012/0004529 A1 | 1/2012 | Tolkowsky et al. |
| 2012/0004533 A1 | 1/2012 | Peng |
| 2012/0004537 A1 | 1/2012 | Tolkowsky et al. |
| 2012/0014574 A1 | 1/2012 | Ferschel et al. |
| 2012/0029339 A1 | 2/2012 | Cohen et al. |
| 2012/0051606 A1 | 3/2012 | Saikia |
| 2012/0059220 A1 | 3/2012 | Holsing |
| 2012/0059253 A1 | 3/2012 | Wang et al. |
| 2012/0065507 A1 | 3/2012 | Brunke |
| 2012/0069167 A1 | 3/2012 | Liu et al. |
| 2012/0072190 A1 | 3/2012 | Sharma et al. |
| 2012/0082360 A1 | 4/2012 | Florent |
| 2012/0083696 A1 | 4/2012 | Kitamura |
| 2012/0093379 A1 | 4/2012 | Florent et al. |
| 2012/0123238 A1 | 5/2012 | Vaillant et al. |
| 2012/0130242 A1 | 5/2012 | Burgess |
| 2012/0140998 A1 | 6/2012 | Zhu |
| 2012/0207367 A1 | 8/2012 | Kneepkens |
| 2012/0215093 A1 | 8/2012 | Ji |
| 2012/0224751 A1 | 9/2012 | Kemp |
| 2012/0230565 A1 | 9/2012 | Steinberg et al. |
| 2012/0243761 A1* | 9/2012 | Senzig ............ G06T 11/008 382/131 |
| 2012/0245460 A1 | 9/2012 | Slomka |
| 2012/0250974 A1 | 10/2012 | Miyamoto |
| 2012/0294498 A1 | 11/2012 | Popovic |
| 2012/0300981 A1 | 11/2012 | Yeh et al. |
| 2012/0310081 A1 | 12/2012 | Adler et al. |
| 2013/0004044 A1 | 1/2013 | Ross |
| 2013/0030295 A1 | 1/2013 | Huennekens |
| 2013/0046167 A1 | 2/2013 | Shah |
| 2013/0053664 A1 | 2/2013 | Jian et al. |
| 2013/0109958 A1 | 5/2013 | Baumgart |
| 2013/0109959 A1 | 5/2013 | Baumgart |
| 2013/0116739 A1 | 5/2013 | Brada et al. |
| 2013/0120296 A1 | 5/2013 | Merrit |
| 2013/0120297 A1 | 5/2013 | Merrit |
| 2013/0123616 A1 | 5/2013 | Merrit |
| 2013/0226003 A1* | 8/2013 | Edic ............ A61B 6/504 600/454 |
| 2013/0308844 A1 | 11/2013 | Florent et al. |
| 2013/0329030 A1 | 12/2013 | Tolkowsky et al. |
| 2013/0329977 A1 | 12/2013 | Tolkowsky et al. |
| 2014/0039276 A1 | 2/2014 | Hattangadi et al. |
| 2014/0094660 A1 | 4/2014 | Tolkowsky et al. |
| 2014/0094689 A1 | 4/2014 | Cohen et al. |
| 2014/0094690 A1 | 4/2014 | Tolkowsky et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0100451 A1 | 4/2014 | Tolkowsky et al. |
| 2014/0107479 A1 | 4/2014 | Klaiman et al. |
| 2014/0111541 A1 | 4/2014 | Tolkowsky et al. |
| 2014/0112566 A1 | 4/2014 | Steinberg et al. |
| 2014/0114184 A1 | 4/2014 | Klaiman et al. |
| 2014/0114185 A1 | 4/2014 | Tolkowsky et al. |
| 2014/0114308 A1 | 4/2014 | Tolkowsky et al. |
| 2014/0114333 A1 | 4/2014 | Tolkowsky et al. |
| 2014/0121513 A1 | 5/2014 | Tolkowsky et al. |
| 2015/0282737 A1 | 10/2015 | Tolkowsky et al. |
| 2015/0282889 A1 | 10/2015 | Cohen et al. |
| 2015/0282890 A1 | 10/2015 | Cohen et al. |
| 2015/0283319 A1 | 10/2015 | Tolkowsky et al. |

FOREIGN PATENT DOCUMENTS

| | | |
|---|---|---|
| WO | 94/010904 | 5/1994 |
| WO | 99/07354 A2 | 2/1999 |
| WO | 00/33755 A1 | 6/2000 |
| WO | 01/10313 A1 | 2/2001 |
| WO | 01/43642 | 6/2001 |
| WO | 2003/043516 A2 | 5/2003 |
| WO | 03/096894 | 11/2003 |
| WO | 05/026891 | 3/2005 |
| WO | 2005/051452 A2 | 6/2005 |
| WO | 05/124689 | 12/2005 |
| WO | 2006/027781 A2 | 3/2006 |
| WO | 06/066122 | 6/2006 |
| WO | 06/066124 | 6/2006 |
| WO | 2006061814 | 6/2006 |
| WO | 2006/076409 A2 | 7/2006 |
| WO | 06/121984 | 11/2006 |
| WO | 2006/114721 A2 | 11/2006 |
| WO | 2007/002685 A2 | 1/2007 |
| WO | 2007/014028 A1 | 2/2007 |
| WO | 2007/015199 A2 | 2/2007 |
| WO | 2007/066249 | 6/2007 |
| WO | 2008/007350 A1 | 1/2008 |
| WO | 2008/062358 A1 | 5/2008 |
| WO | 08/107905 | 9/2008 |
| WO | 2008/104909 A1 | 9/2008 |
| WO | 09/153794 | 12/2009 |
| WO | 2010/058398 A2 | 5/2010 |
| WO | 2011/046903 A2 | 4/2011 |
| WO | 2011/046904 A1 | 4/2011 |
| WO | 2011128797 A1 | 10/2011 |
| WO | 2011/145094 A2 | 11/2011 |
| WO | 2012/014212 A1 | 2/2012 |
| WO | 2012021307 A2 | 2/2012 |
| WO | 2012/028190 A1 | 3/2012 |
| WO | 2012095755 A1 | 7/2012 |
| WO | 2012107857 A1 | 8/2012 |
| WO | 2012/138872 A2 | 10/2012 |
| WO | 2012/138874 A2 | 10/2012 |
| WO | 2012/176191 A1 | 12/2012 |
| WO | 2013/025602 A1 | 2/2013 |
| WO | 2013061225 A1 | 5/2013 |
| WO | 2013/084345 A1 | 6/2013 |
| WO | 2013/128233 A1 | 9/2013 |
| WO | 2013/169814 A1 | 11/2013 |
| WO | 2013/175472 A2 | 11/2013 |
| WO | 2014/002095 A2 | 1/2014 |
| WO | 2015/155770 A1 | 10/2015 |
| WO | 2015/173821 A1 | 11/2015 |

OTHER PUBLICATIONS

"Wang et al.," "Quantification of fractional flow reserve based on angiographic image data," Int J Cardiovasc Imaging 28:13-22, 2012 (published online on Jan. 7, 2011) (Year: 2011).*

"Pijls et al.," "Functional Measurement of Coronary Stenosis," Journal of the American College of Cardiology, pp. 1045-1055, vol. 59, No. 12, Mar. 2012 (Year: 2012).*

"Blows et al.," "The pressure wire in practice," Heart Review, 93: 419-422, Heart 2007 (Year: 2007).*

(56) References Cited

OTHER PUBLICATIONS

Boyle et al., entitled "Assessment of a Novel Angiographic Image Stabilization System for Percutaneous Coronary Intervention" (Journal of Interventional Cardiology, vol. 20 No. 2, 2007.
Timinger et al., entitled "Motion compensated coronary interventional navigation by means of diaphragm tracking and elastic motion models" (Phys Med Biol. Feb. 7, 2005;50(3):491-503.
Timinger et al., entitled "Motion compensation for interventional navigation on 3D static roadmaps based on an affine model and gating" (Phys Med Biol. Mar. 7, 2004;49(5):719-32.
Turski et al., entitled "Digital Subtraction Angiography 'Road Map'" (American Journal of Roentgenology, 1982.
Iddan et al., entitled "3D imaging in the studio and elsewhere" (SPIE Proceedings vol. 4298, 2001.
"Catheter Insertion Simulation with Combined Visual and Haptic Feedback," by Zorcolo et al. (Center for Advanced Studies, Research and Development in Sardinia).
"4D-CT imaging of a volume influenced by respiratory motion on multi-slice CT Tinsu Pan," by Lee et al., (Medical Physics, Feb. 2004, vol. 31, Issue 2, pp. 333-340)—an abstract.
"New 4-D imaging for real-time intraoperative MRI: adaptive 4-D scan," by Tokuda et al. (Med Image Comput Assist Interv Int Conf. 2006;9(Pt 1):454-61) an abstract.
"Real-time interactive viewing of 4D kinematic MR joint studies," by Schulz et al. (Med Image Comput Assist Interv Int Conf. 2005;8(Pt 1):467-73.)—an abstract.
"4D smoothing of gated SPECT images using a left-ventricle shape model and a deformable mesh," by Brankov et al., (Nuclear Science Symposium Conference Record, 2004 IEEE, Oct. 2004, vol. 5, 2845-2848).
"Prospective motion correction of X-ray images for coronary interventions," by Shechter et al. (IEEE Trans Med Imaging. Apr. 2005;24(4):441-50).
"Cardiac Imaging: We Got the Beat!" by Elizabeth Morgan (Medical Imaging, Mar. 2005).
"Noninvasive Coronary Angiography by Retrospectively ECG-Gated Multislice Spiral CT," by Achenbach et al., (Circulation. Dec. 5, 2000;102(23):2823-8).
"Spatially-adaptive temporal smoothing for reconstruction of dynamic and gated image sequences," by Brankov et al., (Nuclear Science Symposium Conference Record, 2000 IEEE, 2000, vol. 2, 15/146-15/150)—an abstract.
"Full-scale clinical implementation of a video based respiratory gating system," by Ramsey et al., (Engineering in Medicine and Biology Society, 2000. Proceedings of the 22nd Annual International Conference of the IEEE, 2000, vol. 3, 2141-2144)—an abstract.
"Three-Dimensional Respiratory-Gated MR Angiography of the Coronary Arteries: Comparison with Conventional Coronary Angiography," by Post et al., (AJR, 1996; 166: 1399-1404).
Soffie Mansson, et al., "Dosimetric verification of breathing adapted radiotherapy using polymer gel", Journal of Physics: Conference series 56 (200) 300-303.
"From 2D to 4D" AXIOM Innovations—Mar. 2008, www.siemens.com/healthcare-magazine.
A Brochure: Impella® 2.5, Percutaneous Circulatory Support System, ABIOMED™, 2007.
Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137).
Dijkstra, entitled "A Note on Two Problems in Connexion with Graphs" (Numerische Mathematik I, 269-271, 1959).
Zarkh et al., entitled "Guide wire navigation and therapeutic device localization for catheterization procedure" (International Congress Series 1281 (2005) 311-316.
Brochure: At the Transvascular Cardiovascular Therapeutics (TCT) conference held in Washington DC, USA in Oct. 2008, Paieon Inc. demonstrated the CardiOp-THV system for real-time navigation and positioning of a trans-catheter heart valve.
Brochure: At the TCT conference held in San Francisco, USA in Sep. 2009, Paieon Inc. demonstrated the IC-PRO Comprehensive Imaging Workstation for providing assistance in cardiac catheterization procedures.
An International Search Report dated Sep. 8, 2009, which issued during the prosecution of Applicant's PCT/IL09/00610.
An International Search Report dated Jan. 15, 2009, issued during the prosecution of Applicant's PCT Patent Application No. PCT/IL08/000316.
An International Search Report dated May 19, 2010 issued during the prosecution of Applicant's PCT Patent Application No. PCT/IL2009/001089.
"A new point matching algorithm for non-rigid registration," by Chui (Computer Vision and Image Understanding 89 (2003) 114-141).
"Advanced and Challenges in Super-Resolution," by Farsiu (International Journal of Imaging Systems and Technology, vol. 14, No. 2, pp. 47-57, Special issue on high-resolution image reconstruction, Aug. 2004).
"Image Registration by Minimization of Residual Complexity," by Myronenko (CVPR 2009).
"Image inpainting," by Bertalmio (ACM Siggraph 2000, New Orleans, Louisiana, USA, Jul. 2000).
"Nonrigid registration using free-form deformations: application to breast MR images," by Rueckert, (IEEE Trans. Med. Img, vol. 18, No. 8, 1999).
"Unwarping of unidirectionally distorted EPI images," by Kybic (IEEE Trans. Med. Img., vol. 19, No. 2, 2000).
"Geometrically Correct 3-D Reconstruction of Intravascular Ultrasound Images by Fusion with Biplane Angiography—Methods and Validation," Andreas Wahle, IEEE Transactions on Medical Imaging, Final Manuscript #187/98, Jun. 30, 1999.
An International Search Report dated Jan. 6, 2012, which issued during the prosecution of Applicant's PCT Application No. PCT/IL11/00391.
An Official Action dated Nov. 28, 2011, which issued during the prosecution of Applicant's U.S. Appl. No. 12/075,252.
An Official Action dated Dec. 8, 2011, which issued during the prosecution of Applicant's U.S. Appl. No. 12/075,244.
U.S. Appl. No. 60/845,347 to Strommer et al., filed Sep. 2006.
International Search Report dated Mar. 2, 2012, issued in PCT/IL11/00612.
Office Action dated Mar. 14, 2012, issued in U.S. Appl. No. 12/075,214.
Office Action dated Mar. 15, 2012, issued in U.S. Appl. No. 12/649,944.
Office Action dated Mar. 15, 2012, issued in U.S. Appl. No. 12/650,152.
Office Action dated May 22, 2012, issued in U.S. Appl. No. 12/075,244.
Umeda, H. et al., "Promising efficacy of primary gradual and prolonged balloon angioplasty in small coronary arteries: A randomized comparison with cutting balloon angioplasty and conventional balloon angioplasty", 2004.
W. Santamore et al., "A microcomputer based automated quantative coronary angiographic analysis system," Annals of Biomedical Engineering, vol. 16, pp. 367-377, 1988.
V. Duddalwar, "Multislice CT angiography: a practical guide to CT angiography in vascular imaging and intervention," The British Journal of Radiology, 77 (2004), S27-S38.
Official Action dated Oct. 23, 2012, which issued during the prosecution of JP Application No. 2009-552328.
Official Action dated Nov. 23, 2012, which issued during the prosecution of U.S. Appl. No. 12/649,944.
Official Action dated Aug. 27, 2012, which issued during the prosecution U.S. Appl. No. 12/075,214.
International Search Report dated Oct. 10, 2012, which issued during the prosecution of PCT/IL2012/000246.
Communication dated Sep. 5, 2012, which issued during the prosecution of EP Application 09 766 329.8-1526.
Communication dated Oct. 29, 2012, which issued during the prosecution of EP Application 08 719941.0-1265/2129284.
Computer translation of JP 2010-253017 to Takeshi.

(56) References Cited

OTHER PUBLICATIONS

G. Mancini et al., "Automated quantitative coronary arteriography: morphologic and physiologic validation in vivo of a rapid digital angiographic method," Circulation 1987;75:452-460.
I. Kompatsiaris et al., "Deformable Boundary Detection of Stents in Angiographic Images," IEEE Transactions on Medical Imaging, vol. 19, No. 6, Jun. 2000.
L. Yaneza et al., "Atherosclerotic Plaque Can Be Quantified Using Multifractal and Wavelet Decomposition Techniques," Abstracts—Angiography & Interventional Cardiology, JACC Mar. 3, 2004.
Official Action dated Oct. 31, 2012, which issued during the prosecution U.S. Appl. No. 12/075,244.
Official Action dated Sep. 20, 2012, which issued during the prosecution of U.S. Appl. No. 12/649,955.
U.S. Appl. No. 61/359,431.
W. Goodman et al., "Coronary-Artery Calcification in Young Adults With End-Stage Renal Disease Who Are Undergoing Dialysis," The New England Journal of Medicine, vol. 342 No. 20.
W. Leung et al., "Coronary Artery Quantitation and Data Management System for Paired Cineangiograms," Catheterization and Cardiovascular Diagnosis 24:121-134 (1991).
A search report dated Nov. 23, 2012, which issued during the prosecution of Applicant's EP Application 09 827264.4-1265/2358269.
An examination report dated Dec. 5, 2012, which issued during the prosecution of Applicant's EP Application 09766329.8.
An Official Action dated Dec. 10, 2012, which issued during the prosecution of Applicant's U.S. Appl. No. 12/650,156.
An Official Action dated Dec. 11, 2012, which issued during the prosecution of Applicant's U.S. Appl. No. 12/650,152.
An Official Action dated Jan. 22, 2013, which issued during the prosecution of Applicant's U.S. Appl. No. 12/650,121.
An Official Action dated Jan. 28, 2013, which issued during the prosecution of Applicant's U.S. Appl. No. 12/781,366.
An Official Action dated Feb. 4, 2013, which issued during the prosecution of Applicant's U.S. Appl. No. 13/228,185.
Peng Wang et al.: "Image-Based Device Tracking for the Co-registration of Angiography and Intravascular Ultrasound Images", MICCAI 2011, Part I, LINCS 6891, pp. 161-168, 2011.
An Official Action dated Jul. 2, 2013, which issued during the prosecution of Applicant's U.S. Appl. No. 12/075,244.
An Official Action dated Jun. 19, 2013, which issued during the prosecution of Applicant's U.S. Appl. No. 12/075,214.
An Official Action dated May 31, 2013, which issued during the prosecution of Applicant's U.S. Appl. No. 12/075,252.
An Official Action dated May 6, 2013, which issued during the prosecution of Applicant's U.S. Appl. No. 12/487,315.
A Notice of Allowance dated Jun. 4, 2013, which issued in Applicant's U.S. Appl. No. 12/649,960.
An Official Action dated Sep. 6, 2013, which issued during the prosecution of Applicant's U.S. Appl. No. 12/650,605.
An Official Action dated Aug. 30, 2013, which issued during the prosecution of Applicant's U.S. Appl. No. 12/650,121.
An Official Action dated Sep. 12, 2013, which issued during the prosecution of Applicant's U.S. Appl. No. 12/781,366.
A Notice of Allowance in Applicant's U.S. Appl. No. 12/781,414.
An Official Action dated Aug. 3, 2012, which issued during the prosecution of Applicant's U.S. Appl. No. 12/781,294.
An Official Action dated Jun. 19, 2012, which issued during the prosecution of Applicant's U.S. Appl. No. 12/075,252.
An Official Action dated Jun. 18, 2012, which issued during the prosecution of Applicant's U.S. Appl. No. 12/781,366.
An Official Action dated Jun. 7, 2012, which issued during the prosecution of Applicant's U.S. Appl. No. 12/650,156.
An Official Action dated May 29, 2012, which issued during the prosecution of Applicant's U.S. Appl. No. 12/650,121.
Buddy D. Ratner, "Biomaterials Science: An Introduction to Materials in Medicine", Elsevier, chapter 7, 1996.
Gerald E. Miller, "Fundamentals of Biomedical Transport Processes, Morgan & Claypool Publishers", chapter 2, 2010.
Gerhard Albert ten Brinke, "Automated coronary flow reserve assessment using planar x-ray angiography", PhD dissertation, Universiteit Twente, 2011.
Jerry T. Wong et al., "Quantification of fractional flow reserve based on angiographic image data", Int J Cardiovasc Imaging 28:13-22, Jan. 7, 2011.
Kassab, G. S. et al., "Cross-sectional area and volume compliance of porcine left coronary arteries," Am. J. Physiol. Heart Circ. Physiol. 281, H623-H628, Aug. 2011.
Molloi S. et al., "Absolute volumetric coronary blood flow measurement with digital subtraction angiography". Int J Card Imaging 14:137-145, 1998.
Molloi, S. et al., "Estimation of coronary artery hyperemic blood flow based on arterial lumen volume using angiographic images," The International Journal of Cardiovascular Imaging, vol. 28, No. 1, 1-11, Jan. 7, 2011.
Molloi, S. et al., "Quantification of coronary artery lumen volume by digital angiography: in vivo validation," Circulation 104, 2351-2357, Nov. 6, 2001.
Molloi, S. et al., "Quantification of volumetric coronary blood flow with dual-energy digital subtraction angiography," Circulation 93, 1919-1927, May 15, 1996.
Molloi, S. et al., "Regional volumetric coronary blood flow measurement by digital angiography: in vivo validation," Acad. Radiol. 11, 7, 757-766, Jul. 2004.
Sian Sen et al., "Development and Validation of a New, Adenosine-Independent Index of Stenosis Severity From Coronary Wave—Intensity Analysis". Journal of the American College of Cardiology, vol. 59, Apr. 10, 2012.
Yunlong Huo et al., "A validated predictive model of coronary fractional flow reserve," J. R. Soc. Interface, Nov. 23, 2011.
A Notice of Allowance issued in Applicant's U.S. Appl. No. 13/965,893.
An Official Action dated Nov. 13, 2013, which issued during the prosecution of Applicant's U.S. Appl. No. 12/666,879.
An Official Action dated Oct. 2, 2013, which issued during the prosecution of Applicant's U.S. Appl. No. 13/228,211.
An Official Action dated Oct. 21, 2013, which issued during the prosecution of Applicant's U.S. Appl. No. 12/075,214.
An Official Action dated Oct. 23, 2013, which issued during the prosecution of Applicant's U.S. Appl. No. 12/648,913.
An Official Action dated Oct. 25, 2013, which issued during the prosecution of Applicant's U.S. Appl. No. 12/781,366.
An Official Action dated Oct. 3, 2013, which issued during the prosecution of Applicant's U.S. Appl. No. 13/228,185.
An Official Action dated Oct. 30, 2013, which issued during the prosecution of Applicant's U.S. Appl. No. 13/228,335.
An Official Action dated Oct. 4, 2013, which issued during the prosecution of Applicant's U.S. Appl. No. 12/649,955.
Correspondence from the International Searching Authority in Applicant's PCT/IL13/50549.
Correspondence from the International Searching Authority in Applicant's PCT/IL2013/050438.
International Search Report and Written Opinion for International Patent Application PCT/IL2013/050438 dated Dec. 2, 2013.
Office Action, dated Jan. 7, 2014, issued by the United States Patent and Trademark Office, in counterpart U.S. Appl. No. 12/075,244.
Office Action, dated Feb. 12, 2014, issued by the United States Patent and Trademark Office, in counterpart U.S. Appl. No. 12/781,260.
Office Action, dated Dec. 31, 2013, issued by the United States Patent and Trademark Office, in counterpart U.S. Appl. No. 12/075,252.
Notice of Allowance, dated Jan. 3, 2014, issued by the United States Patent and Trademark Office, in counterpart U.S. Appl. No. 13/965,872.
Search Report, dated Jan. 22, 2014, issued by the International Searching Authority, in counterpart Application No. PCT/IL13/50549.
Written Opinion, dated Jan. 22, 2014, issued by the International Searching Authority, in counterpart Application No. PCT/IL13/50549.
An Official Action dated Feb. 20, 2014, which issued during the prosecution of Applicant's U.S. Appl. No. 12/075,214.
An Official Action dated May 6, 2014, which issued during the prosecution of Applicant's U.S. Appl. No. 12/075,252.

(56) References Cited

OTHER PUBLICATIONS

A Notice of Allowance issued in Applicant's U.S. Appl. No. 12/666,879.
An Official Action dated Mar. 21, 2014, which issued during the prosecution of Applicant's U.S. Appl. No. 12/648,913.
An Official Action dated Apr. 3, 2014, which issued during the prosecution of Applicant's U.S. Appl. No. 12/649,955.
An Official Action dated Mar. 14, 2014, which issued during the prosecution of Applicant's U.S. Appl. No. 12/650,605.
An Official Action dated Apr. 25, 2014, which issued during the prosecution of Applicant's U.S. Appl. No. 12/650,121.
An Official Action dated Apr. 24, 2014, which issued during the prosecution of Applicant's U.S. Appl. No. 12/781,366.
An Official Action dated Apr. 17, 2014, which issued during the prosecution of Applicant's U.S. Appl. No. 13/228,211.
An Official Action dated Apr. 28, 2014, which issued during the prosecution of Applicant's U.S. Appl. No. 13/228,185.
An Official Action dated May 5, 2014, which issued during the prosecution of Applicant's U.S. Appl. No. 14/096,968.
An Official Action dated Feb. 14, 2014, which issued during the prosecution of Applicant's U.S. Appl. No. 14/098,140.
Pyxaras et al., "Quantitative angiography optical coherence tomography for the functional assessment of nonobstructive coronary stenoses" (Medscape), Oct. 2013, 11 pages total.
Tu et al., "In vivo comparison of arterial lumen dimensions assessed by co-registered 3D quantitative coronary angiography intravascular ultrasound and optical coherence tomography.", Int J Cardiovasc Imaging (2012) 28:1315-1327, Jan. 20, 2012, DOI 10.1007/s10554-012-0016-6, 13 pages total.
Tu et al, "Fusion of 3D QCA and IVUS/OCT", Int J Cardiovasc Imaging (2011) 27:197-207, Jan. 25, 2011, DOI 10.1007/s10554-011-9809-2, 11 pages total.
A Notice of Allowance dated Jun. 24, 2014, issued in Applicant's U.S. Appl. No. 14/097,603.
An Official Action dated Jul. 3, 2014, which issued during the prosecution of Applicant's U.S. Appl. No. 12/648,913.
An Official Action dated Jul. 30, 2014, which issued during the prosecution of Applicant's U.S. Appl. No. 12/075,214.
An Official Action dated Jul. 31, 2014, which issued during the prosecution of Applicant's U.S. Appl. No. 12/649,944.
An Official Action dated Jun. 18, 2014, which issued during the prosecution of Applicant's U.S. Appl. No. 12/075,244.
An Official Action dated Jun. 3, 2014, which issued during the prosecution of Applicant's U.S. Appl. No. 12/781,260.
An Official Action dated May 21, 2014, which issued during the prosecution of Applicant's U.S. Appl. No. 12/650,156.
An Official Action dated May 29, 2014, which issued during the prosecution of Applicant's U.S. Appl. No. 14/097,922.
An Official Action dated May 30, 2014, which issued during the prosecution of Applicant's U.S. Appl. No. 13/228,335.
Communication dated Dec. 11, 2014, issued by the United States Patent and Trademark Office in corresponding U.S. Appl. No. 12/648,913.
Communication dated Feb. 4, 2015, issued by the United States Patent and Trademark Office in corresponding U.S. Appl. No. 12/649,955.
Communication dated Nov. 24, 2014, issued by the United States Patent and Trademark Office in corresponding U.S. Appl. No. 12/781,260.
Communication dated Jan. 6, 2015, issued by the United States Patent and Trademark Office in corresponding U.S. Appl. No. 12/650,605.
Communication dated Feb. 6, 2015, issued by the United States Patent and Trademark Office in corresponding U.S. Appl. No. 12/650,121.
Communication dated Nov. 24, 2014, issued by the United States Patent and Trademark Office in corresponding U.S. Appl. No. 12/649,944.
Communication dated Feb. 6, 2015, issued by the United States Patent and Trademark Office in corresponding U.S. Appl. No. 12/781,366.
Communication dated Jan. 16, 2015, issued by the United States Patent and Trademark Office in corresponding U.S. Appl. No. 13/228,229.
Communication dated Jan. 6, 2015, issued by the United States Patent and Trademark Office in corresponding U.S. Appl. No. 13/228,335.
Communication dated Nov. 28, 2014, issued by the United States Patent and Trademark Office in corresponding U.S. Appl. No. 14/097,922.
Communication dated Dec. 4, 2014, issued by the United States Patent and Trademark Office in corresponding U.S. Appl. No. 14/098,114.
Communication dated Nov. 24, 2014, issued by the United States Patent and Trademark Office in corresponding U.S. Appl. No. 12/650,156.
Communication dated Dec. 19, 2014, issued by the United States Patent and Trademark Office in corresponding U.S. Appl. No. 14/143,430.
Communication dated Jan. 12, 2015, issued by the United States Patent and Trademark Office in corresponding U.S. Appl. No. 14/143,289.
Communication dated Jan. 23, 2015, issued by the European Patent Office in counterpart Application No. 12802046.8.
Communication dated Sep. 5, 2014 from the USPTO in U.S. Appl. No. 14/143,289.
Communication dated Oct. 24, 2014 from the USPTO in U.S. Appl. No. 12/650,121.
Communication dated Aug. 29, 2014 from the USPTO in U.S. Appl. No. 14/098,140.
Communication dated Nov. 7, 2014 from the USPTO in U.S. Appl. No. 14/096,968.
Communication dated Sep. 5, 2014 from the USPTO in U.S. Appl. No. 14/143,430.
Communication dated Sep. 11, 2014 from the USPTO in U.S. Appl. No. 12/650,152.
Communication dated Oct. 15, 2014 from the USPTO in U.S. Appl. No. 12/781,366.
Communication dated Oct. 8, 2014 from the USPTO in U.S. Appl. No. 14/098,093.
Communication dated Oct. 14, 2014 from the USPTO in U.S. Appl. No. 12/075,252.
An Official Action dated Mar. 16, 2015 which issued during the prosecution of Applicant's U.S. Appl. No. 13/228,211.
An Official Action dated Mar. 25, 2015, which issued during the prosecution of Applicant's U.S. Appl. No. 12/075,252.
An Official Action dated Apr. 10, 2015 which issued during the prosecution of Applicant's U.S. Appl. No. 12/648,913.
An Official Action dated Apr. 10, 2015 which issued during the prosecution of Applicant's U.S. Appl. No. 12/650,152.
An Official Action dated Apr. 13, 2015 which issued during the prosecution of Applicant's U.S. Appl. No. 12/649,944.
An Official Action dated Mar. 16, 2015 which issued during the prosecution of Applicant's U.S. Appl. No. 13/228,185.
An Official Action dated Mar. 23, 2015 which issued during the prosecution of Applicant's U.S. Appl. No. 14/097,922.
An Official Action dated Feb. 23, 2015 which issued during the prosecution of Applicant's U.S. Appl. No. 14/143,184.
An Official Action dated May 6, 2015 which issued during the prosecution of Applicant's U.S. Appl. No. 12/781,260.
An Official Action dated May 11, 2015 which issued during the prosecution of Applicant's U.S. Appl. No. 12/650,605.
An English translation of an Official Action dated May 12, 2015 which issued during the prosecution of Applicant's Japanese Patent Application No. 521284/2013, and which is attached hereto.
An Official Action dated Aug. 17, 2015, which issued during the prosecution of Applicant's U.S. Appl. No. 12/648,913.
An Official Action dated Aug. 27, 2015, which issued during the prosecution of Applicant's U.S. Appl. No. 12/650,121.
An Official Action dated Oct. 22, 2015, which issued during the prosecution of Applicant's U.S. Appl. No. 12/649,944.

(56) References Cited

OTHER PUBLICATIONS

An Official Action dated Sep. 11, 2015, which issued during the prosecution of Applicant's U.S. Appl. No. 12/781,260.
An Official Action dated Sep. 3, 2015, which issued during the prosecution of Applicant's U.S. Appl. No. 13/228,211.
An Official Action dated Oct. 7, 2015, which issued during the prosecution of Applicant's U.S. Appl. No. 13/228,185.
An Official Action dated Aug. 11, 2015, which issued during the prosecution of Applicant's U.S. Appl. No. 13/228,335.
An Official Action dated Aug. 12, 2015, which issued during the prosecution of Applicant's U.S. Appl. No. 14/097,922.
An Official Action dated Aug. 25, 2015, which issued during the prosecution of Applicant's U.S. Appl. No. 14/143,184.
An Official Action dated Sep. 23, 2015, which issued during the prosecution of Applicant's U.S. Appl. No. 14/742,996.
An EP report dated Sep. 8, 2015, which issued during the prosecution of Applicant's EP Application No. 08719941.0.
An Official Action dated Sep. 4, 2015, which issued during the prosecution of Applicant's Canadian Application No. 2,874,415.
An international Search Report and WO dated Aug. 25, 2015, which issued during prosecution of Applicant's PCT/IL2015/050372.
An Official Action dated Sep. 21, 2015, which issued during the prosecution of Applicant's U.S. Appl. No. 13/228,229.
An Official Action dated Nov. 19, 2015, which issued during the prosecution of Applicant's U.S. Appl. No. 12/075,252.
An Official Action dated Dec. 31, 2015, which issued during the prosecution of Applicant's U.S. Appl. No. 12/648,913.
An Official Action dated Dec. 31, 2015, which issued during the prosecution of Applicant's U.S. Appl. No. 12/650,152.
An Official Action dated Jan. 21, 2016, which issued during the prosecution of Applicant's U.S. Appl. No. 13/228,335.
An Official Action dated Dec. 15, 2015, which issued during the prosecution of Applicant's U.S. Appl. No. 14/097,922.
An Official Action dated Dec. 22, 2015, which issued during the prosecution of Applicant's U.S. Appl. No. 14/142,172.
An Official Action dated Dec. 16, 2015, which issued during the prosecution of Applicant's U.S. Appl. No. 14/109,058.
An Official Action dated Dec. 3, 2015, which issued during the prosecution of Applicant's U.S. Appl. No. 14/143,184.
An Official Action dated Jan. 4, 2016, which issued during the prosecution of Applicant's U.S. Appl. No. 14/143,209.
An EP report dated Dec. 21, 2015, which issued during the prosecution of Applicant's EP Application No. 13793140.8.
An EP report dated Jan. 28, 2016, which issued during prosecution of Applicant's EP Application No. 13809066.7.
An Official Action dated May 5, 2016, which issued during the prosecution of Applicant's U.S. Appl. No. 12/648,913.
An Official Action dated May 5, 2016, which issued during the prosecution of Applicant's U.S. Appl. No. 14/097,922.
An Official Action dated May 4, 2016, which issued during the prosecution of Applicant's U.S. Appl. No. 14/109,058.
An Official Action dated Apr. 25, 2016, which issued during the prosecution of Applicant's U.S. Appl. No. 14/098,140.
An Official Action dated Apr. 20, 2016, which issued during the prosecution of Applicant's U.S. Appl. No. 12/649,955.
An Official Action dated Mar. 11, 2016, which issued during the prosecution of Applicant's U.S. Appl. No. 12/650,605.
An Official Action dated Mar. 16, 2016, which issued during the prosecution of Applicant's U.S. Appl. No. 13/228,211.
An Official Action dated Mar. 29, 2016, which issued during the prosecution of Applicant's U.S. Appl. No. 13/228,185.
An Official Action dated Feb. 19, 2016, which issued during the prosecution of Applicant's U.S. Appl. No. 14/145,612.
An Official Action dated Apr. 26, 2016, which issued during the prosecution of Applicant's U.S. Appl. No. 14/742,750.
An Official Action dated May 19, 2016, which issued during the prosecution of Applicant's U.S. Appl. No. 14/142,172.
An International Search Report and Written Opinion dated Oct. 5, 2015, which issued during prosecution of Applicant's PCT/IL2015/050509.
Communication dated May 21, 2015 from the United States Patent and Trademark Office in counterpart U.S. Appl. No. 14/098,140.
Communication dated Jul. 6, 2015 from the United States Patent and Trademark Office in counterpart U.S. Appl. No. 12/649,955.
Communication dated May 21, 2015 from the Canadian Intellectual Property Office in counterpart application No. 2,874,415.
Communication dated Jun. 23, 2015 from the Japanese Patent Office in counterpart application No. 2014-164417.
Communication dated May 19, 2015 from the United States Patent and Trademark Office in counterpart U.S. Appl. No. 13/228,229.
Communication dated Aug. 4, 2015 from the United States Patent and Trademark Office in counterpart U.S. Appl. No. 14/128,243.
Communication dated Jul. 28, 2015 from the United States Patent and Trademark Office in counterpart U.S. Appl. No. 12/075,252.
Communication dated Jul. 2, 2015 from the Canadian Intellectual Property Office in counterpart application No. 2,875,346.

* cited by examiner

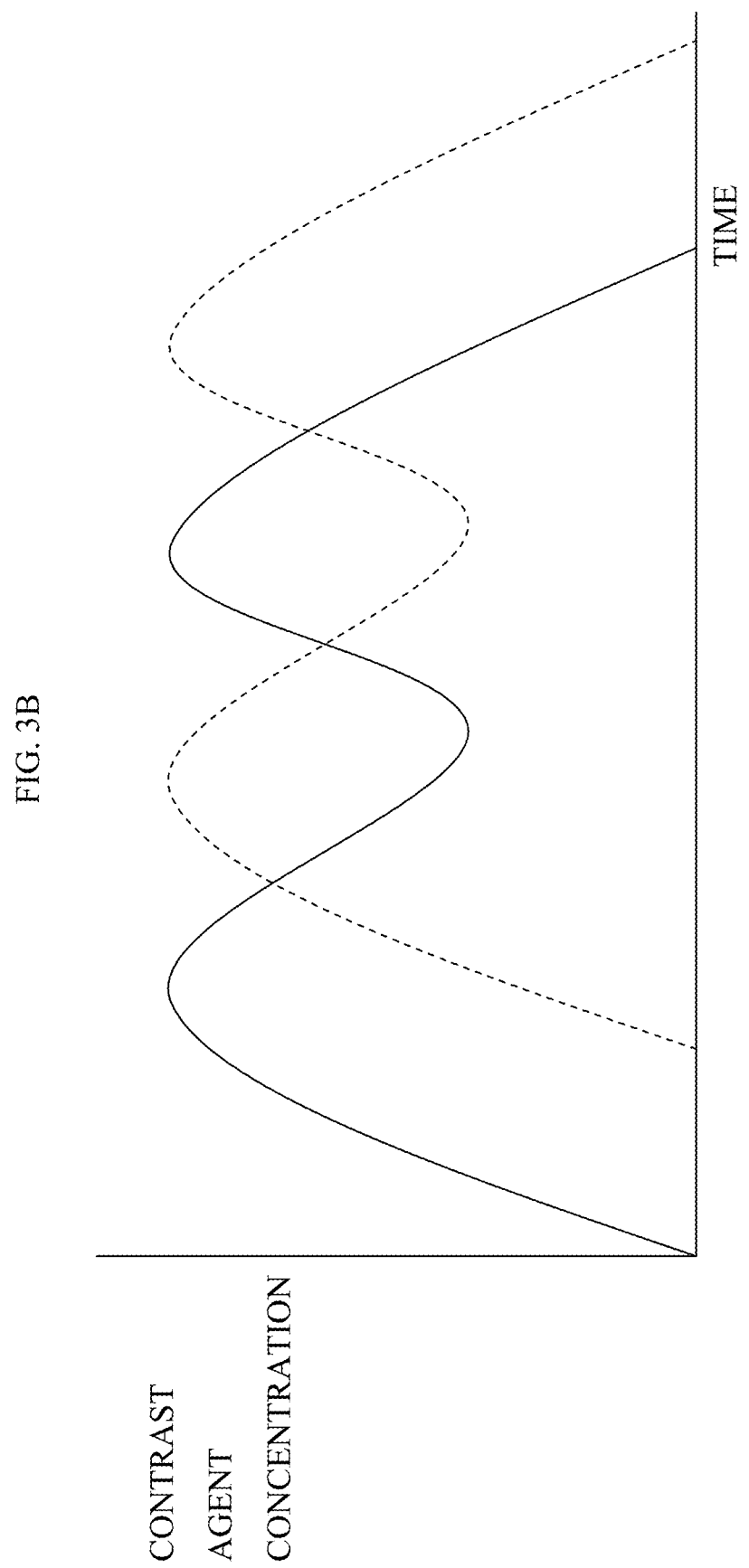

DETERMINING A CHARACTERISTIC OF A LUMEN BY MEASURING VELOCITY OF A CONTRAST AGENT

CROSS REFERENCES TO RELATED APPLICATIONS

The present application is:

(i) a continuation of PCT Application no. PCT/IL2013/050549 to Tolkowsky (published as WO 14/002095), filed Jun. 26, 2013, which claims the benefit of:

U.S. Provisional Patent Application 61/690,393, entitled "Flow-related image processing in luminal organs," filed Jun. 26, 2012;

U.S. Provisional Patent Application 61/741,105, entitled "Flow-related image processing in luminal organs," filed Jul. 12, 2012;

U.S. Provisional Patent Application 61/692,280, entitled "Flow-related image processing in luminal organs," filed Aug. 23, 2012; and U.S. Provisional Patent Application 61/704,570, entitled "Flow-related image processing in luminal organs," filed Sep. 24, 2012; and (ii) a continuation-in-part of U.S. patent application Ser. No. 12/075,244 to Tolkowsky (published as 2008/0221442, now abandoned), filed Mar. 10, 2008, entitled "Imaging for use with moving organs," which claims the benefit of U.S. Provisional Patent Application Nos.:

60/906,091 filed on Mar. 8, 2007;
60/924,609 filed on May 22, 2007;
60/929,165 filed on Jun. 15, 2007;
60/935,914 filed on Sep. 6 2007; and
60/996,746 filed on Dec. 4, 2007, all entitled "Apparatuses and methods for performing medical procedures on cyclically-moving body organs."

The present application is related to the following patent applications:

International Patent Application PCT/IL2013/050438 (published as WO 13/175472), entitled "Co-use of endoluminal data and extraluminal imaging," filed May 21, 2013;

International Patent Application PCT/IL2012/000246 (published as WO 12/176191), entitled "Luminal background cleaning," filed Jun. 21, 2012;

International Patent Application PCT/IL2011/000612 (published as WO 12/014212), entitled "Co-use of endoluminal data and extraluminal imaging," filed Jul. 28, 2011;

U.S. patent application Ser. No. 13/228,229 (published as US 2012/0004537), entitled "Co-use of endoluminal data and extraluminal imaging," filed Sep. 8, 2011;

International Patent Application PCT/IL2011/000391 (published as WO 11/145094), entitled "Identification and presentation of device-to-vessel relative motion," filed May 17, 2011;

U.S. patent application Ser. No. 12/781,260 to Blank (published as US 2010/0228076, now abandoned), entitled "Controlled actuation and deployment of a medical device," filed May 17, 2010;

U.S. patent application Ser. No. 12/650,605 to Cohen (published as US 2010/0172556), entitled "Automatic enhancement of an image stream of a moving organ," filed Dec. 31, 2009;

International Patent Application No. PCT/IL2009/001089 (published as WO 10/058398), entitled "Image processing and tool actuation for medical procedures," filed Nov. 18, 2009; and U.S. patent application Ser. No. 12/487,315 to Iddan (issued as U.S. Pat. No. 8,700,130), entitled "Stepwise advancement of a medical tool," filed Jun. 18, 2009.

All of the aforementioned references are incorporated herein by reference.

FIELD OF EMBODIMENTS OF THE INVENTION

Some applications of the present invention generally relate to medical imaging. Specifically, some applications of the present invention relate to determining a luminal-flow-related index, such as fractional flow reserve (FFR), based upon medical imaging.

BACKGROUND

Fractional flow reserve (FFR) is physiological index that measures the functional severity of a coronary artery stenosis (i.e., a narrowing, and/or an occlusion of the artery that is usually due to atherosclerosis). FFR measures the severity of the stenosis by determining the maximal blood flow through the artery in the presence of the stenosis relative to the hypothetical level of blood flow through the artery, if the artery were healthy. FFR provides an indication of the likelihood that the stenosis is impeding and/or will impede oxygen delivery to the heart muscle (i.e., the likelihood that the stenosis is causing and/or will cause myocardial ischemia). Other luminal-flow-related indices that are used to measure conditions of the coronary circulatory system include instantaneous wave-free ratio (iFR), coronary flow reserve (CFR), index of microcirculatory resistance (IMR), microvascular resistance index (MVRI), TIMI myocardial perfusion grade (TMPG), relative fractional flow reserve (RFFR), and other related (e.g., other statistically correlated) indices.

FFR is typically utilized in coronary catheterizations, and is typically calculated by measuring pressure differences across a coronary artery stenosis. Assuming that there is single stenosis, the relationship between the pressure downstream of the stenosis and the pressure upstream of the stenosis approximates the relationship between the flow of blood in the currently-stenosed coronary artery and the normal flow of blood had the artery been healthy. Thus, measuring pressure differences across a coronary artery stenosis provides an approximation of the FFR.

Typically, FFR serves as a decision support tool for determining whether the stenosis should be treated, such as by means of inflating a balloon and implanting a stent.

FFR is defined as the ratio between stenotic flow $Q_S$ and normal flow $Q_N$ under hyperemic conditions:

$$FFR = Q_S/Q_N$$

Using the flow equation $Q = \Delta P/R$, where Q is the flow (mL/min), $\Delta P$ is the pressure difference (mm Hg), and R is resistance (mmHg×min/mL), and the assumption that the venous pressure $P_{vein}$ is negligible, the FFR can be expressed as the ratio between distal pressure Pd to proximal pressure Pa of a stenosis:

$$FFR = (Q_S/Q_N) = ((P_d - P_{vein})/R)/((P_a - P_{vein})/R) = P_d/P_a$$

This pressure ratio can be written as follows:

$$FFR = P_d/P_a = (P_a - \Delta P_s)/P_a$$

where $\Delta P_s$ is the pressure drop along the axis of the lumen along a segment of the lumen from upstream of the stenosis to downstream of the stenosis.

The FFR result is an absolute number between zero and one; an FFR of 0.50 means that a given stenosis causes a 50% drop in blood pressure. In other words, FFR expresses the maximal flow through a lumen in the presence of a stenosis compared to the maximal flow in the hypothetical absence of the stenosis.

Typically, FFR is measured in coronary vessels by means of inserting into such vessels a wire equipped with sensors. The device analyzes pressure and flow parameters from inside of the vessel. Such wires are currently being produced by Volcano Corp. (San Diego, Calif.) and by St. Jude Medical (St. Paul, Minn.).

SUMMARY OF EMBODIMENTS

For some applications of the present invention, flow-related image processing is performed on luminal organs. Typically, a set of angiographic images of a lumen is acquired, and the geometry of the lumen at a given location within the lumen (typically, in a vicinity of a stenosis within the lumen) is determined automatically by performing image processing on at least one of the angiographic images. Blood velocity along the lumen is determined automatically, by performing image processing on at least two of the angiographic images. Typically, the geometry of the lumen and the blood velocity are determined without generating a three dimensional model of the lumen. For some applications, the geometry of the lumen and the blood velocity are determined solely by performing image-processing on two-dimensional angiographic images of the lumen. Based upon the geometry of the lumen and the blood velocity, the value of a current flow-related parameter of the lumen at the given location is determined. For example, the current flow, blood pressure, and/or blood velocity may be determined. An indication of a value of a second flow-related parameter of the subject is received. For example, an indication of blood pressure at an upstream location (e.g., aortic pressure) may be received. Alternatively or additionally, a historic angiographic image sequence that was acquired when the lumen was healthy may be received, and flow, blood pressure, and/or blood velocity within the lumen at the time when the lumen was healthy may be derived from the historic angiographic image sequence. A value of a luminal-flow-related index of the subject (such as the FFR of the subject) at the location is determined by determining a relationship between the value of the current flow-related parameter and the value of the second flow-related parameter.

For some applications, the value of a luminal-flow-related index of the subject is determined by (a) automatically determining pressure at a site based upon the automatically-determined lumen geometry and the automatically-determined blood velocity at the site, and (b) determining a relationship between the automatically-determined pressure at the site, and the subject's aortic pressure. An output is typically generated in response to the determined index at the site. For example, a stabilized image stream that is based upon the acquired angiographic images may be displayed, and, at a location within the image stream corresponding to the site, an indication of the index at the site may be displayed. For some applications, an indication of the value of the flow-related index is generated on an image of the lumen, using a color legend. Alternatively or additionally, in response to the luminal-flow-related index passing a first threshold value, an output is generated indicating that treatment of the subject is recommended, and in response to the luminal-flow-related index passing a second threshold value but not passing the first threshold value, an output is generated recommending that the luminal-flow-related index be measured using a sensor that is inserted into the lumen.

Typically, image processing described in the present application is performed intra-procedurally, though, for some applications, image processing is applied post-procedurally.

Although some applications of the present invention are described with reference to coronary catheterizations, the scope of the present invention includes applying the apparatus and methods described herein to other medical procedures and to other luminal organs in which there is a flow of fluid. For example, for some applications, the apparatus and methods described herein are applied, mutatis mutandis, to renal catheterization procedures, subclavian procedures, and/or below-the-knee procedures. For some such applications, determining a luminal-flow-related index using angiographic data facilitates determination of such an index, even in cases in which determination of the index via insertion of a wire would be physiologically difficult.

Although some applications of the present invention are described with reference to determining a subject's fractional flow reserve, the scope of the present invention includes applying the apparatus and methods described herein to determine other luminal-flow-related indices, including but not limited to instantaneous wave-free ratio (iFR), coronary flow reserve (CFR), index of microcirculatory resistance (IMR), microvascular resistance index (MVRI), TIMI myocardial perfusion grade (TMPG), relative fractional flow reserve (RFFR), and/or other related (e.g., other statistically correlated) indices.

It is noted that the terms "vessel" and "lumen" are used interchangeably in the present application. Both of the aforementioned terms should be construed to mean structures within the body that are shaped as lumens, for example, arteries and veins.

It is noted that the term "proximal" is used in the present application to denote a location within a lumen that is upstream of a given reference location (such as a stenosis) within the lumen, and the term "distal" is used to denote a location within a lumen that is downstream of a given reference location.

There is therefore provided, in accordance with some applications of the present invention, apparatus for use with an imaging device configured to acquire a set of angiographic images of a lumen of a subject's body, and a display, the apparatus including:

at least one processor, including:
blood-velocity-determination functionality configured, via image processing, to determine blood velocity within the lumen, by:
defining at least first and second regions of interest along the lumen in one of the angiographic images;
identifying the regions of interest in at least some additional angiographic images belonging to the set of angiographic images;
determining a distance between the regions of interest;
determining that a presence of a contrast agent appears at the first region of interest in a first one of the angiographic images and that the presence of contrast agent appears at the second region of interest in a second one of the angiographic images; and
determining the time that it took for the contrast agent to travel from the first region of interest to the second region of interest, based upon an interval between an acquisition of the first angiographic image and an acquisition of the second angiographic image;

geometry-indication-receiving functionality configured to receive an indication of geometry of the lumen at a given location within the lumen;

current-flow-related-parameter-determination functionality configured to determine a value of a current flow-related parameter at the location based upon the determined blood velocity and the geometry of the lumen in the vicinity of the location;

flow-related-parameter-receiving functionality configured to receive an indication of a value of a second flow-related parameter of the subject;

index-determination functionality configured to determine a value of a luminal-flow-related index of the subject at the location, by determining a relationship between the value of the current flow-related parameter and the value of the second flow-related parameter; and output-generation functionality configured to generate an output on the display in response to the determined value of the luminal-flow-related index.

For some applications, the given location includes a location in a vicinity of a stenosis within the lumen, and the index-determination functionality is configured to determine the value of the luminal-flow-related index of the subject at the location, by determining the value of the luminal-flow-related index in the vicinity of the stenosis.

For some applications, the index-determination functionality is configured to determine the value of the luminal-flow-related index of the subject at the location, by determining a value of functional flow reserve of the subject at the location.

For some applications, the index-determination functionality is configured to determine the value of the luminal-flow-related index of the subject at the location, by determining a value of instantaneous wave-free ratio of the subject at the location.

For some applications, the blood-velocity-determination functionality is configured to determine that the presence of the contrast agent appears at the first region of interest in the first one of the angiographic images and that the presence of contrast agent appears at the second region of interest in the second one of the angiographic images by determining that a given concentration of the contrast agent appears at the first region of interest in the first one of the angiographic images and that the given concentration of contrast agent appears at the second region of interest in the second one of the angiographic images.

For some applications, the blood-velocity-determination functionality is configured to determine that the presence of the contrast agent appears at the first region of interest in the first one of the angiographic images and that the presence of contrast agent appears at the second region of interest in the second one of the angiographic images by determining that a bolus of the contrast agent appears at the first region of interest in the first one of the angiographic images and that the bolus of contrast agent appears at the second region of interest in the second one of the angiographic images.

For some applications, the blood-velocity-determination functionality is configured to determine that the presence of the contrast agent appears at the first region of interest in the first one of the angiographic images and that the presence of contrast agent appears at the second region of interest in the second one of the angiographic images by determining that a given pattern of the contrast agent appears at the first region of interest in the first one of the angiographic images and that the given pattern of contrast agent appears at the second region of interest in the second one of the angiographic images.

For some applications, the blood-velocity-determination functionality is configured to define at least first and second regions of interest along the lumen in one of the angiographic images by defining at least first and second regions of interest along a center line of the lumen in one of the angiographic images.

For some applications, the at least one processor further includes image-stabilization functionality configured to generate a stabilized image stream of the lumen based upon the acquired angiographic images, and the output-generation functionality is configured to generate the output by driving the display to display the stabilized image stream, and by generating, at a location that corresponds to the location and that is within the displayed image stream, an indication of the value of the flow-related index at the location.

For some applications, the output-generation functionality is configured to generate the output by driving the display to display an indication of the value of the flow-related index, using a color legend, on an image of the lumen.

For some applications, the current-flow-related-parameter-determination functionality is configured to determine the value of the current flow-related parameter at the location using a machine-learning classifier, based upon at least the determined blood velocity and the geometry of the lumen at the location.

For some applications, the index-determination functionality is configured to determine the relationship between the value of the current flow-related parameter and the value of the second flow-related parameter by determining the relationship between the value of the current flow-related parameter and the value of the second flow-related parameter using a machine-learning classifier.

For some applications, the output-generation functionality is configured to generate the output by:

in response to the luminal-flow-related index passing a first threshold value, generating an output indicating that treatment of the subject is recommended; and in response to the luminal-flow-related index passing a second threshold value but not passing the first threshold value, generating an output recommending that the luminal-flow-related index be measured using a sensor that is inserted into the lumen.

For some applications:

the location includes a location in the vicinity of a stenosis;

the flow-related-parameter-receiving functionality is configured to receive the indication of the value of the second flow-related parameter of the subject by receiving an indication of a value of blood pressure of the subject at a location that is upstream of the stenosis;

the current-flow-related-parameter-determination functionality is configured to determine the value of the current flow-related parameter in the vicinity of the stenosis by determining a value of current blood pressure in the vicinity of the stenosis based upon the determined blood velocity and the geometry of the lumen in the vicinity of the stenosis; and the index-determination functionality is configured to determine the relationship between the value of the current flow-related parameter and the value of the second flow-related parameter by comparing the current blood pressure in the vicinity of the stenosis to the subject's blood pressure at the location that is upstream of the stenosis.

For some applications, the flow-related-parameter-receiving functionality is configured to receive the indication of the value of the blood pressure of the subject at the location that is upstream of the stenosis by receiving an indication of a value of aortic blood pressure of the subject.

For some applications, the flow-related-parameter-receiving functionality is configured to receive the indication of the value of the second flow-related parameter of the subject by receiving the indication of the value of the second flow-related parameter of the subject, based upon patient history of the subject.

For some applications:

the flow-related-parameter-receiving functionality is configured to receive the indication of the value of the second flow-related parameter of the subject by receiving at least one previously-acquired angiographic image of the subject's lumen, the flow-related-parameter-receiving functionality is further configured to derive a value of flow within the lumen at a time of acquisition of the previously-acquired angiographic image, the current-flow-related-parameter-determination functionality is configured to determine the value of the current flow-related parameter in the vicinity of the stenosis by determining a value of current flow at the location based upon the determined blood velocity and the geometry of the lumen at the location; and the index-determination functionality is configured to determine the relationship between the value of the current flow-related parameter and the value of the second flow-related parameter by determining a relationship between the value of the current flow at the location and the value of the derived flow within the lumen at the time of acquisition of the previously-acquired angiographic image.

For some applications:

the flow-related-parameter-receiving functionality is configured to receive the indication of the value of the second flow-related parameter of the subject by receiving at least one previously-acquired angiographic image of the subject's lumen, the flow-related-parameter-receiving functionality is further configured to derive a value of blood velocity within the lumen at a time of acquisition of the previously-acquired angiographic image, the current-flow-related-parameter-determination functionality is configured to determine the value of the current flow-related parameter in the vicinity of the stenosis by determining a value of current blood velocity at the location based upon the determined blood velocity and the geometry of the lumen at the location; and the index-determination functionality is configured to determine the relationship between the value of the current flow-related parameter and the value of the second flow-related parameter by determining a relationship between the value of the current blood velocity at the location and the value of the derived blood velocity within the lumen at the time of acquisition of the previously-acquired angiographic image.

For some applications, the geometry-indication-receiving functionality is configured to determine geometry of the lumen at the location, based upon the received indication of the geometry of the lumen.

For some applications, the current-flow-related-parameter-determination functionality is configured to determine the value of the current flow-related parameter at the location using a machine-learning classifier, based upon the determined lumen geometry and the determined blood velocity.

For some applications, the geometry-indication-receiving functionality is configured to:

receive the indication of the geometry of the lumen by receiving at least one of the set of angiographic images, and determine geometry of the lumen at the location by determining a cross-sectional area of the lumen by performing quantitative vessel analysis on the at least one of the set of angiographic images.

For some applications, the geometry-indication-receiving functionality is configured to:

receive the indication of the geometry of the lumen by receiving at least one of the set of angiographic images, and determine geometry of the lumen at the location by determining a cross-sectional area of the lumen by performing densitometry on the at least one of the set of angiographic images.

For some applications, the flow-related-parameter-receiving functionality is configured to receive the indication of a value of a second flow-related parameter of the subject by receiving an angiographic image of a second location within the lumen, and the flow-related-parameter-receiving functionality is configured to determine geometry of the lumen at the second location within the lumen, by performing image processing on the angiographic image of the second location within the lumen.

For some applications, the flow-related-parameter-receiving functionality is configured to determine geometry of the lumen at the second location within the lumen by determining a cross-sectional area at the second location within the lumen by performing quantitative vessel analysis on the angiographic image of the second location within the lumen.

For some applications, the flow-related-parameter-receiving functionality is configured to determine geometry of the lumen at the second location within the lumen by determining a cross-sectional area at the second location within the lumen by performing densitometry on the angiographic image of the second location within the lumen.

For some applications, the flow-related-parameter-receiving functionality is configured to determine a value of flow at the second location within the lumen based upon the determined geometry at the second location within the lumen and the determined blood velocity.

For some applications, the flow-related-parameter-receiving functionality is configured to determine the value of the flow at the second location within the lumen based upon the determined geometry at the second location within the lumen and the determined blood velocity, using a machine-learning classifier.

There is further provided, in accordance with some applications of the present invention, a method for use with a set of angiographic images of a lumen of a subject's body, the method including:

via image processing, determining blood velocity within the lumen, by:

defining at least first and second regions of interest along the lumen in one of the angiographic images;

identifying the regions of interest in at least some additional angiographic images belonging to the set of angiographic images;

determining a distance between the regions of interest;

determining that a presence of a contrast agent appears at the first region of interest in a first one of the angiographic images and that the presence of contrast agent appears at the second region of interest in a second one of the angiographic images; and determining the time that it took for the contrast agent to travel from the first region of interest to the second region of interest, based upon an interval between an acquisition of the first angiographic image and an acquisition of the second angiographic image;

receiving an indication of geometry of the lumen at a given location within the lumen;

determining a value of a current flow-related parameter at the location based upon the determined blood velocity and the geometry of the lumen in the vicinity of the location;

receiving an indication of a value of a second flow-related parameter of the subject;

determining a value of a luminal-flow-related index of the subject at the location, by determining a relationship between the value of the current flow-related parameter and the value of the second flow-related parameter; and generating an output in response to the determined value of the luminal-flow-related index.

For some applications, the contrast agent is within the lumen due to an injection of contrast agent into the lumen, and the method further includes acquiring a plurality of endoluminal images of the lumen, the acquisition of the plurality of endoluminal images being facilitated by the injection of the contrast agent.

There is further provided, in accordance with some applications of the present invention, apparatus for use with an imaging device configured to acquire a set of angiographic images of a lumen of a subject's body, and a display, the apparatus including:

at least one processor including:

image-processing functionality configured to analyze temporal changes in a density of a contrast agent at a given location within the lumen;

lumen-characterization functionality configured, in response to the analysis, to determine a characteristic of the lumen at the location, the characteristic being selected from the group consisting of: a presence of a stenosis in a vicinity of the location, and a value of a luminal-flow-related index of the subject at the location; and output-generation functionality configured to generate an output on the display in response to the determined characteristic of the lumen.

For some applications, the lumen-characterization functionality is configured to determine the characteristic of the lumen at the location, using a machine learning classifier.

For some applications, the at least one processor further includes geometry-indication-receiving functionality configured to determine geometry of the lumen at the location, and the lumen-characterization functionality is configured to determine the characteristic of the lumen at the location by determining the characteristic of the lumen at the location in response to the geometry of the vessel at the location and the analysis of the temporal changes in the density of the contrast agent at the location.

For some applications, the lumen-characterization functionality is configured to determine the characteristic of the lumen at the location by determining the value of the luminal-flow-related index of the subject at the location.

For some applications, the lumen-characterization functionality is configured to determine the characteristic of the lumen at the location by determining the presence of the stenosis in the vicinity of the location.

For some applications, the contrast agent includes contrast agent that is administered to the subject's lumen according to a given protocol, and the lumen-characterization functionality is configured to determine the characteristic of the lumen at the location by determining the characteristic of the lumen at the location based upon the temporal changes in the density of the contrast agent at the given location within the lumen and the given protocol.

For some applications, the lumen-characterization functionality is configured to determine the characteristic of the lumen at the location, using a machine learning classifier.

For some applications, the contrast agent includes contrast agent that is administered to the subject's lumen according to a given time-density protocol, and the lumen-characterization functionality is configured to determine the characteristic of the lumen at the location by comparing the temporal changes in the density of the contrast agent at the given location within the lumen to the time-density protocol according to which the contrast agent was administered to the subject.

There is further provided, in accordance with some applications of the present invention, a method for use with a set of angiographic images of a lumen of a subject's body, the method including:

via image processing, analyzing temporal changes in a density of a contrast agent at a given location within the lumen;

in response to the analysis, determining a characteristic of the lumen at the location, the characteristic being selected from the group consisting of: a presence of a stenosis in a vicinity of the location, and a value of a luminal-flow-related index of the subject at the location; and in response thereto, generating an output.

For some applications, the contrast agent includes contrast agent that is injected into the lumen, and the method further includes acquiring a plurality of endoluminal images of the lumen, the acquisition of the plurality of endoluminal images being facilitated by the injection of the contrast agent.

There is further provided, in accordance with some applications of the present invention, apparatus for use with an imaging device configured to acquire a set of two-dimensional angiographic images of a lumen of a subject's body, and a display, the apparatus including:

at least one processor, including:

blood-velocity-determination functionality configured, without generating a virtual three-dimensional model of the lumen, and by performing image processing on the two-dimensional angiographic images, to determine blood velocity within the lumen;

geometry-indication-receiving functionality configured, without generating a virtual three-dimensional model of the lumen, and by performing image processing on the two-dimensional angiographic images, to determine geometry of the lumen at a given location within the lumen;

current-flow-related-parameter-determination functionality configured to determine a value of a current flow-related parameter at the location based upon the determined blood velocity and the geometry of the lumen in the vicinity of the location;

flow-related-parameter-receiving functionality configured to receive an indication of a value of a second flow-related parameter of the subject;

index-determination functionality configured to determine a value of a luminal-flow-related index of the subject at the location, by determining a relationship between the value of the current flow-related parameter and the value of the second flow-related parameter; and output-generation functionality configured to generate an output on the display in response to the determined value of the luminal-flow-related index.

For some applications, the blood-velocity-determination functionality is configured to determine the blood velocity within the lumen by:

defining at least first and second regions of interest along the lumen in one of the angiographic images;

identifying the regions of interest in at least some additional angiographic images belonging to the set of angiographic images;

determining a distance between the regions of interest;

determining that a presence of a contrast agent appears at the first region of interest in a first one of the angiographic images and that the presence of contrast agent appears at the second region of interest in a second one of the angiographic images; and determining the time that it took for the contrast agent to travel from the first region of interest to the second region of interest, based upon an interval between an acquisition of the first angiographic image and an acquisition of the second angiographic image.

For some applications, the given location includes a location in a vicinity of a stenosis within the lumen, and the index-determination functionality is configured to determine the value of the luminal-flow-related index of the subject at the location, by determining the value of the luminal-flow-related index in the vicinity of the stenosis.

For some applications, the index-determination functionality is configured to determine the value of the luminal-flow-related index of the subject at the location, by determining a value of functional flow reserve of the subject at the location.

For some applications, the index-determination functionality is configured to determine the value of the luminal-flow-related index of the subject at the location, by determining a value of instantaneous wave-free ratio of the subject at the location.

For some applications, the at least one processor further includes image-stabilization functionality configured to generate a stabilized image stream of the lumen based upon the acquired angiographic images, and the output-generation functionality is configured to generate the output by driving the display to display the stabilized image stream, and by generating, at a location that corresponds to the location and that is within the displayed image stream, an indication of the value of the flow-related index at the location.

For some applications, the output-generation functionality is configured to generate the output by driving the display to display an indication of the value of the flow-related index, using a color legend, on an image of the lumen.

For some applications, the current-flow-related-parameter-determination functionality is configured to determine the value of the current flow-related parameter at the location based upon at least the determined blood velocity and the geometry of the lumen at the location, using a machine-learning classifier.

For some applications, the index-determination functionality is configured to determine the relationship between the value of the current flow-related parameter and the value of the second flow-related parameter by determining the relationship between the value of the current flow-related parameter and the value of the second flow-related parameter using a machine-learning classifier.

For some applications, the output-generation functionality is configured to generate the output by:

in response to the luminal-flow-related index passing a first threshold value, generating an output indicating that treatment of the subject is recommended; and in response to the luminal-flow-related index passing a second threshold value but not passing the first threshold value, generating an output recommending that the luminal-flow-related index be measured using a sensor that is inserted into the lumen.

For some applications, the geometry-indication-receiving functionality is configured to determine the geometry of the lumen at the given location within the lumen determining a cross-sectional area of the lumen by performing quantitative vessel analysis on at least one of the set of angiographic images.

For some applications, the geometry-indication-receiving functionality is configured to determine the geometry of the lumen at the given location within the lumen by performing densitometry on at least one of the set of angiographic images.

For some applications:

the location includes a location in the vicinity of a stenosis;

the flow-related-parameter-receiving functionality is configured to receive the indication of the value of the second flow-related parameter of the subject by receiving an indication of a value of blood pressure of the subject at a location that is upstream of the stenosis;

the current-flow-related-parameter-determination functionality is configured to determine the value of the current flow-related parameter in the vicinity of the stenosis by determining a value of current blood pressure in the vicinity of the stenosis based upon the determined blood velocity and the geometry of the lumen in the vicinity of the stenosis; and the index-determination functionality is configured to determine the relationship between the value of the current flow-related parameter and the value of the second flow-related parameter by comparing the current blood pressure in the vicinity of the stenosis to the subject's blood pressure at the location that is upstream of the stenosis.

For some applications, the flow-related-parameter-receiving functionality is configured to receive the indication of the value of the blood pressure of the subject at the location that is upstream of the stenosis by receiving an indication of a value of aortic blood pressure of the subject.

For some applications, the flow-related-parameter-receiving functionality is configured to receive the indication of the value of the second flow-related parameter of the subject by receiving the indication of the value of the second flow-related parameter of the subject, based upon patient history of the subject.

For some applications:

the flow-related-parameter-receiving functionality is configured to receive the indication of the value of the second flow-related parameter of the subject by receiving at least one previously-acquired angiographic image of the subject's lumen, the flow-related-parameter-receiving functionality is further configured to derive a value of flow within the lumen at a time of acquisition of the previously-acquired angiographic image, the current-flow-related-parameter-determination functionality is configured to determine the value of the current flow-related parameter in the vicinity of the stenosis by determining a value of current flow at the location based upon the determined blood velocity and the geometry of the lumen at the location; and the index-determination functionality is configured to determine the relationship between the value of the current flow-related parameter and the value of the second flow-related parameter by determining a relationship between the value of the current flow at the location and the value of the derived flow within the lumen at the time of acquisition of the previously-acquired angiographic image.

For some applications:

the flow-related-parameter-receiving functionality is configured to receive the indication of the value of the second flow-related parameter of the subject by receiving at least one previously-acquired angiographic image of the subject's lumen, the flow-related-parameter-receiving functionality is further configured to derive a value of blood velocity within the lumen at a time of acquisition of the previously-acquired angiographic image, the current-flow-related-parameter-determination functionality is configured to determine the value of the current flow-related parameter in the vicinity of the stenosis by determining a value of current blood velocity at the location based upon the determined blood velocity and the geometry of the lumen at the location; and the index-determination functionality is configured to determine the relationship between the value of the current flow-related parameter and the value of the second flow-related parameter by determining a relationship between the value of the current blood velocity at the location and the value of the derived blood velocity within the lumen at the time of acquisition of the previously-acquired angiographic image.

For some applications, the flow-related-parameter-receiving functionality is configured to receive the indication of a value of a second flow-related parameter of the subject by receiving an angiographic image of a second location within the lumen, and the flow-related-parameter-receiving functionality is configured to determine geometry of the lumen at the second location within the lumen, by performing image processing on the angiographic image of the second location within the lumen.

For some applications, the flow-related-parameter-receiving functionality is configured to determine geometry of the lumen at the second location within the lumen by determining a cross-sectional area at the second location within the lumen by performing quantitative vessel analysis on the angiographic image of the second location within the lumen.

For some applications, the flow-related-parameter-receiving functionality is configured to determine geometry of the lumen at the second location within the lumen by determining a cross-sectional area at the second location within the lumen by performing densitometry on the angiographic image of the second location within the lumen.

For some applications, the flow-related-parameter-receiving functionality is configured to determine a value of flow at the second location within the lumen based upon the determined geometry at the second location within the lumen and the determined blood velocity.

For some applications, the flow-related-parameter-receiving functionality is configured to determine the value of the flow at the second location within the lumen based upon the determined geometry at the second location within the lumen and the determined blood velocity, using a machine-learning classifier.

There is further provided, in accordance with some applications of the present invention, a method for use with a set of two-dimensional angiographic images of a lumen of a subject's body, the method including:

without generating a virtual three-dimensional model of the lumen, and by performing image processing on the two-dimensional angiographic images:

determining blood velocity within the lumen; and determining geometry of the lumen at a given location within the lumen;

determining a value of a current flow-related parameter at the location based upon the determined blood velocity and the geometry of the lumen at the location;

receiving an indication of a value of a second flow-related parameter of the subject;

determining a value of a luminal-flow-related index of the subject at the location, by determining a relationship between the value of the current flow-related parameter and the value of the second flow-related parameter; and generating an output in response to the determined value of the luminal-flow-related index.

There is further provided, in accordance with some applications of the present invention, apparatus for use with a lumen of a subject, including:

a pressure sensor configured to measure pressure of the lumen;

a blood velocity sensor configured to measure blood velocity within the lumen; and at least one processor including:

lumen-dimension-derivation functionality configured to derive a dimension of the lumen from the measured pressure and blood velocity; and output-generation functionality configured to generate an out output in response to the derived dimension.

For some applications, the apparatus further includes a tool configured to be inserted into the lumen, and the pressure sensor and the blood velocity sensor are both coupled to the tool.

For some applications, the lumen-dimension-derivation functionality is configured to derive the dimension of the lumen by deriving a length of a portion of the lumen.

For some applications, the lumen-dimension-derivation functionality is configured to derive the dimension of the lumen by deriving a cross-sectional area of the lumen.

For some applications, the lumen-dimension-derivation functionality is configured to derive the dimension of the lumen by deriving a percentage occlusion of the lumen.

For some applications, the lumen-dimension-derivation functionality is configured to derive the dimension of the lumen by deriving a diameter of the lumen.

For some applications, the lumen-dimension-derivation functionality is configured to derive the diameter of the lumen by deriving a minimum lumen diameter of the lumen.

There is further provided, in accordance with some applications of the present invention, a method for use with a lumen of a subject, including:

measuring pressure of the lumen;

measuring blood velocity within the lumen;

deriving from the measured pressure and blood velocity, a dimension of the lumen; and generating an output in response thereto.

For some applications, measuring pressure of the lumen includes measuring pressure of the lumen using a pressure sensor that is coupled to a medical device while the medical device is inside the lumen, and measuring blood velocity includes measuring blood velocity using a blood velocity sensor that is coupled to the medical device while the medical device is inside the lumen.

There is further provided, in accordance with some applications of the present invention, apparatus for use with (a) an endoluminal data-acquisition device configured to be moved through a lumen of a subject's body, and to acquire at least a first set of endoluminal data points of the lumen at a plurality of locations within the lumen, while being moved through the lumen, (b) and extraluminal imaging device configured to acquire an extraluminal image of the lumen, and (c) a display, the apparatus including:

at least one processor, including:

endoluminal-geometry-derivation-functionality configured, for at least some of the endoluminal data points, to derive from the endoluminal data point a value of a geometrical parameter of the lumen at a location within the lumen at which the endoluminal data point was acquired;

extraluminal-geometry-derivation-functionality configured to derive values of the geometrical parameter of the lumen at a plurality of locations along the lumen, by performing image processing on the at least one extraluminal image of the lumen;

co-registration functionality configured to co-register at least some of the endoluminal data points to locations along the lumen within the extraluminal image by correlating the values of the geometrical parameters corresponding to the endoluminal data points with the values of the geometrical parameter derived by performing image processing on the at least one extraluminal image; and output-generation functionality configured to generate an output on the display based upon the co-registration.

For some applications, the output-generation functionality is configured to generate the output by generating an output indicating that a given endoluminal data point corresponds to a given location along the lumen.

For some applications:

the endoluminal-geometry-derivation-functionality is configured to derive the value of the geometrical parameter of the lumen by deriving a value of a geometrical parameter of the lumen selected from the group consisting of: a cross-sectional area of the lumen, and a diameter of the lumen; and the extraluminal-geometry-derivation-functionality is configured to derive values of the geometrical parameter of the lumen, by deriving values of the selected geometrical parameter.

For some applications, the set of endoluminal data points includes a set of blood velocity data points that are indicative of blood velocity within the lumen at locations at which respective endoluminal data points belonging to the set of endoluminal data points were acquired, and the endoluminal-geometry-derivation-functionality is configured to derive from at least some of the blood velocity data points a value of a geometrical parameter of the lumen at a location within the lumen at which the blood velocity data point was acquired.

For some applications, the set of endoluminal data points includes a set of blood pressure data points that are indicative of blood pressure within the lumen at locations at which respective endoluminal data points belonging to the set of endoluminal data points were acquired, and the endoluminal-geometry-derivation-functionality is configured to derive from at least some of the blood pressure data points a value of a geometrical parameter of the lumen at a location within the lumen at which the blood pressure data point was acquired.

For some applications, the set of endoluminal data points includes a set of flow data points that are indicative of flow within the lumen at locations at which respective endoluminal data points belonging to the set of endoluminal data points were acquired, and the endoluminal-geometry-derivation-functionality is configured to derive from at least some of the flow data points a value of a geometrical parameter of the lumen at a location within the lumen at which the flow data point was acquired.

For some applications, the set of endoluminal data points includes a set of endoluminal images, and the endoluminal-geometry-derivation-functionality is configured to derive the value of the geometrical parameter of the lumen at the location within the lumen at which an endoluminal data point was acquired by deriving the value of the geometrical parameter of the lumen at the location within the lumen at which an endoluminal image was acquired by performing image processing on the endoluminal image.

For some applications:

the endoluminal data-acquisition device includes an endoluminal data-acquisition device that is further configured to acquire a second set of endoluminal data points of the lumen at a plurality of locations within the lumen, while being moved through the lumen;

the co-registration functionality is configured, based upon the co-registering of the first set of endoluminal data points to locations along the lumen within the extraluminal image, to co-register the second set of endoluminal data points to locations along the lumen within the extraluminal image; and the output-generation functionality is configured to generate the output by generating an output indicating that a given endoluminal data point belonging to the second set of endoluminal data points corresponds to a given location along the lumen.

For some applications:

the first set of endoluminal data points includes a set of blood velocity data points that are indicative of blood velocity within the lumen at locations at which respective endoluminal data points belonging to the set of endoluminal data points were acquired;

the endoluminal-geometry-derivation-functionality is configured to derive from at least some of the blood velocity data points a value of a geometrical parameter of the lumen at a location within the lumen at which the blood velocity data point was acquired;

the second set of endoluminal data points includes a set of endoluminal images; and the output-generation functionality is configured to generate the output by generating an output indicating that a given endoluminal image corresponds to a given location along the lumen.

For some applications:

the first set of endoluminal data points includes a set of blood velocity data points that are indicative of blood velocity within the lumen at locations at which respective endoluminal data points belonging to the set of endoluminal data points were acquired;

the endoluminal-geometry-derivation-functionality is configured to derive from at least some of the blood velocity data points a value of a geometrical parameter of the lumen at a location within the lumen at which the blood velocity data point was acquired;

the second set of endoluminal data points includes a set of endoluminal functional data points; and the output-generation functionality is configured to generate the output by generating an output indicating that a given endoluminal functional data point corresponds to a given location along the lumen.

For some applications, the co-registration functionality is configured to co-register at least some of the endoluminal data points to locations along the lumen within the extraluminal image by correlating a sequence of values of the geometrical parameters corresponding to the endoluminal data points with a sequence of values of the geometrical parameter derived by performing image processing on the at least one extraluminal image.

For some applications, the co-registration functionality is configured to co-register at least some of the endoluminal data points to locations along the lumen within the extraluminal image by correlating a variation of the sequence of values of the geometrical parameters corresponding to the endoluminal data points with a variation of the sequence of values of the geometrical parameter derived by performing image processing on the at least one extraluminal image.

For some applications, the co-registration functionality is configured to co-register at least some of the endoluminal data points to locations along the lumen within the extraluminal image by correlating a mathematical derivative of the sequence of values of the geometrical parameters corresponding to the endoluminal data points with a mathematical derivative of the sequence of values of the geometrical parameter derived by performing image processing on the at least one extraluminal image.

There is further provided, in accordance with some applications of the present invention, a method for use with an endoluminal data-acquisition device configured to be moved through a lumen of a subject's body, the method including:

while the endoluminal data-acquisition device is being moved through the lumen, acquiring at least a first set of endoluminal data points of the lumen at a plurality of locations within the lumen, using the endoluminal data-acquisition device;

for at least some of the endoluminal data points, deriving from the endoluminal data point a value of a geometrical parameter of the lumen at a location within the lumen at which the endoluminal data point was acquired;

acquiring at least one extraluminal image of the lumen;

deriving values of the geometrical parameter of the lumen at a plurality of locations along the lumen, by performing image processing on the at least one extraluminal image of the lumen;

co-registering at least some of the endoluminal data points to locations along the lumen within the extraluminal image by correlating the values of the geometrical parameters corresponding to the endoluminal data points with the values of the geometrical parameter derived by performing image processing on the at least one extraluminal image; and in response thereto, generating an output.

There is further provided, in accordance with some applications of the present invention, apparatus for use with (a) an endoluminal data-acquisition device configured to be moved through a lumen of a subject's body, and to acquire at least a first set of endoluminal data points of the lumen at a plurality of locations within the lumen, while being moved through the lumen, (b) an extraluminal imaging device configured to acquire at least one two-dimensional angiographic image of the lumen, and (c) a display, the apparatus including:

at least one processor including:
index-determination functionality configured to non-invasively determine a value of a luminal-flow-related index of the subject at a plurality of locations along the lumen, at least partially by performing image processing on the two-dimensional angiographic image;
co-registration functionality configured:
to determine that respective endoluminal data points correspond to respective locations along the lumen, and
in response thereto, to determine that respective endoluminal data points correspond to respective values of the luminal flow-related index; and
output-generation functionality configured to generate an output on the display based upon determining that respective endoluminal data points correspond to respective values of the luminal flow-related index.

For some applications, the index-determination functionality is configured to determine the value of the luminal-flow-related index of the subject at the plurality of locations along the lumen, by determining a value of functional flow reserve of the subject at the plurality of locations along the lumen.

For some applications, the index-determination functionality is configured to determine the value of the luminal-flow-related index of the subject at the plurality of locations along the lumen, by determining a value of instantaneous wave-free ratio of the subject at the plurality of locations along the lumen.

For some applications, the output-generation functionality is configured to generate the output by generating an output indicating that a given endoluminal data point corresponds to a given value of the luminal flow-related index.

For some applications, the set of endoluminal data points includes a set of endoluminal images, and the output-generation functionality is configured to generate the output by generating an output indicating that a given endoluminal image corresponds to a given value of the luminal flow-related index.

For some applications, the set of endoluminal data points includes a set of endoluminal functional data points, and the output-generation functionality is configured to generate the output by generating an output indicating that a given endoluminal functional data point corresponds to a given value of the luminal flow-related index.

There is further provided, in accordance with some applications of the present invention, a method for use with an endoluminal data-acquisition device configured to be moved through a lumen of a subject's body, and at least one two-dimensional angiographic image of the lumen, the method including:

non-invasively determining a value of a luminal-flow-related index of the subject at a plurality of locations along the lumen, at least partially by performing image processing on the at least one two-dimensional angiographic image;

while the endoluminal data-acquisition device is being moved through the lumen, acquiring a set of endoluminal data points of the lumen at a plurality of locations within the lumen, using the endoluminal data-acquisition device;

determining that respective endoluminal data points correspond to respective locations along the lumen;

in response thereto, determining that respective endoluminal data points correspond to respective values of the luminal flow-related index; and generating an output in response thereto.

There is further provided, in accordance with some applications of the present invention, apparatus for use with an imaging device configured to acquire a plurality of angiographic image frames of a moving lumen of a subject, and a display, the apparatus including:

at least one processor including:
blood-velocity-determination functionality configured to:
align the image frames with each other; and
using the aligned image frames, determine a time it takes a contrast agent to travel a known distance through the lumen;

lumen-characterization functionality configured at least partially in response to the determined time it takes the contrast agent to travel the known distance through the lumen, to determine a characteristic of the lumen; and output-generation functionality configured, in response to the determined characteristic, to generate an output on the display.

For some applications, the lumen-characterization functionality is configured to determine the characteristic of the lumen by determining flow within the lumen.

For some applications, the lumen-characterization functionality is configured to determine the characteristic of the lumen by determining a hemodynamic characteristic of the lumen.

For some applications, the lumen-characterization functionality is configured to determine the characteristic of the lumen by:

determining geometry of the lumen, and determining a value of a current flow-related parameter of the lumen based upon the time it takes the contrast agent to travel the known distance through the lumen and the determined geometry of the lumen.

For some applications:

the at least one processor further includes flow-related-parameter-receiving functionality configured to receive an indication of a value of a second flow-related parameter of the subject; and the lumen-characterization functionality is configured to determine the characteristic of the lumen by determining a value of a luminal-flow-related index of the subject at a given location within the lumen, by determining a relationship between the value of the current flow-related parameter and the value of the second flow-related parameter.

For some applications, the given location includes a location in a vicinity of a stenosis within the lumen, and the lumen-characterization functionality is configured to determine the value of the luminal-flow-related index by determining the value of the luminal-flow-related index in the vicinity of the stenosis.

For some applications, the lumen-characterization functionality is configured to determine the value of the luminal-flow-related index by determining a value of functional flow reserve of the subject at the location.

For some applications, the lumen-characterization functionality is configured to determine the value of the luminal-flow-related index by determining a value of instantaneous wave-free ratio of the subject at the location.

For some applications, the at least one processor is configured to generate a stabilized image stream of the lumen based upon the acquired angiographic images, and the output-generation functionality is configured to generate the output by driving the display to display the stabilized image stream, and by generating, at a location that corresponds to the location and that is within the displayed image stream, an indication of the value of the flow-related index at the location.

For some applications, the output-generation functionality is configured to generate the output by driving the display to display an indication of the value of the flow-related index, using a color legend, on an image of the lumen.

For some applications, the lumen-characterization functionality is configured to determine the value of the luminal-flow-related index based upon the determined blood velocity and geometry of the lumen at the location, using a machine-learning classifier.

For some applications, the lumen-characterization functionality is configured to determine the relationship between the value of the current flow-related parameter and the value of the second flow-related parameter using a machine-learning classifier.

For some applications, the output-generation functionality is configured to generate the output by:

in response to the luminal-flow-related index passing a first threshold value, generating an output indicating that treatment of the subject is recommended; and in response to the luminal-flow-related index passing a second threshold value but not passing the first threshold value, generating an output recommending that the luminal-flow-related index be measured using a sensor that is inserted into the lumen.

There is further provided, in accordance with some applications of the present invention, a method for use with a plurality of angiographic image frames of a moving lumen of a subject, the method including:

aligning the image frames with each other;

using the aligned image frames, determining a time it takes a contrast agent to travel a known distance through the lumen;

at least partially in response thereto, determining a characteristic of the lumen; and in response to the determined characteristic, generating an output on a display.

For some applications, determining the characteristic of the lumen includes determining flow within the lumen.

For some applications, determining the characteristic of the lumen includes determining a hemodynamic characteristic of the lumen.

For some applications, determining the characteristic of the lumen includes determining geometry of the lumen, and determining a value of a current flow-related parameter of the lumen based upon the time it takes the contrast agent to travel the known distance through the lumen and the determined geometry of the lumen.

For some applications, the method further includes:

receiving an indication of a value of a second flow-related parameter of the subject; and determining a value of a luminal-flow-related index of the subject at a given location within the lumen, by determining a relationship between the value of the current flow-related parameter and the value of the second flow-related parameter.

For some applications, the given location includes a location in a vicinity of a stenosis within the lumen, and determining the value of the luminal-flow-related index includes determining the value of the luminal-flow-related index in the vicinity of the stenosis.

For some applications, determining the value of the luminal-flow-related index at the location includes determining a value of functional flow reserve of the subject at the location.

For some applications, determining the value of the luminal-flow-related index of the subject at the location includes determining a value of instantaneous wave-free ratio of the subject at the location.

For some applications, the method further includes generating a stabilized image stream of the lumen based upon the aligned angiographic images, and generating the output includes generating an indication of the value of the flow-related index on the image stream.

For some applications, generating the output includes generating, on an image of the lumen, an indication of the value of the flow-related index, using a color legend.

For some applications, determining the value of the current flow-related parameter at the location within the lumen includes, using a machine-learning classifier, determining the value of the current flow-related parameter at the location within the lumen, based upon the determined blood velocity and geometry of the lumen at the location.

For some applications, determining the relationship between the value of the current flow-related parameter and the value of the second flow-related parameter includes determining the relationship between the value of the current flow-related parameter and the value of the second flow-related parameter using a machine-learning classifier.

For some applications, generating the output includes:

in response to the luminal-flow-related index passing a first threshold value, generating an output indicating that treatment of the subject is recommended; and in response to the luminal-flow-related index passing a second threshold value but not passing the first threshold value, generating an output recommending that the luminal-flow-related index be measured using a sensor that is inserted into the lumen.

The present invention will be more fully understood from the following detailed description of embodiments thereof, taken together with the drawings, in which:

BRIEF DESCRIPTION OF THE DRAWINGS

FIG. 3B shows an illustrative example of time-density curves of a contrast agent measured at respective regions within a lumen, in accordance with some applications of the present invention;

DETAILED DESCRIPTION OF EMBODIMENTS

The term "contrast agent," when used in reference to its application in conjunction with imaging, refers to any substance that is used to highlight, and/or enhance in another manner, the anatomical structure, functioning, and/or composition of a bodily organ while the organ is being imaged.

The term "stabilized," when used in the context of displayed images, means a display of a series of images in a manner such that periodic, cyclical, and/or other motion of the body organ(s) being imaged, and/or of a medical tool being observed, is partially or fully reduced, with respect to the entire image frame, or at least a portion thereof The term "automatic," when used for describing the generation and utilization of the road map, means "without necessitating user intervention or interaction." (Such interaction or intervention may still however be optional in some cases.)

The term "real time" means without a noticeable delay.

The term "near real time" means with a short noticeable delay (such as approximately one or two motion cycles of the applicable organ, and, in the case of procedures relating to organs or lumens the motion of which are primarily as a result of the cardiac cycle, less than two seconds).

The term "on-line," when used in reference to image processing, or to measurements being made on images, means that the image processing is performed, and/or the measurements are made, intra-procedurally, for example, in real time or near real time.

The term "luminal-flow-related index" includes fractional flow reserve (FFR), instantaneous wave-free ratio (iFR), coronary flow reserve (CFR), index of microcirculatory resistance (IMR), microvascular resistance index (MVRI), TIMI myocardial perfusion grade (TMPG), relative fractional flow reserve (RFFR), and/or other related indices (e.g., indices that are statistically correlated with one or more of the aforementioned indices).

Figure 1:
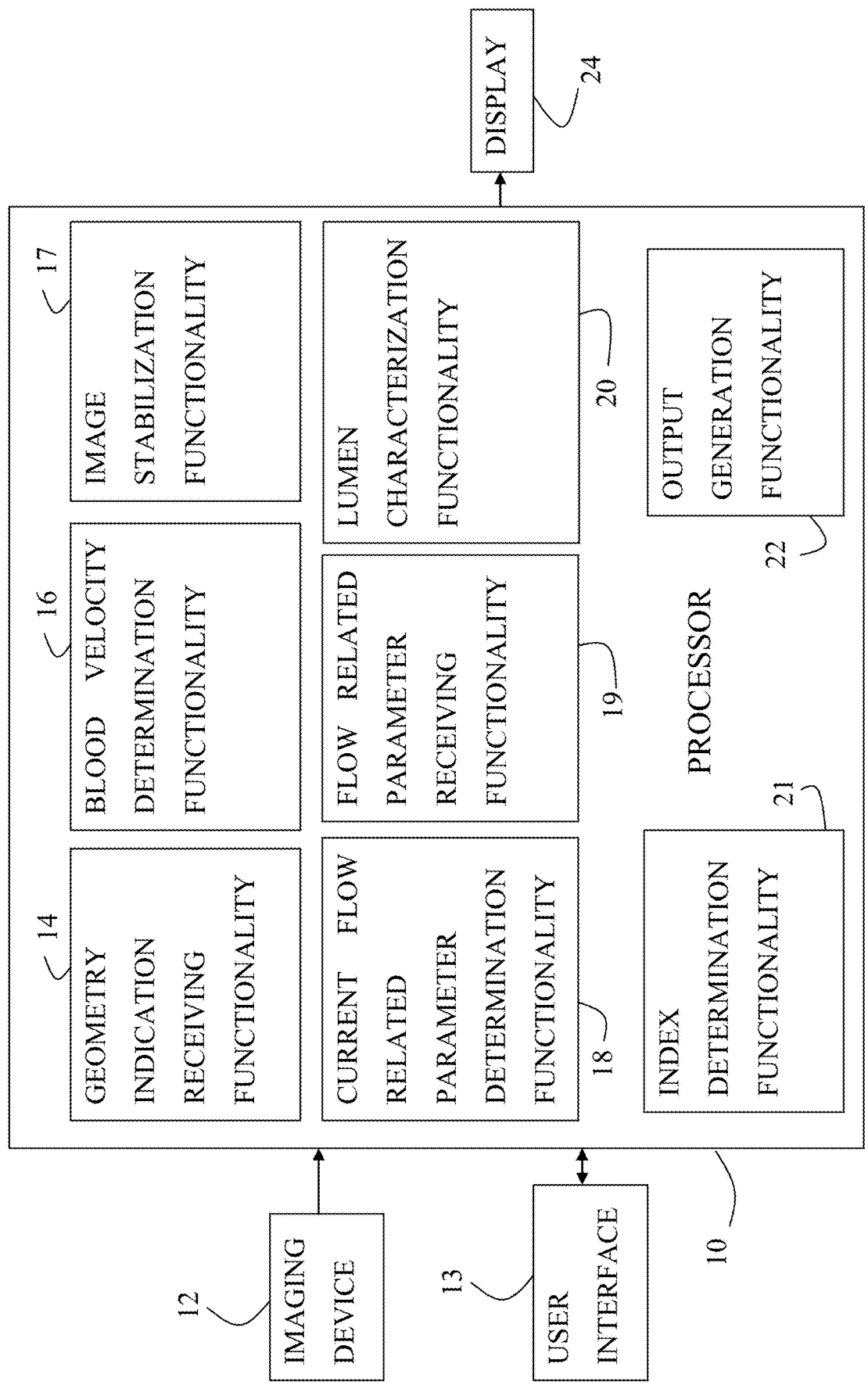
FIG. 1 is a schematic illustration of a processor that is used to calculate a luminal-flow-related index, by means of image processing, in accordance with some applications of the present invention.

Reference is now made to FIG. 1, which is a schematic illustration of a processor 10 that is used to calculate a luminal-flow-related index, by means of image processing, in accordance with some applications of the present invention. Typically the processor calculates the luminal-flow-related index at a location within a lumen (e.g., a location in the vicinity of a stenosis) of the subject based upon image processing of angiographic images of the lumen that are acquired by an imaging device 12. Processor 10 is typically used to perform the procedure described with respect to FIG. 2. Processor 10 typically receives inputs via the imaging device and via a user interface 13, and generates an output on display 24. For some applications, the user interface includes a keyboard, a mouse, a trackball, a joystick, a touchscreen monitor, a touchpad, a voice-command interface, and/or other types of user interfaces that are known in the art. Typically, the display includes a monitor. For some applications, the display includes a head-up display and/or a head-mounted display, such as Google Glass. Processor 10 typically includes at least some of the following functionalities, the functions of which are described in further detail hereinbelow: geometry-indication-receiving functionality 14, blood-velocity-determination functionality 16, image-stabilization functionality 17, current-flow-related-parameter-determination functionality 18, flow-related-parameter-receiving functionality 19, lumen-characterization functionality 20, index-determination functionality 21, and/or output-generation functionality 22. For some applications, more than one processor is used to perform the aforementioned functionalities. For some applications, the at least one processor performs only a portion of the aforementioned functionalities.

For some applications, processor 10 includes geometry-indication-receiving functionality 14 that receives an indication of the geometry of the lumen. Typically, the geometry-indication-receiving functionality receives at least one of the angiographic images, and automatically determines geometry of the lumen at a location within the lumen (e.g., in a vicinity of a stenosis within the lumen), by performing image processing on at least one of the angiographic images. For some applications, the aforementioned geometric measurements include quantitative vessel analysis, e.g., quantitative coronary analysis (QCA). For some applications, QCA is performed in an automated manner, typically on line, using techniques described in WO 10/058398 to Cohen, US 2010/0172556 to Cohen, and/or US 2010/0228076 to Blank, all of which applications are incorporated herein by reference. It is noted that, typically, geometry-indication-receiving functionality determines geometry of the lumen solely by performing image processing on two-dimensional angiographic images. Further typically, geometry-indication-receiving functionality determines geometry of the lumen without generating a three-dimensional model of the lumen.

For some applications, and typically in order to account for potential asymmetry in the geometry of the lumen around its longitudinal axis, angiographic images of the lumen are acquired from two or more different viewing angles, and the lumen geometry is determined based upon the two or more angiographic images (e.g., by performing QCA on the two or more angiographic images). Typically, in the case of angiographic images of the lumen being acquired from two or more different viewing angles, the viewing angles (or at least two of the viewing angles) form an angle with one another of at least thirty degrees. The resulting two or more measured diameters, or two or more sets of measured diameters, are used to calculate the cross-sectional area of the lumen (e.g., the cross-sectional area in the vicinity of the stenosis, and/or at other locations along the lumen (e.g., within a healthy portion of the lumen)). For some applications, and typically in order to facilitate measurements, a two-dimensional model is generated for one or more cross-sections of the lumen, and the lumen geometry is determined based upon the two-dimensional model. For some applications and typically in order to facilitate measurements, a three-dimensional model of a lumen section is generated, and the lumen geometry is determined based upon the three-dimensional model. For some applications, typically for the purpose of generating the two-dimensional or the three-dimensional model, the lumen is assumed to be symmetrical around its longitudinal axis. For some applications, typically in order to account for potential foreshortening of the lumen as viewed from a single specific angle, QCA is performed on angiographic images acquired from two or more different viewing angles, and the resulting two or more measured lengths, or two or more sets of length measurements, are used to calculate the length of the lumen.

For some applications, geometry-indication-receiving functionality 14 determines the cross-sectional area of the lumen in the vicinity of the stenosis, and/or at other locations along the lumen (e.g., within a healthy portion of the lumen) by performing densitometry on at least one of the angiographic images, in accordance with the techniques described hereinbelow.

Processor 10 typically includes blood-velocity-determination functionality 16 that automatically determines blood velocity within the lumen, by performing image processing on the angiographic image sequence. It is noted that, typically, blood-velocity-determination functionality 16 automatically determines blood velocity within the lumen solely by performing image processing on two-dimensional angiographic images. Further typically, blood-velocity-determination functionality 16 automatically determines blood velocity within the lumen without generating a three-dimensional model of the lumen.

For some applications, image-stabilization functionality 17 of processor 10 is configured to generate a stabilized image stream of the lumen. For some applications of the present invention, on-line geometric and/or hemodynamic measurements (e.g., size, flow, ejection fraction) are determined by the processor, for example, by utilizing the stabilized image stream, in accordance with techniques described in US 2008/0221442 to Tolkowsky, which is incorporated herein by reference. For some applications, the stabilized image stream is used for on-line measurement of the flow within a lumen, by measuring the time it takes contrast agent to travel a known distance, e.g., in accordance with techniques described in US 2008/0221442 to Tolkowsky, which is incorporated herein by reference.

For some applications, the aforementioned hemodynamic measurements include measuring the time it takes contrast agent to travel a known distance, i.e., measuring the velocity of the contrast agent, and thereby measuring the velocity of blood flow through the lumen (e.g., as described in further detail with reference to FIG. 2). For some applications, such measurements include, typically automatically, by means of image processing, measuring the movement and/or the concentration of contrast agent within the lumen. For some applications, such measurements include, typically automatically, by means of image processing, measuring the location and/or darkness of pixels corresponding to contrast agent within the lumen, which typically serves as a further indication of the quantity and/or the concentration of the contrast agent in the blood flow. For some applications, such measurements are performed, typically automatically, by means of image processing, proximally and/or distally to the stenosis.

For some applications, parameters associated with the injection of the contrast agent for the angiograms are known, which typically facilitates the aforementioned calculations. For example, the duration, quantity, concentration, pressure and/or flow of the contrast agent may be known. For some applications, the contrast agent is injected at a known pattern of known quantities and concentrations along a known time line, which typically facilitates the aforementioned calculations.

For some applications, the contrast agent is injected for the angiograms with an automated injection device such as the ACIST CVi® injection system manufactured by ACIST Medical Systems (Minnesota, USA). Typically, the use of such an automated device facilitates determination and control of some or all of the aforementioned parameters.

For some applications, the automated injection device is programmed to inject contrast agent such that the contrast agent replaces all the blood in the coronary blood vessels for a period of time. For some applications, this facilitates measurement of blood flow by measuring the time the contrast agent is evacuated from a section of known volume of the blood vessel.

For some applications, the automated injection device is programmed to inject pulses of contrast agent in a predetermined pattern. For some applications, a series of pulses is used to measure blood velocity in a more precise manner by using time-density curves. For some applications, a series of pulses is used to measure blood velocity throughout the cardiac cycle by using time-density curves.

For some applications, the aforementioned hemodynamic measurements are made upon the aforementioned stabilized image stream. For some applications, the stabilized image stream is generated using techniques described in US 2008/0221442 to Tolkowsky, which is incorporated herein by reference. For some applications, the stabilized image stream is generated using techniques described in WO 10/058398 to Cohen, US 2010/0172556 to Cohen, and/or US 2010/0228076 to Blank, all of which applications are incorporated herein by reference. Typically, stabilization is performed by aligning images with one another with respect to a luminal section that contains the stenosis, or with respect to a location within the stenosis (such as the location of the minimal lesion diameter of the stenosis). Typically, automatic measurement of the progress of the contrast agent along the lumen is facilitated by aligning the angiographic images with each other, and/or by generating a stabilized image stream. For example, blood-velocity determination-functionality 16 may automatically align two of the angiographic images with one another, the times at which the respective images were acquired being separated by a given time period. The blood-velocity-determination functionality may then identify the location of a portion of the contrast agent in each of the two images (e.g., by identifying a pixel corresponding to the portion of the contrast agent that is furthest downstream), and may thereby determine a distance travelled by the contrast agent during the time period that separated the acquisition of the two images.

For some applications, the stabilized image stream is also enhanced. For some applications, such enhancement is performed using techniques described in WO 10/058398 to Cohen, US 2010/0172556 to Cohen, and/or US 2010/0228076 to Blank, all of which applications are incorporated herein by reference.

For some applications, the stabilized image stream is displayed on display 24. Hemodynamic measurements (such as the velocity of blood through the lumen) are performed (e.g., in accordance with the techniques described hereinabove), and the flow measurements are displayed upon the stabilized image stream. For some applications, flow measurements are displayed upon an image stream that has been both stabilized and enhanced.

In general, the scope of the present invention includes performing the following technique on a plurality of angiographic image frames of a moving lumen of a body, based upon techniques described in US 2008/0221442 to Tolkowsky, which is incorporated herein by reference:

1) aligning the image frames with each other, to reduce imaged motion of the portion of the subject's body, e.g., using image-stabilization functionality 17;

2) using the aligned image frames, determining a time it takes contrast agent to travel a known distance through the lumen, e.g., using blood-velocity-determination functionality 16;

3) at least partially in response thereto, determining a characteristic of the lumen, e.g., using lumen-characterization functionality 20; and 4) in response to the determined characteristic, generating an output on a display, e.g., using output-generation functionality 22.

For some applications, flow and/or another hemodynamic characteristic of the lumen is determined. For some applications, geometry of the lumen is determined, and the value of a current flow-related parameter of the lumen in the vicinity of a stenosis is determined based upon the time it takes the contrast agent to travel the known distance through the lumen and the determined geometry of the lumen. For some applications, an indication of the value of a second flow-related parameter of the subject is received, e.g., using flow-related-parameter receiving functionality 19, and the value of a luminal-flow-related index of the subject in the vicinity of the stenosis is determined, by determining a relationship between the current flow-related parameter and the second flow-related parameter. For some applications, techniques described herein for determining a luminal-flow-related index are combined with techniques described in US 2008/0221442 to Tolkowsky, which is incorporated herein by reference.

Typically, processor 10 includes current-flow-related-parameter-determination functionality 18. The current-flow-related-parameter-determination functionality uses the aforementioned geometrical measurements in conjunction with the aforementioned hemodynamic measurements in order to compute the value of a current flow-related parameter (e.g., blood pressure, blood velocity, or flow) at a given location in the lumen (e.g., in the vicinity of a stenosis), as will be further detailed in subsequent sections of the description of embodiments of the current invention.

Further typically, processor 10 includes flow-related-parameter-receiving functionality 19. In order to calculate the subject's luminal-flow-related index, the processor receives an indication of the value of a flow-related parameter (such as pressure, flow, or blood velocity) at a second location within a lumen of the subject, or an indication of the value of a flow-related parameter (such as pressure, flow, or blood velocity) at the given location within the lumen (e.g., in the vicinity of the stenosis) at a time when the lumen was healthy. For example, the processor may receive an indication of the subject's aortic pressure and may calculate the subject's luminal flow-related index by assuming that the pressure immediately upstream of the stenosis is equal to the subject's aortic pressure. For some applications, aortic pressure is measured via a pressure sensor that is coupled to a guiding catheter, and aortic pressure receiving functionality receives an indication of the subject's aortic pressure from the pressure sensor. For some applications, the aortic pressure serves as an input for the calculation of the pressure proximal to the stenosis, typically, by the pressure proximal to the stenosis being assumed to be equal to the aortic pressure. Alternatively or additionally, the value of a flow-related parameter (such as pressure, flow, or blood velocity) at the second location within the lumen may be determined by performing image-processing on an angiographic image of the second location. For example, the geometry of the lumen at the second location may be determined using the techniques described herein, and blood pressure, blood velocity and/or flow at the second location may thereby be determined, using the techniques described herein.

For some applications, the processor receives an indication of the value of a flow-related parameter within the subject's lumen at a time when the subject was healthy, by receiving data relating to the subject's patient history. For example, the processor may receive at least one angiographic image of the subject's lumen that was acquired at a time when the subject was healthy, as described hereinbelow. The processor may derive flow or blood velocity within the lumen at the time of the acquisition of the previously-acquired image (i.e., at the time when the lumen was healthy), by performing image processing on the previously-acquired image.

Typically, processor 10 includes index-determination functionality 21, which is configured to determine the subject's luminal-flow-related index (e.g., FFR) based upon input from at least some of the other functionalities of the processor. As described hereinabove, the aforementioned geometrical measurements are used in conjunction with the aforementioned hemodynamic measurements to compute a current flow-related parameter (e.g., blood pressure, blood velocity, or flow) in the vicinity of the stenosis, as will be further detailed in subsequent sections of the description of embodiments of the current invention. The subject's luminal flow-related parameter is determined by comparing the value of the current flow-related parameter to the value of the flow-related parameter the indication of which was received by flow-related-parameter-receiving functionality 19, as described hereinabove. For some applications, such computations are made automatically. For some applications, such computations are made on line.

For some applications, the pressure drop induced by a stenosis is calculated and is then used to calculate a luminal-flow-related index (e.g., FFR). For example, the pressure drop induced by the stenosis may be determined by (a) determining the current pressure in the vicinity of the stenosis based upon the geometrical measurements and the hemodynamic measurements that are determined by the processor, and (b) comparing the current pressure in the vicinity of the stenosis to blood pressure at a location upstream of the stenosis (e.g., the subject's aortic pressure). For some applications, a luminal-flow-related index (e.g., FFR) is determined by (a) determining the current flow or blood velocity in the vicinity of the stenosis based upon the geometrical measurements and the hemodynamic measurements that are determined by the processor, and (b) comparing the current flow or blood velocity in the vicinity of the stenosis to historical flow or blood velocity within the lumen, at a time when the lumen was healthy.

Typically, in response to the FFR or another index being determined, output-generation functionality 22 of the processor drives display 24 to display an output, e.g., as described hereinbelow with reference to FIG. 4.

Figure 2:
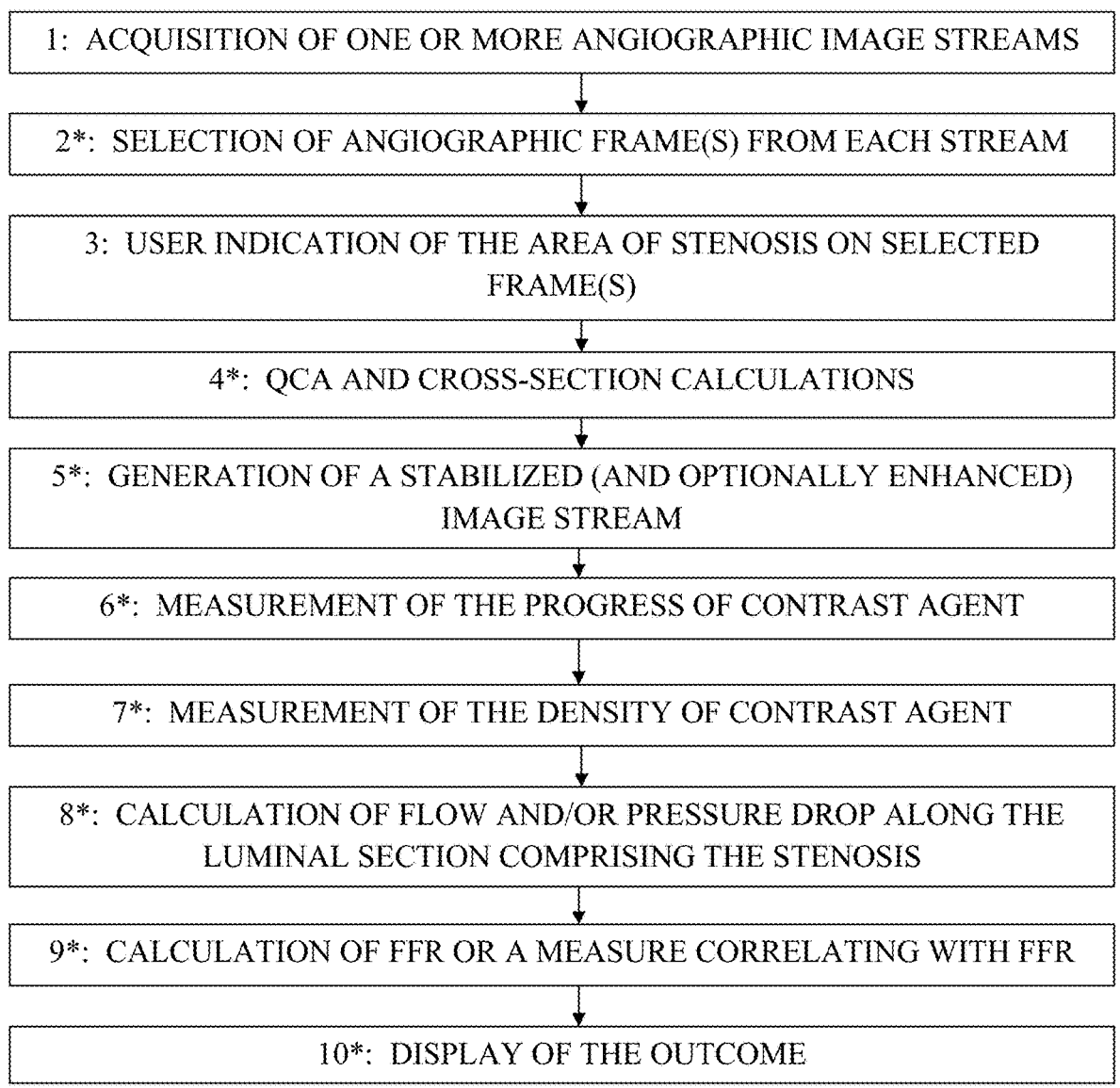
FIG. 2 is a flow chart, at least some of the steps of which are used to calculate a luminal-flow-related index, by means of image processing, in accordance with some applications of the present invention.

Reference is now made to FIG. 2, which is a flow chart, at least some of the steps of which are used to calculate a luminal-flow-related index, by means of image processing, in accordance with some applications of the present invention. It is noted that, for some applications, some of the steps shown in FIG. 2 may be practiced, without all of the steps shown in FIG. 2 necessarily being practiced in combination. Typically, at least the steps that are marked with asterisks in FIG. 2 are performed automatically.

In step 1, one or more angiographic image streams are acquired. For some applications, processor 10 automatically determines that an angiogram has commenced and/or has ended, for example, in accordance with techniques described in WO 10/058398 to Cohen, US 2010/0172556 to Cohen, and/or US 2010/0228076 to Blank, all of which applications are incorporated herein by reference. For some applications, the determination that an angiogram has commenced and/or has ended is performed in real time or near real time, for example, in accordance with techniques described in WO 10/058398 to Cohen, US 2010/0172556 to Cohen, and/or US 2010/0228076 to Blank, all of which applications are incorporated herein by reference.

In step 2, at least one suitable angiographic frame is selected from the angiographic sequence by processor 10. For some applications, the selection of the frame is performed automatically, and/or in real time or near real time, for example, in accordance with techniques described in WO 10/058398 to Cohen, US 2010/0172556 to Cohen, and/or US 2010/0228076 to Blank, all of which applications are incorporated herein by reference.

In step 3, the user indicates the location of interest, which is typically the area of a stenosis in the lumen. For some applications, processor 10 identifies the location of a stenosis at least partially automatically, for example, in accordance with techniques described in WO 10/058398 to Cohen, US 2010/0172556 to Cohen, and/or US 2010/0228076 to Blank, all of which applications are incorporated herein by reference. For example, a user may designate a single location in an image that is at or near a given location of a given blood vessel in the image (e.g., using user interface 13, the user may click at or near the given location). For some applications, in response to the user designating the single location, the system automatically detects a stenosis in the vicinity. For example, the system may identify edge lines and the reference diameters of the stenosis.

In step 4, quantitative measurements of the lumen geometry (e.g., QCA measurements) are performed by geometry-indication-receiving functionality 14. For some applications, QCA measurements are performed automatically and/or in real time or near real time, for example, in accordance with techniques described in WO 10/058398 to Cohen, US 2010/0172556 to Cohen, and/or US 2010/0228076 to Blank, all of which applications are incorporated herein by reference. For some applications, in step 4 of the procedure, the cross-sectional area of the lumen in the vicinity of the stenosis, and/or at other locations along the lumen (e.g., within a healthy portion of the lumen), is determined by performing densitometry on at least one of the angiographic images, in accordance with the techniques described hereinbelow.

In step 5, additional image frames in the angiographic image stream are aligned with one another, for example, by aligning the image frames with each other with respect to the location of the stenosis within the image frames. For some applications, alignment is performed automatically and/or in real time or near real time, for example, in accordance with techniques described in US 2008/0221442 to Tolkowsky, WO 10/058398 to Cohen, US 2010/0172556 to Cohen, and/or US 2010/0228076 to Blank, all of which applications are incorporated herein by reference. Typically, the alignment is performed such as to generate a stabilized angiographic image stream, for example, in accordance with techniques described in US 2008/0221442 to Tolkowsky, WO 10/058398 to Cohen, US 2010/0172556 to Cohen, and/or US 2010/0228076 to Blank, all of which applications are incorporated herein by reference. For some applications, the alignment is performed such as to generate an angiographic image stream that is both stabilized and enhanced, for example, in accordance with techniques described in WO 10/058398 to Cohen, US 2010/0172556 to Cohen, and/or US 2010/0228076 to Blank, all of which applications are incorporated herein by reference.

For some applications, the QCA performed in step 4 on the suitable frame selected in step 2 is preceded by enhancement of the suitable frame selected in frame 2. Such enhancement is typically performed according to the techniques described with reference to step 5, e.g., in accordance with techniques described in WO 10/058398 to Cohen, US 2010/0172556 to Cohen, and/or US 2010/0228076 to Blank, all of which applications are incorporated herein by reference.

In steps 6 and 7, which may be performed in combination with one another, the progress and density of the contrast agent along the luminal section proximal and/or distal to the stenosis, and/or other hemodynamic parameters, are measured by blood-velocity-determination functionality 16. For some applications, such measurements are performed automatically, for example, in accordance with techniques described hereinabove with reference to FIG. 1. For some applications, such measurements are performed in real time or near real time. For some applications, such measurements are performed for one or more regions located along the luminal section. For some applications, such regions are selected automatically. Typically, such regions are located along the center line of the luminal section. For some applications, the center line is determined automatically, for example, in accordance with techniques described in WO 10/058398 to Cohen, US 2010/0172556 to Cohen, and/or US 2010/0228076 to Blank, all of which applications are incorporated herein by reference.

Figure 3A:
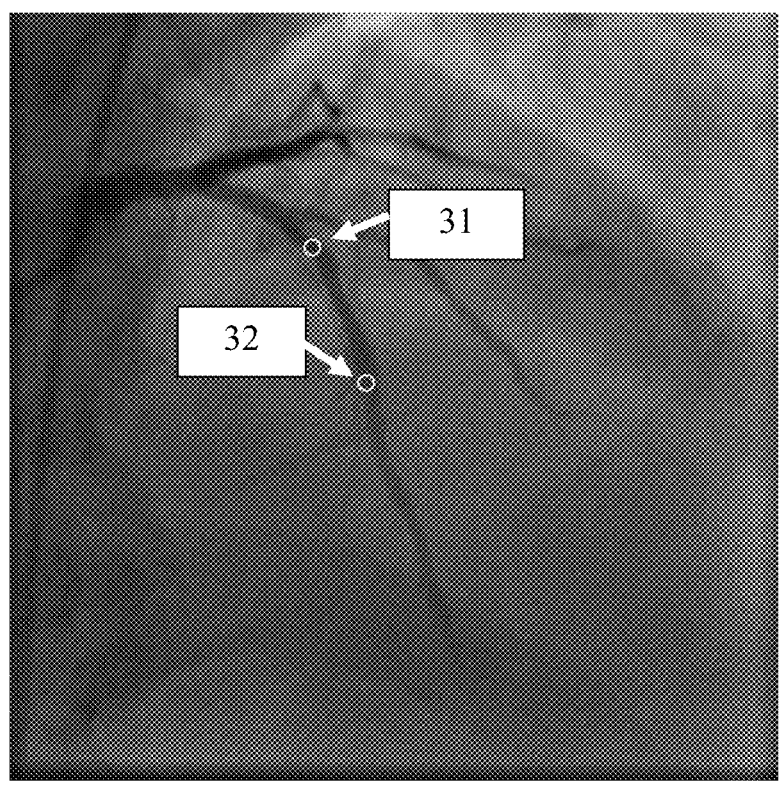
FIG. 3A shows regions of an angiographic image at which the progress of contrast agent through the lumen is measured, in accordance with some applications of the present invention.

Reference is made to FIG. 3A, which shows regions of an angiographic image at which the progress of contrast agent through the lumen is measured, in accordance with some applications of the present invention. FIG. 3A is a sample frame taken from an angiographic image stream. Regions 31 and 32 comprise a pair of regions along the center line of the lumen. Reference is also made to FIG. 3B, which shows an illustrative example of time-density curves of a contrast agent measured at region 31 (the solid curve) and region 32 (the dashed curve). For some applications, blood-velocity-determination functionality 16 determines the blood velocity at a region within the lumen by comparing the contrast agent time-density curves at proximal and distal locations within the region. The blood-velocity-determination functionality 16 thereby determines the time taken for the contrast agent to flow from the proximal location to the distal location. For example, blood-velocity-determination functionality 16 may determine that a given peak of the time-density curve appears at region 31 in a first angiographic image, and that the peak appears at region 32 in a second angiographic image. The blood-velocity-determination functionality may thereby determine the time that it took for the contrast agent to travel from the first region of interest to the second region of interest, based upon an interval (e.g., a time interval and/or a number of image frames) between an acquisition of the first angiographic image and an acquisition of the second angiographic image.

Typically, the blood-velocity-determination functionality is configured to determine blood velocity within the lumen by (a) defining at least first and second regions of interest along the lumen in one of the angiographic images, (b) identifying the regions of interest in at least some additional angiographic images belonging to the set of angiographic images, (c) determining a distance between the regions of interest, and (d) determining that a presence of a contrast agent (e.g., a bolus of contrast agent, a given concentration of contrast agent, and/or a given pattern of contrast agent) appears at the first region of interest in a first one of the angiographic images and that the presence of contrast agent appears at the second region of interest in a second one of the angiographic images.

Reference is again made to FIG. 2. In step 8, the aforementioned lumen geometry and hemodynamic measurements are utilized to calculate a current flow-related parameter of the lumen in the vicinity of the stenosis, typically, by means of current-flow-related-parameter-determination functionality 18.

In step 9, the luminal-flow-related index is calculated in the vicinity of the stenosis (e.g., along the luminal section comprising the stenosis), typically by means of index-determination functionality 21. For some applications, the index is calculated with respect to a specific stenosis which was indicated by the user, and/or identified by the processor, in step 3. For some applications, the index is calculated for multiple locations along a luminal section.

As described hereinabove, for some applications, the pressure drop induced by the stenosis is determined and is then used to calculate a luminal-flow-related index (e.g., FFR). For example, the pressure drop induced by the stenosis may be determined by (a) determining the current pressure in the vicinity of the stenosis, based upon the geometrical measurements and the hemodynamic measurements that are determined by the processor, and (b) comparing the current pressure in the vicinity of the stenosis to blood pressure at a location upstream of the stenosis (e.g., the subject's aortic pressure). For some applications, a luminal-flow-related index (e.g., FFR) is calculated by (a) determining the current flow or blood velocity in the vicinity of the stenosis, based upon the geometrical measurements and the hemodynamic measurements that are determined by the processor, and (b) comparing the current flow or blood velocity in the vicinity of the stenosis to historical flow or blood velocity within the lumen at a time when the lumen was healthy. Alternatively or additionally, a flow-related parameter (such as pressure, flow, or blood velocity) at a second location within the lumen is determined by performing image-processing on an angiographic image of the second location. For example, the geometry of the lumen at the second location may be determined using the techniques described herein, and blood pressure, blood velocity and/or flow at the second location may thereby be determined, using the techniques described herein. A luminal flow-related index is determined by comparing the value of the flow-related parameter at the location of interest to the value of the flow-related parameter at the second location.

In step 10, output-generation functionality 22 drives display 24 to display the luminal-flow-related index. For some applications, a single value corresponding to the specific stenosis is displayed. For some applications, multiple values are displayed along the luminal section comprising the stenosis. For some applications, the index is displayed upon an angiogram frame, such as the frame selected in step 2. For some applications, the parameter is displayed upon an image stream that is stabilized with respect to the stenosis, e.g., a stabilized image stream as described hereinabove.

Figure 4:
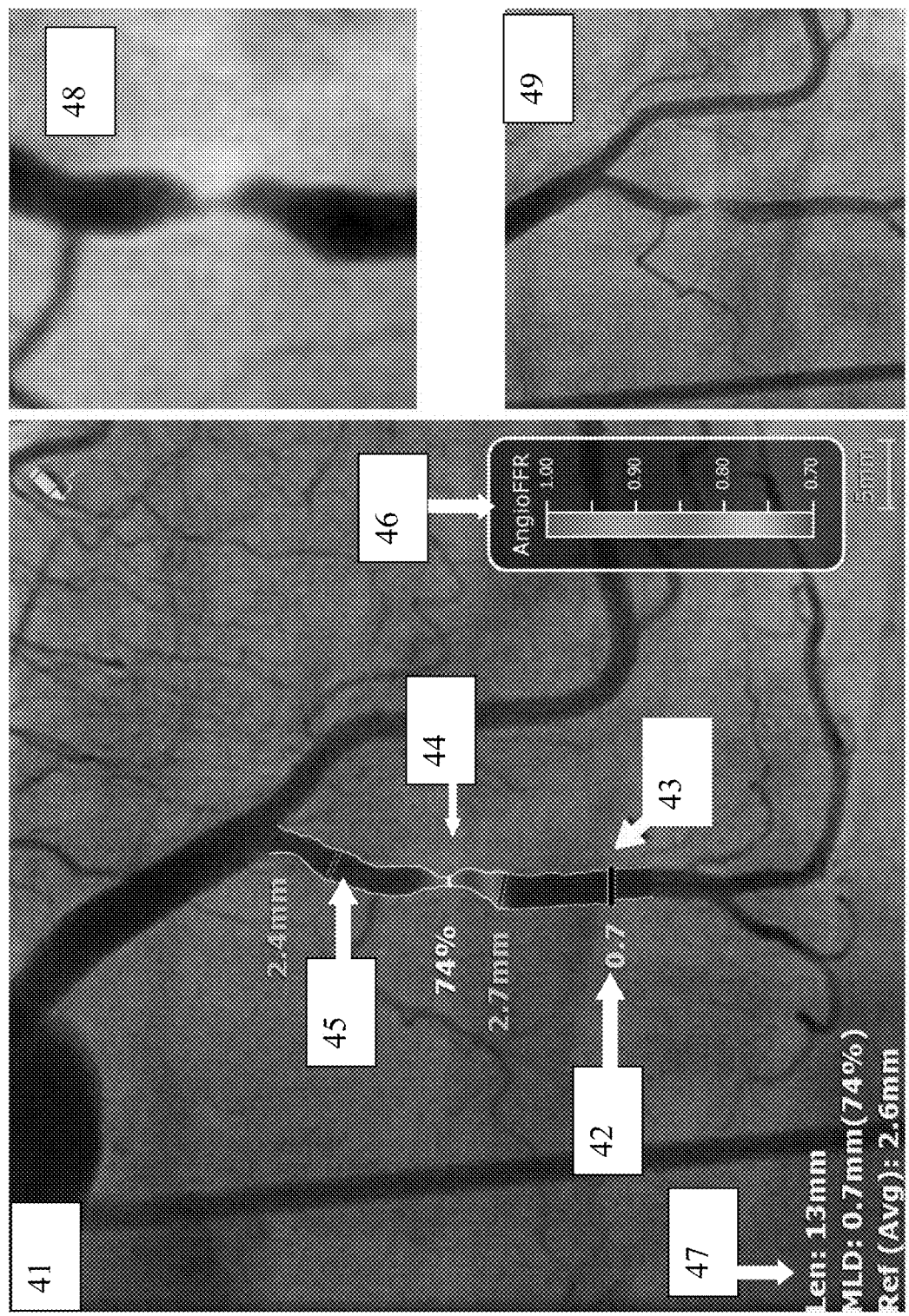
FIG. 4 shows an angiogram image with an FFR value calculated and displayed distally to a stenosis, in accordance with some applications of the present invention.

Reference is made to FIG. 4, which shows an angiogram image 41 with an FFR value 42 calculated and displayed distally to a stenosis, in accordance with some applications of the present invention. For some applications of the present invention, an FFR value (or the value of another luminal flow-related index) at a given site along a lumen is displayed on an image of the lumen (e.g., on a selected raw angiographic image, on a stabilized angiographic image stream, on an enhanced angiographic image frame, and/or on a stabilized and enhanced angiographic image stream) at a location within the image (or image stream) corresponding to the site. For example, in image 41, an FFR value of 0.7 corresponds to a lumen location 43 that is downstream of stenotic section 44 in lumen 45. For some applications, the lumen is displayed in a manner that indicates the FFR values of respective locations along the lumen. For example, a legend 46, according to which different FFR values are assigned respective colors and/or patterns may be used, and the lumen may be displayed in a manner that indicates the FFR values of respective locations along the lumen, in accordance with the legend. For example, lumen 45, in the area of stenotic section 44, is colored with respect to calculated FFR values according to FFR color legend 46. (It is noted that, since FIG. 4 is shown in black-and-white, the legend appears in black-and-white. However, a color legend is typically used to indicate FFR values of locations along the lumen.) For some applications, QCA parameters 47 for the stenotic section 44 are displayed on the angiographic image and/or the angiographic image stream. For some applications, an enhanced image of stenotic section 44 is displayed in window 48, and/or a stabilized clip of lumen 45 is displayed in window 49. For some applications, the aforementioned FFR calculations, QCA, enhancement and/or stabilization are all performed by processor 10, typically on line, in response to the user's indication (e.g., via user interface 13) of the location of the stenosis, or in response to the system automatically identifying the stenosis, e.g., in response to an input from the user.

For some applications, in response to determining that the subject's FFR passes a first threshold value, an output is generated on the display indicating that treatment of the subject (e.g., by deploying a stent at the stenosis) is recommended. For example, by way of illustration, in response to determining that the FFR of the stenosis is less than 0.75, an output may be generated indicating that treatment of the subject is recommended. For some applications, in response to determining that the subject's FFR passed a second threshold value but did not pass the first threshold value, an output is generated on the display recommending that the luminal-flow-related index be determined using a sensor that is inserted into the lumen (e.g., by inserting a wire equipped with pressure sensors into the lumen). For example, by way of illustration, in response to determining that the FFR of the stenosis is less than 0.8 but not less than 0.75 (i.e., in response to determining that the subject's FFR is between 0.8 and 0.75), an output may be generated recommending that the luminal-flow-related index be determined using a sensor that is inserted into the lumen.

For some applications, Instantaneous wave-Free Ratio (iFR), or a parameter that is related to iFR (e.g., by being statistically correlated with iFR) is determined by processor 10, as an alternative to, or in addition to the processor determining FFR. Typically, the processor determines iFR using generally similar techniques to those described herein for determining FFR. iFR is a pressure-derived index of stenosis severity the determination of which, unlike typical FFR, does not typically require pharmacologic vasodilation. iFR has been described as providing a drug-free index of stenosis severity comparable to FFR (Sian Sen et al., "Development and Validation of a New, Adenosine-Independent Index of Stenosis Severity From Coronary Wave-Intensity Analysis," Journal of the American College of Cardiology, Vol. 59 2012).

For some applications, another luminal-flow-related index, for example, one of the luminal-flow-related indices described hereinabove, is determined by processor 10, as an alternative to, or in addition to the processor determining FFR. Typically, the processor determines the other index using generally similar techniques to those described herein for determining FFR, mutatis mutandis. Further typically, the other index is displayed in a generally similar manner to that described with reference to FFR, mutatis mutandis.

For some applications, a luminal-flow-related index of a subject is determined based upon an angiographic image stream of the subject's lumen, via a procedure that includes at least some of the following steps:

1. A healthcare professional induces a hyperemic condition within the subject's lumen. It is noted that this step is optional, since the determination of some luminal-flow related indices is not dependent on inducing a hyperemic condition within the subject's lumen.
2. A healthcare professional initiates a cine angiogram of the lumen.
3. In response to the healthcare professional initiating the angiogram, processor 10 simultaneously acquires an x-ray image stream of the lumen (e.g., a high-resolution x-ray image stream of the lumen) and the subject's ECG signal.
4. Angiogram-detecting functionality (not shown) of processor 10 automatically determines that an angiogram has commenced and/or has ended, for example, in accordance with techniques described in WO 10/058398 to Cohen, US 2010/0172556 to Cohen, and/or US 2010/0228076 to Blank, all of which applications are incorporated herein by reference. For some applications, the identification that an angiogram has commenced and/or has ended is performed in real time or near real time, for example, in accordance with techniques described in WO 10/058398 to Cohen, US 2010/0172556 to Cohen, and/or US 2010/0228076 to Blank, all of which applications are incorporated herein by reference.
5. Processor 10 analyzes the subject's ECG signal.
6. Processor 10 selects a suitable angiographic image frame(s) for analysis, typically in response to the analysis of the ECG signal. For example, the processor may select the image with the highest contrast that is near a QRS complex. For some applications, steps 5 and 6 are performed in accordance with techniques described in WO 10/058398 to Cohen, US 2010/0172556 to Cohen, and/or US 2010/0228076 to Blank, all of which applications are incorporated herein by reference.
7. A healthcare professional indicates a location of the guiding catheter on the angiographic image (e.g., using user interface 13).
8. The geometry-indication-receiving functionality 14 of the processor utilizes the known dimensions of the guiding catheter to calibrate dimensions that are measured in the angiographic image, for example, in accordance with techniques described in WO 10/058398 to Cohen, US 2010/0172556 to Cohen, and/or US 2010/0228076 to Blank, all of which applications are incorporated herein by reference. For some applications, alternative techniques are used for calibrating the dimensions that are measured in the angiographic image. For some applications, techniques as described in International Patent Application PCT/IL2013/050438 (published as WO 13/175472), which is incorporated herein by reference, are used for calibrating the dimensions that are measured in the image.
9. A healthcare professional indicates a location of the stenosis on the angiographic image (e.g., using user interface 13). For some applications, processor 10 identifies the location of a stenosis at least partially automatically, for example, in accordance with techniques described in WO 10/058398 to Cohen, US 2010/0172556 to Cohen, and/or US 2010/0228076 to Blank, all of which applications are incorporated herein by reference. For example, a user may designate a single location in an image that is at or near a given location of a given blood lumen in the image (e.g., using user interface 13). In response to the user designating the single location, the system automatically detects a stenosis in the vicinity. For example, the system may identify edge lines and the reference diameters of the stenosis.
10. Quantitative measurements of the lumen geometry (e.g., QCA measurements) are performed by geometry-indication-receiving functionality 14. For some applications, QCA measurements are performed automatically and/or in real time or near real time, for example, in accordance with techniques described in WO 10/058398 to Cohen, US 2010/0172556 to Cohen, and/or US 2010/0228076 to Blank, all of which applications are incorporated herein by reference. For some applications, one or more of the following steps are performed automatically by the geometry-indication-receiving functionality, in order to perform the QCA measurements:

a. The lumen is enhanced, for example, in accordance with techniques described in WO 10/058398 to Cohen, US 2010/0172556 to Cohen, and/or US 2010/0228076 to Blank, all of which applications are incorporated herein by reference.

b. A vesselness index of pixels of the image is calculated, for example, in accordance with techniques described in WO 10/058398 to Cohen, US 2010/0172556 to Cohen, and/or US 2010/0228076 to Blank, all of which applications are incorporated herein by reference.

c. Centerlines of lumens are automatically determined, for example, in accordance with techniques described in WO 10/058398 to Cohen, US 2010/0172556 to Cohen, and/or US 2010/0228076 to Blank, all of which applications are incorporated herein by reference.

d. Edges of lumens are automatically detected, for example, in accordance with techniques described in WO 10/058398 to Cohen, US 2010/0172556 to Cohen, and/or US 2010/0228076 to Blank, all of which applications are incorporated herein by reference.

e. Measurements of the lumen geometry are made automatically, for example, in accordance with techniques described in WO 10/058398 to Cohen, US 2010/0172556 to Cohen, and/or US 2010/0228076 to Blank, all of which applications are incorporated herein by reference.

11. Blood-velocity-determination functionality 16 of processor 10 defines at least two regions of interest, typically along the lumen center line. For some applications, three or more regions of interest are selected, the regions of interest typically being equidistant from each other along the center line.

12. The lumen is tracked through at least a portion of, and typically through the entire, angiographic sequence. For some applications, the lumen is automatically identified in the angiographic images and the images are aligned with respect to each other by aligning the lumen in the images, for example, in accordance with techniques described in US 2008/0221442 to Tolkowsky, WO 10/058398 to Cohen, US 2010/0172556 to Cohen, and/or US 2010/0228076 to Blank, all of which applications are incorporated herein by reference. For some applications, in order to align the images with respect to each other, the shape of the lumen in some of the images is warped. For example, the warping may be applied by determining a transformation function for transforming locations within the lumen (such as the regions of interest) in respective images with respect to each other, for example, in accordance with techniques described in WO 10/058398 to Cohen, US 2010/0172556 to Cohen, and/or US 2010/0228076 to Blank, all of which applications are incorporated herein by reference. For some applications, a transformation function is determined using techniques as described in International Patent Application PCT/IL2013/050438 (published as WO 13/175472), which is incorporated herein by reference.

13. Blood-velocity-determination functionality 16 of processor 10 identifies the regions of interest within all of the image frames of the angiographic sequence. Typically, the alignment of the image frames with each other, and/or the determination of transformation functions (for transforming locations within the lumen (such as the regions of interest) in respective images with respect to each other), as performed in step 12, facilitates the identification of the regions of interest within the image frames of the angiographic sequence.

14. Blood-velocity-determination functionality 16 of processor 10 estimates the velocity of the contrast agent through the coronary artery using time-density curves and/or contrast flow maps. The blood-velocity-determination functionality typically determines the blood velocity by determining that a point (e.g., a peak) of the time-density curve moved from a first region of interest to an adjacent region of interest between first and second (not necessarily adjacent) angiographic image frames. The time taken for the contrast agent to move from the first region of interest to the second region of interest may be determined by determining the period of time that separated the acquisition of the first image frame and the acquisition of the second image frame. For some applications, the time taken for a bolus of contrast agent, a given concentration of contrast agent, and/or a pattern of contrast agent to move from the first region of interest to the second region of interest is determined. The distance between the first region of interest and the second region of interest may be determined by determining the distance between the first region of interest and the second region of interest in the image frame that was selected in step 6, the distance being calibrated based upon the known dimensions of the guiding catheter, in accordance with step 8.

15. Processor 10 calculates hyperemic coronary flow, based upon the QCA and the blood velocity calculations.

16. The pressure drop due to the stenosis is calculated, based upon the determined hyperemic flow, in accordance with the techniques described herein.

17. Aortic pressure is received by flow-related-parameter-receiving functionality 19. For some applications, a healthcare professional manually inputs the aortic pressure, for example, based upon the pressure detected by an aortic pressure sensor. Alternatively or additionally, the processor automatically receives the aortic pressure from an aortic pressure sensor.

For some applications, as an alternative to receiving the subject's aortic pressure, the flow-related-parameter-determination functionality receives an indication of a parameter that is indicative of a flow-related parameter within the subject's lumen while the subject was healthy, by receiving data relating to the subject's patient history. For example, the processor may receive at least one angiographic image of the subject's lumen that was acquired at a time when the subject was healthy, as described hereinbelow. The processor may derive flow within the lumen or blood velocity within the lumen at the time of the acquisition of the previously-acquired image (i.e., at the time when the lumen was healthy), by performing image processing on the previously-acquired image. Alternatively or additionally, the flow-related-parameter-determination functionality receives an angiographic image of a second location within the lumen, and a flow-related parameter (such as pressure, flow, or blood velocity) at the second location within the lumen is determined by performing image-processing on the angiographic image of the second location. For example, the geometry of the lumen at the second location may be determined using the techniques described herein, and blood pressure, blood velocity and/or flow at the second location may thereby be determined, using the techniques described herein.

18. Index-determination functionality calculates FFR and/or another luminal-flow-related index based upon the aortic pressure and the calculated pressure drop, in accordance with the techniques described herein. Alternatively or additionally, index-determination functionality calculates FFR and/or another luminal-flow-related index by comparing current flow or blood velocity in the vicinity of the stenosis to flow or blood velocity within the lumen at a time when the lumen was healthy, in accordance with the techniques described herein. Further alternatively or additionally, the luminal flow-related index is determined by comparing the value of the current flow-related parameter at the location of interest to the value of the flow-related parameter at the second location.

For some applications, the techniques described herein are applied to a lumen that defines a second stenosis that is downstream of a first stenosis. For some such applications, in order to determine a luminal-flow-related index of the second stenosis, the processor determines the luminal pressure at a site between the first stenosis and the second stenosis, and uses this pressure as the pressure to which the pressure downstream of the second stenosis is compared. Alternatively, in order to determine the luminal-flow-related index of the second stenosis, the processor uses the aortic pressure as the pressure to which the pressure downstream of the second stenosis is compared.

The following portion of the present application describes models according to which parameters that are derived from angiogram data are used in order to calculate a luminal-flow-related index (e.g., FFR), in accordance with some applications of the present invention. Typically such steps are performed by index-determination functionality 21 of processor 10.

For some applications of the current invention, FFR, and/or another luminal-flow-related index is deduced from data that are typically derived from the angiogram. For some applications, such parameters include the geometry of the lumen, the aortic pressure, the density of the contrast agent as observed in the angiogram images, the hyperemic flow, and/or the density and viscosity of blood. It is noted that typically, blood velocity and lumen geometry are determined solely by performing image processing on the two-dimensional angiographic images. Further typically, blood velocity and lumen geometry are determined without generating a three-dimensional model of the lumen. For some applications, such parameters are derived using one or more of the following techniques:

For some applications, the geometry of the lumen is determined, typically online and typically in response to a single user click, at the area of the stenosis, e.g., by performing QCA. As described hereinabove, QCA may be performed using images that were acquired from two or more viewing angles.

For some applications, aortic pressure $P_a$ is measured through the guiding catheter, as described hereinabove.

For some applications, geometry-indication-receiving functionality 14 determines the cross-sectional area of the lumen in the vicinity of the stenosis, and/or at other locations along the lumen (e.g., within a healthy portion of the lumen), by performing densitometry on at least one of the angiographic images, in accordance with the techniques described hereinbelow. For some applications, densitometry is performed, typically automatically, by comparing the density of the contrast agent in a healthy section of the lumen (e.g., the section proximal to the stenosis) to the density of the contrast agent in other parts of the lumen (e.g., in the vicinity of the stenosis, or downstream of the stenosis). For some applications, such a comparison is made on an angiogram image after background subtraction is applied to the angiogram image. For some applications, background subtraction is performed by subtracting images acquired before the contrast injection from images acquired after the contrast injection. For some applications, the images acquired before the contrast injection and the images acquired after the contrast injection are gated to the same phase in the cardiac cycle. For some applications, the images acquired before the contrast injection and the images acquired after the contrast injection are gated to the end-diastolic phase.

For some applications, the hyperemic flow is calculated by digital subtraction angiography, for example using techniques that are similar to those described in one or more of the following references, which are incorporated herein by reference:

Molloi, S., Ersahin, A., Tang, J., Hicks, J. & Leung, C. Y., 1996 "Quantification of volumetric coronary blood flow with dual-energy digital subtraction angiography," Circulation 93, 1919-1927;

Molloi, S., Zhou, Y. & Kassab, G. S. 2004 "Regional volumetric coronary blood flow measurement by digital angiography: in vivo validation," Acad. Radiol. 11, 757-766;

Sabee Molloi, David Chalyan, Huy Le and Jerry T. Wong, 2012, "Estimation of coronary artery hyperemic blood flow based on arterial lumen volume using angiographic images," The International Journal Of Cardiovascular Imaging, Volume 28, Number 1, 1-11; and Molloi S, Bednarz G, Tang J, Zhou Y, Mathur T (1998), "Absolute volumetric coronary blood flow measurement with digital subtraction angiography," Int J Card Imaging 14:137-145.

For some applications, the hyperemic flow is calculated by performing digital subtraction on images of the stenosis or lumens, which have been stabilized via image tracking, with or without warping of the lumens in the images, e.g., using techniques described hereinabove. For some applications, flow is determined in accordance with techniques described in US 2008/0221442 to Tolkowsky, which is incorporated herein by reference. For example, on-line geometric and/or hemodynamic measurements (e.g., size, flow, ejection fraction) may be made and/or displayed upon stabilized images, e.g., as described with reference to FIG. 4. Alternatively or additionally, a stabilized image stream may be used for on-line measurement of the flow within a lumen, e.g., by measuring the time it takes a presence of contrast agent (e.g., a bolus of contrast agent, a given concentration of contrast agent, and/or a pattern of contrast agent) to travel a known distance, in accordance with the techniques described hereinabove.

For some applications, the hyperemic flow is calculated by multiplying blood velocity, by the lumen cross-sectional area, the blood velocity and the lumen cross-sectional area typically having been determined automatically by processor 10.

For some applications, blood velocity is calculated from angiogram images by comparing density curves, for example, as described hereinabove with reference to FIG. 3B, and/or as described in Gerhard Albert ten Brinke, 2011, "Automated coronary flow reserve assessment using planar x-ray angiography", PhD dissertation, Universiteit Twente, chapter 3 (hereinafter "ten Brinke"), which is incorporated herein by reference.

For some applications, the blood velocity is calculated from angiogram images by using contrast flow maps, e.g., using techniques that are similar to those described in ten Brinke, which is incorporated herein by reference.

For some applications, the cross-sectional area is calculated from QCA measurements of the artery and/or by densitometry.

For some applications, the density and/or viscosity of blood is determined, for example, using techniques described in one or more of the following references, which are incorporated herein by reference:

Gerald E. Miller, "Fundamentals of Biomedical Transport Processes, Morgan & Claypool Publishers," chapter 2; and Buddy D. Ratner, "Biomaterials Science: An Introduction to Materials in Medicine," Elsevier, chapter 7.

The following is a description of how FFR is calculated, utilizing at least some of the above-mentioned parameters, the parameters typically having been determined automatically from one or more angiographic images, in accordance with some applications of the present invention.

As described hereinabove, mathematically, FFR is defined as:

$$FFR=P_d/P_a=(P_a-\Delta P_s)/P_a$$

Assuming there is no disease in the lumen proximal to the stenosis in question, the value of the proximal pressure $P_a$ may be assumed to be the same as the aortic pressure. Therefore, typically, processor 10 assumes that the pressure proximal to the stenosis is equal to the measured aortic pressure. For some applications, in order to calculate FFR, the processor calculates the pressure drop in the stenotic part of the lumen, i.e., $\Delta P_s$.

For some applications, the calculation of $\Delta P_s$ is performed by using the Bernoulli equation, e.g., using generally similar techniques to those described in Yunlong Huo, Mark Svendsen, Jenny Susana Choy, Z.-D. Zhang and Ghassan S. Kassab, 2011, "A validated predictive model of coronary fractional flow reserve," J. R. Soc. Interface (hereinafter "Huo"), which is incorporated herein by reference. For some applications, the system applies the Bernoulli equation, while ignoring the effect of gravity in the coronary circulatory system, such that the Bernoulli equation can be written as follows:

$$\Delta P_s = \Delta P_{convective} + \Delta P_{constriction} + \Delta P_{diffusive} + \Delta P_{expansion}$$

Each element of the pressure drop in the above equation is a function of the lumen geometry (e.g., lengths and cross-sections), the hyperemic flow rate in the lumen segment and the density and viscosity of blood, all of which parameters may be determined automatically from angiographic images of the lumen, in accordance with techniques described herein. Thus, for some applications, the value of the pressure drop is calculated using the aforementioned parameters.

For some applications, the pressure drop is calculated in a generally similar manner to that described in Huo, but using parameters that are automatically determined based upon angiographic images of the lumen, as described hereinabove.

For some applications, FFR and/or another luminal-flow-related index, is determined by processor 10 generating a local model of a portion of the lumen, using a combination of QCA and densitometry data obtained from angiogram images.

The following is a description of how FFR may be calculated, utilizing the above-mentioned data.

FFR is defined as:

$$FFR=P_d/P_a$$

Assuming there is no disease in the lumen proximal to the stenosis in question, the value of the proximal pressure $P_a$ may be assumed to be the same as the aortic pressure. For some applications, aortic pressure is measured through the guiding catheter, as described hereinabove.

What remains, in order to calculate FFR, is to calculate the pressure distal to the stenotic part of the lumen, i.e., $P_d$.

For some applications the pressure distal to the stenotic portion of the lumen is determined by the processor as follows:

1) An angiogram is performed under hyperemic conditions.
2) QCA and densitometry are performed on the stenotic portion and in the vicinity thereof. As described hereinabove, for some applications, QCA is performed using images acquired from two or more viewing angles.
3) One or more of the following boundary conditions are determined:
   a. coronary blood flow;
   b. proximal blood pressure; and
   c. proximal blood velocity.
4) Computational fluid dynamics equations are solved, using the aforementioned parameters as inputs, in order to obtain the pressure distal to the stenotic part of the lumen, i.e., $P_d$. For some applications, the Navier-Stokes equations listed below are solved, using the aforementioned parameters as inputs, in order to obtain the pressure distal to the stenotic part of the lumen:

$$\partial p/\partial t+\partial/\partial x_j[\rho u_j]=0$$

$$\partial/\partial t(\rho u_i)+\partial/\partial x_j[\rho u_i u_j+p\delta_{ij}-\tau_{ji}]=0, i=1,2,3$$

$$\partial/\partial t(\rho e_0)+\partial/\partial x_j[\rho u_j e_0+u_j p+q_j+u_i \tau_{ji}]=0$$

For some applications, FFR is deduced by solving the computational fluid dynamics equations, which are dependent on data that is typically available in the angiogram. For some applications, such parameters include the geometry of the coronary vessel, the geometry of the stenosis, the aortic pressure, the density of the contrast agent as observed in the angiogram images, the hyperemic flow, and the density and viscosity of blood. For some applications, such parameters are derived using one or more of the following techniques:

For some applications, the geometric model of the stenosis is obtained by extrapolating lumen measurement data from QCA. For some applications, the geometry of the lumen is determined, typically online and typically in response to a single user click, at the area of the stenosis, e.g., by performing QCA. As described hereinabove, QCA may be performed using images that were acquired from two or more viewing angles.

For some applications, densitometry is used to determine or to enhance the accuracy of the geometric model of the stenosis. For some applications, geometry-indication-receiving functionality 14 determines the cross-sectional area of the lumen in the vicinity of the stenosis, and/or at other locations along the lumen (e.g., within a healthy portion of the lumen) by performing densitometry on at least one of the angiographic images, in accordance with the techniques described hereinbelow. For some applications, densitometry is obtained, typically automatically, by comparing the density of the contrast agent in a healthy section of the lumen (e.g., the section proximal to the stenosis) to its density in other parts of the lumen (e.g., in the vicinity of the stenosis, or downstream of the stenosis). For some applications, such a comparison is made on an angiogram image after background subtraction is applied to the angiogram image. For some applications background subtraction is performed by subtracting images acquired before the contrast injection from images acquired after the contrast injection. For some applications, the images acquired before the contrast injection and the images acquired after the contrast injection are gated to the same phase in the cardiac cycle. For some applications, the images acquired before the contrast injection and the images acquired after the contrast injection are gated to the end-diastolic phase.

For some applications, the hyperemic flow is calculated by digital subtraction angiography, for example, using techniques that are similar to those described in one or more of the following references, which are incorporated herein by reference:

Molloi, S., Ersahin, A., Tang, J., Hicks, J. & Leung, C. Y., 1996 "Quantification of volumetric coronary blood flow with dual-energy digital subtraction angiography," Circulation 93, 1919-1927;

Molloi, S., Zhou, Y. & Kassab, G. S. 2004 "Regional volumetric coronary blood flow measurement by digital angiography: in vivo validation," Acad. Radiol. 11, 757-766;

Sabee Molloi, David Chalyan, Huy Le and Jerry T. Wong, 2012, "Estimation of coronary artery hyperemic blood flow based on arterial lumen volume using angiographic images," The International Journal Of Cardiovascular Imaging, Volume 28, Number 1, 1-11; and Molloi S, Bednarz G, Tang J, Zhou Y, Mathur T (1998), "Absolute volumetric coronary blood flow measurement with digital subtraction angiography," Int J Card Imaging 14:137-145

For some applications, the hyperemic flow is calculated by performing digital subtraction on images of the stenosis or lumens, which have been stabilized via image tracking, with or without warping of the lumens in the images, e.g., using techniques described hereinabove. For some applications, flow is determined in accordance with techniques described in US 2008/0221442 to Tolkowsky, which is incorporated herein by reference. For example, on-line geometric and/or hemodynamic measurements (e.g., size, flow, ejection fraction) may be made and/or displayed upon the stabilized images, e.g., as described with reference to FIG. 4. Alternatively or additionally, a stabilized image stream may be used for on-line measurement of the flow within a lumen, e.g., by measuring the time it takes a presence of contrast agent (e.g., a bolus of contrast agent, a given concentration of contrast agent, and/or a pattern of contrast agent) to travel a known distance, in accordance with the techniques described hereinabove.

For some applications, the hyperemic flow is calculated by multiplying blood velocity by the lumen cross-sectional area, the blood velocity and the lumen cross-sectional area typically having been determined automatically by processor 10.

For some applications, the blood velocity is calculated from angiogram images by comparing density curves, for example, as described hereinabove with reference to FIGS. 3A-B, and/or as described in ten Brinke, which is incorporated herein by reference.

For some applications, the blood velocity is calculated from angiogram images by using contrast flow maps, e.g., using techniques that are similar to those described in ten Brinke, which is incorporated herein by reference.

For some applications, the cross-sectional area is calculated from QCA measurements of the artery and/or densitometry.

For some applications, the density and viscosity of blood is determined, for example, using techniques that are similar to those described in one or more of the following references, which are incorporated herein by reference:

Gerald E. Miller, "Fundamentals of Biomedical Transport Processes, Morgan & Claypool Publishers," chapter 2; and Buddy D. Ratner, "Biomaterials Science: An Introduction to Materials in Medicine," Elsevier, chapter 7.

As described hereinabove, typically, parameters relating to the geometry of the lumen, and/or flow within the lumen are determined from angiographic images of the lumen. For some applications, a luminal-flow-related index (e.g., FFR) is calculated, in whole or in part, using a model which was previously created by means of a machine learning classifier (e.g., Support Vector Machine, Neural Network, etc.). Typically, in order to train the machine learning classifier, FFR or a similar luminal-flow-related index of a blood vessel is measured using conventional methods (e.g., using a pressure wire, and/or an alternative technique). Additionally, angiographic images of the blood vessel are acquired, and are analyzed such as to determine parameters such as lumen dimensions, blood velocity, blood flow, haziness, heart muscle flush, time of contrast dissipation, densitometry, QCA, distance from an ostium, number of bifurcations between an ostium and a lesion, and/or anatomical locations (e.g., distal left anterior descending artery, proximal right coronary artery, 5 mm along the circumflex branch, etc.). Feature vectors consisting of some, or all of, the above mentioned parameters are derived from the angiograms. Multiple sets of the aforementioned vectors, together with the corresponding measured FFR, and/or other measured luminal-flow-related indices, are provided as inputs to the machine learning classifier. For some applications, the aforementioned FFR and/or other luminal-flow-related index is quantized, such as to allow multiclass classification for each discrete level of FFR and/or other luminal-flow-related index. For some applications, a machine learning algorithm which allows a continuous result function (e.g. a machine learning regression algorithm) is used to train a machine learning classifier using the FFR or other luminal-flowrelated index inputted into the algorithm as is, i.e., without the FFR or the other luminal-flow-related index being quantized.

After training the aforementioned machine learning classifier, a subject's FFR and/or other luminal-flow-related input parameter is derived, using the machine learning classifier, using an angiogram of a lumen of the subject. At least some of the parameters that are automatically derived from an angiogram of a lumen of the subject are provided as inputs to the machine learning classifier. Based on the training of the machine learning classifier, the classifier uses the parameters that are inputted to the classifier to predict FFR or another luminal-flow-related index. Typically, the classifier predicts FFR or another luminal-flow-related index, by determining one or more feature vectors of the blood vessel based upon the inputted parameters, and by utilizing the data collected and processed by the classifier during the aforementioned training phase to determine the luminal-flow-related index based upon the feature vector(s).

For some applications, the value of the current flow-related parameter at a location within a lumen is determined using a machine-learning classifier, based upon at least the determined blood velocity and the geometry of the lumen at the location. For some applications, the value of the luminal-flow-related index is determined by determining the relationship between the value of a current flow-related parameter and the value of a second flow-related parameter, using a machine-learning classifier.

For some applications of the current invention, a luminal-flow-related index (e.g., FFR) is deduced, using patient history as an input, in accordance with the following technique.

FFR is defined as the ratio between stenotic flow $Q_S$ and normal flow $Q_N$ under hyperemic conditions: FFR=$Q_S/Q_N$.

For some applications, patient history data (typically, data obtained using a cine angiogram injection post treatment of a stenosis) are analyzed in order to determine the subject's normal flow through the lumen (i.e., the subject's flow through the lumen, when the subject was healthy). For example, the subject's normal flow may be determined by analyzing a historical angiographic image sequence of the subject, using the techniques described hereinabove. The subject's stenotic flow through the lumen is determined by analyzing an angiographic sequence acquired while the subject had the stenosis (e.g., a current angiographic image sequence), in accordance with the techniques described hereinabove. A luminal-flow-related index (e.g., FFR), is determined by comparing to each other the normal and the stenotic flows.

For some applications, the coronary flow is calculated by applying densitometry to digital subtraction angiography images, for example, using techniques described in one or more of the following references, which are incorporated herein by reference:

Molloi, S., Ersahin, A., Tang, J., Hicks, J. & Leung, C. Y., 1996 "Quantification of volumetric coronary blood flow with dual-energy digital subtraction angiography," Circulation 93, 1919-1927;

Molloi, S., Zhou, Y. & Kassab, G. S. 2004 "Regional volumetric coronary blood flow measurement by digital angiography: in vivo validation," Acad. Radiol. 11, 757-766;

Sabee Molloi, David Chalyan, Huy Le and Jerry T. Wong, 2012, "Estimation of coronary artery hyperemic blood flow based on arterial lumen volume using angiographic images," The International Journal Of Cardiovascular Imaging, Volume 28, Number 1, 1-11; and Molloi S, Bednarz G, Tang J, Zhou Y, Mathur T (1998), "Absolute volumetric coronary blood flow measurement with digital subtraction angiography," Int J Card Imaging 14:137-145.

For some applications, the coronary flow is calculated by performing digital subtraction on images of the stenosis or lumens, which have been stabilized via image tracking, with or without warping of the lumens in the images, e.g., using techniques described hereinabove. For some applications, flow is determined in accordance with techniques described in US 2008/0221442 to Tolkowsky, which is incorporated herein by reference. For example, on-line geometric and/or hemodynamic measurements (e.g., size, flow, ejection fraction) may be made and/or displayed upon the stabilized images, e.g., as described with reference to FIG. 4. Alternatively or additionally, a stabilized image stream may be used for on-line measurement of the flow within a lumen, e.g., by measuring the time it takes a presence of contrast agent (e.g., a bolus of contrast agent, a given concentration of contrast agent, and/or a pattern of contrast agent) to travel a known distance, in accordance with the techniques described hereinabove.

For some applications of the current invention, a luminal-flow-related index (e.g., FFR) is deduced, using patient history as an input, in accordance with the following technique.

FFR is defined as the ratio of stenotic flow $Q_S$ and normal flow $Q_N$. In turn, the flow can be written as the product of mean velocity and volume, divided by length L, of a lumen segment.

$$FFR=(Q_S/Q_N)=((\text{VELOCITY}_S)(\text{VOLUME}_S)/L)/((\text{VELOCITY}_N)(\text{VOLUME}_N)/L)$$

For some applications, patient history data (typically, data obtained using a cine angiogram injection post treatment of a stenosis), are analyzed in order to determine the subject's normal blood velocity within the lumen (i.e., the subject's blood velocity within the lumen, when the subject was healthy). For example, the subject's normal blood velocity may be determined by analyzing a historical angiographic image sequence, using the techniques described hereinabove. The subject's stenotic blood velocity is determined by analyzing an angiographic sequence acquired while the subject had the stenosis (e.g., a current angiographic image sequence), in accordance with the techniques described hereinabove. This provides both normal and stenotic blood velocities, thus facilitating the calculation of the FFR.

The FFR is typically determined by identifying a segment of the lumen that is currently healthy (even though the lumen currently contains a stenosis in a different segment thereof). A ratio is determined between the blood velocity in the segment of the lumen at the time of the acquisition of the historical angiographic image sequence (when the whole lumen was healthy), and blood velocity in a healthy segment of the stenotic lumen at the time of the acquisition of the current angiographic sequence. Assuming that the volume of the segment of the lumen being analyzed is substantially unchanged between the time of the acquisition of the historical angiographic image sequence and the time of the acquisition of the current angiographic sequence, the ratio of flows is equal to the ratio of the velocities in this segment. Thus:

$$FFR=(Q_S/Q_N)=\text{VELOCITY}_S/\text{VELOCITY}_N$$

For some applications, the blood velocity is calculated from angiogram images by comparing density curves, for example, as described hereinabove with reference to FIGS. 3A-B, and/or as described in ten Brinke, which is incorporated herein by reference.

For some applications, the blood velocity is calculated from angiogram images by using contrast flow maps, for example, using techniques as described in ten Brinke, which is incorporated herein by reference.

Figure 5:
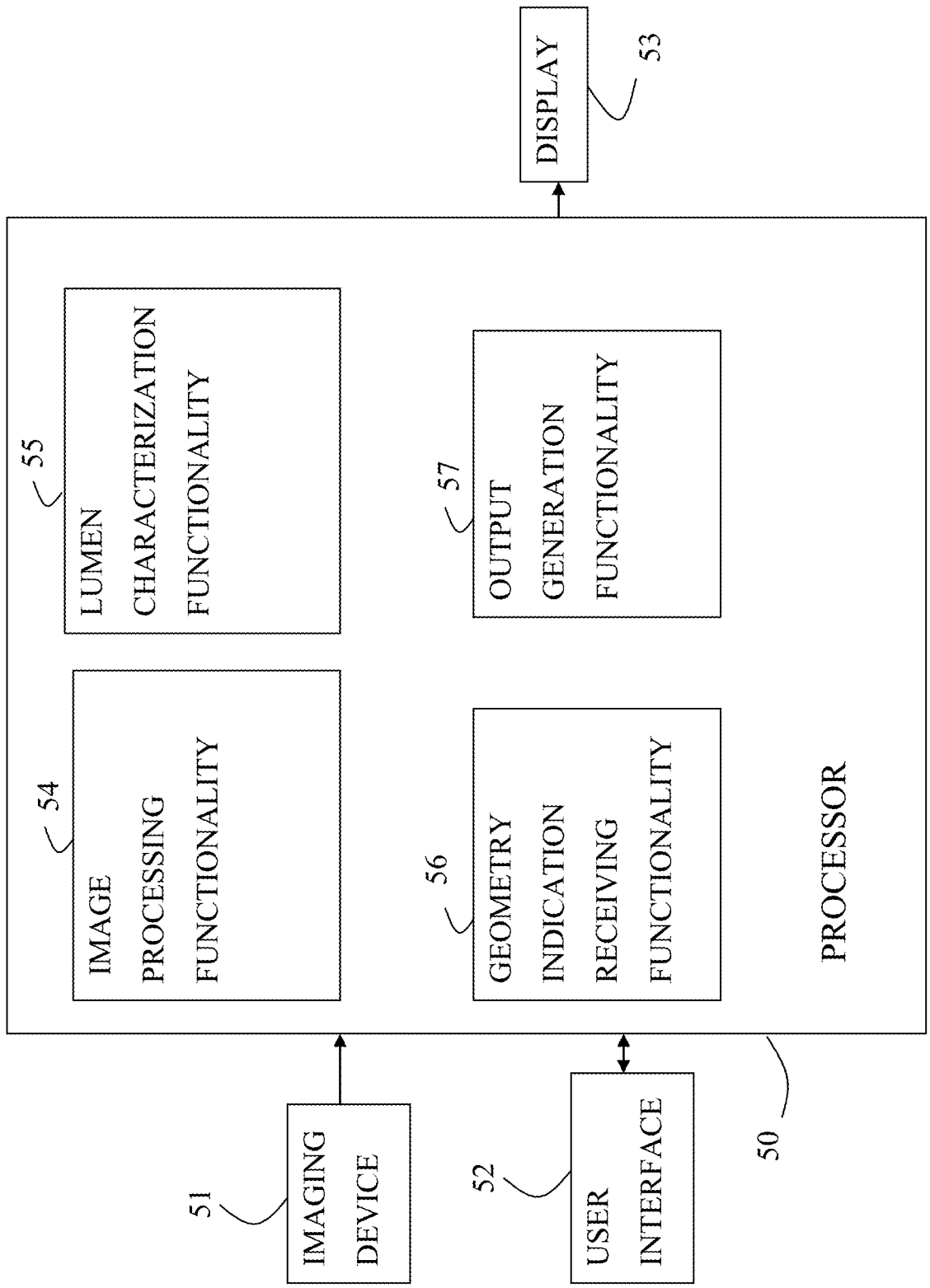
FIG. 5 is a schematic illustration of a processor that is used to determine a characteristic of a lumen by means of image processing, in accordance with some applications of the present invention.

Reference is now made to FIG. 5, which is a schematic illustration of a processor 50 that is used to determine a characteristic of a lumen by means of image processing, in accordance with some applications of the present invention. Typically the processor determines the characteristic of the lumen based upon image processing of angiographic images of the lumen that are acquired by an imaging device 51. Processor 50 typically receives inputs via the imaging device and via a user interface 52, and generates an output on display 53. The imaging device, the user interface, and the display are generally similar to those described with reference to FIG. 1. For some applications, functionalities described with reference to processor 50 are performed in conjunction with functionalities performed with one or more of the other processors described herein.

For some applications of the present invention, image-processing functionality 54 of processor 50 analyzes temporal changes in a density of a contrast agent at a given location within the lumen, within an angiographic sequence of the lumen. In response to the analysis, lumen-characterization functionality 55 determines a characteristic of the lumen at the location. For example, contrast agent may be administered to the lumen in accordance with a protocol. For example, as described hereinabove, an automated injection device may be programmed to inject pulses of contrast agent in a predetermined pattern, e.g., in a pattern having a given time-density curve. For some applications, the processor compares (a) the temporal changes in the density of the contrast agent at the location within the lumen to (b) the protocol in accordance with which the contrast agent was administered. The processor determines a characteristic of the lumen at the location in response to the comparison. For example, in response to seeing that there is a build-up of contrast agent at the location, the processor may determine that there is a stenosis in the vicinity of the location, e.g., at the location, upstream of the location, and/or downstream of the location. For some applications, based upon temporal changes in the density of a contrast agent at the given location, the lumen-characterization functionality determines a luminal-flow-related index (e.g., FFR) of the lumen at the location. For some applications, the lumen-characterization functionality determines the characteristic of the lumen, based upon the temporal changes in the density of the contrast agent, using a machine learning classifier. For some applications, the processor includes geometry-indication-receiving functionality 56, which is configured to determine the geometry of the lumen at the location in a generally similar manner to that described with respect to the geometry-indication-receiving functionality described with reference to FIG. 1. The luminal-flow-related index is determined at least partially based upon the geometry of the lumen at the location. Output-generation functionality 57 generates an output on the display in response to the determined characteristic of the lumen.

Calculating Flow Velocities from Angiograms and Using the Flow Velocities to Calculate a CFR Measure Coronary flow reserve (CFR) is defined as the ratio between hyperemic blood velocity and resting blood velocity. For some applications, a first angiogram is acquired under hyperemic conditions, and a second angiogram is acquired under resting conditions. The velocity of blood flow in the selected lumen is automatically determined in the first and second angiogram images (e.g., using techniques described hereinabove), and the determined velocities are used to calculate the CFR.

For some applications, the blood velocity is calculated from angiogram images by comparing density curves, for example, as described hereinabove with reference to FIGS. 3A-B, and/or as described in ten Brinke, which is incorporated herein by reference.

For some applications, the blood velocity is calculated from angiogram images by using contrast flow maps, for example, as described in ten Brinke, which is incorporated herein by reference.

Figure 6:
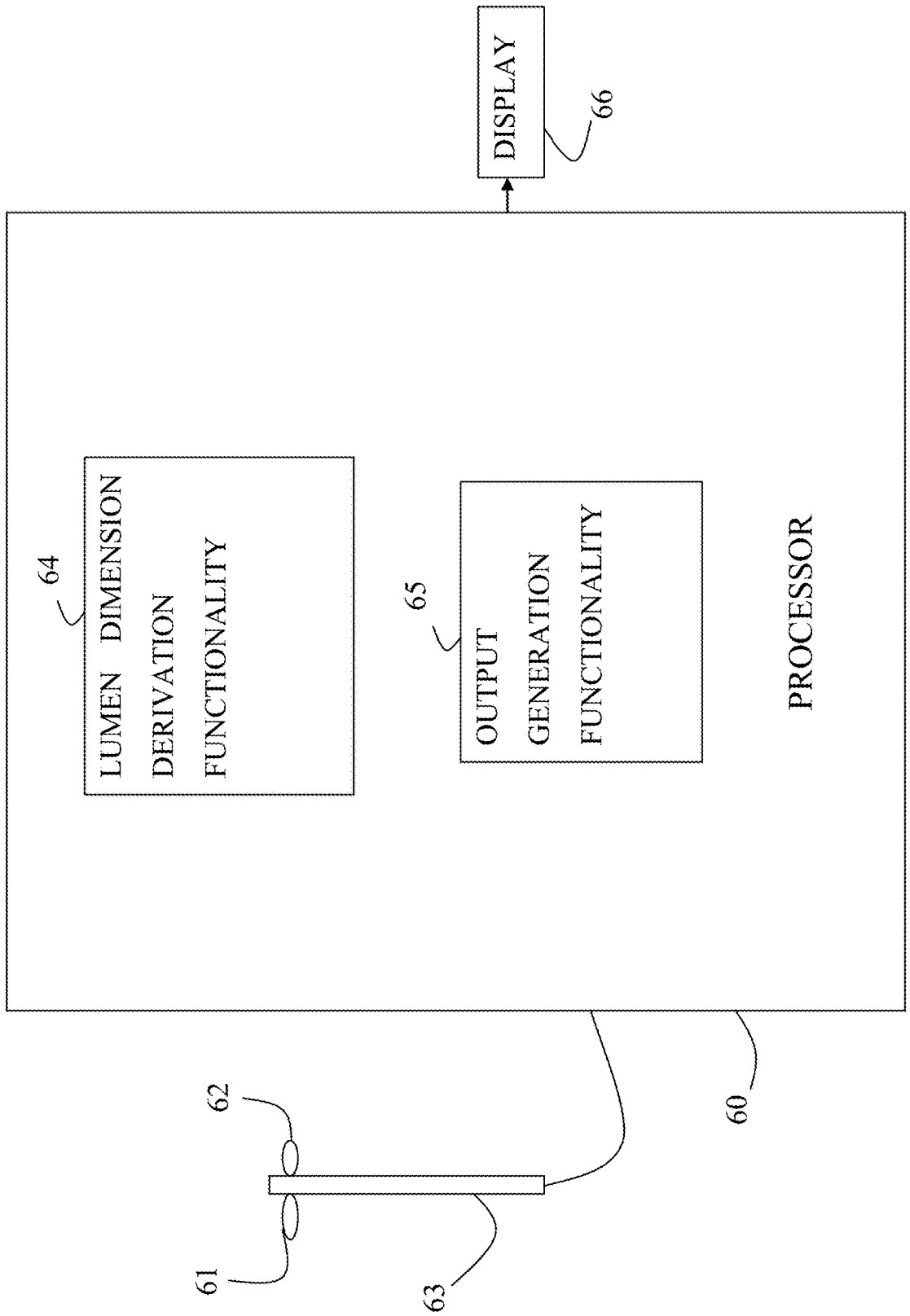
FIG. 6 is a schematic illustration of a processor that is used to calculate lumen dimensions and/or lumen geometry using blood velocity and pressure measurements, in accordance with some applications of the present invention.

Calculating Lumen Dimensions and Geometry (QCA) from Actual Velocity/Pressure Readings Reference is now made to FIG. 6, which is a schematic illustration of a processor 60 that is used to calculate lumen dimensions and/or lumen geometry based upon blood velocity and pressure measurement, in accordance with some applications of the present invention. Typically, the processor calculates lumen dimensions based upon (a) pressure within the lumen measured by a pressure sensor 61, and (b) blood velocity within the lumen, measured by a blood velocity sensor 62. For some applications, the pressure sensor and blood velocity sensor are coupled to a tool 63 that is configured to be inserted into the lumen. For some applications, functionalities described with reference to processor 60 are performed in conjunction with functionalities performed with one or more of the other processors described herein. Lumen-dimension-derivation functionality 64 of the processor derives a dimension of the lumen from the measured pressure and blood velocity. Output-generation functionality 65 generates an output on a display 66 in response to the derived dimension.

For some applications, the blood velocity and pressure readings are gathered simultaneously, for example, using a device that is capable of measuring blood pressure and blood velocity simultaneously in a lumen, while the device is being moved through the lumen (e.g., during pullback of the device through the lumen). For example, the ComboWire® manufactured by Volcano Corp. (San Diego, Calif.) may be used to measure blood pressure and blood velocity simultaneously.

For some applications, the lumen cross-sectional areas and length are automatically calculated by solving computational fluid dynamics equations, which are dependent on the velocity and pressure values along the lumen segment. Alternatively or additionally, a length of a portion of the lumen, a diameter of the lumen, a minimal lumen diameter of the lumen, and/or a percentage occlusion of the lumen is determined.

For some applications, in a circular stenosis the length and cross-sections of the lumen are calculated based upon the following equations:

$$Q = \frac{dP}{dR}$$

$$L = \frac{Q}{8\pi\eta} \int_{t_0}^{t_1} \frac{P' dt}{v^2}$$

$$Q = vA$$

$$dR = \frac{8\eta dL}{\pi r^4}$$

$$A = \frac{Q}{v}$$

where L is the length of at least a portion of a segment of a lumen along which pullback is performed, A is the cross-sectional area along the lumen, v is the blood velocity along the lumen as measured by the device, Q is the blood flow, η is the blood viscosity, P' is the time derivative of the pressure along the lumen as measured by the device, r is the radius of the lumen, and $t_0$ and $t_1$ are the times at which the device is at respective ends of the luminal segment during the pullback.

Co-Registration of Endoluminal Images and Extraluminal Images

Figure 7:
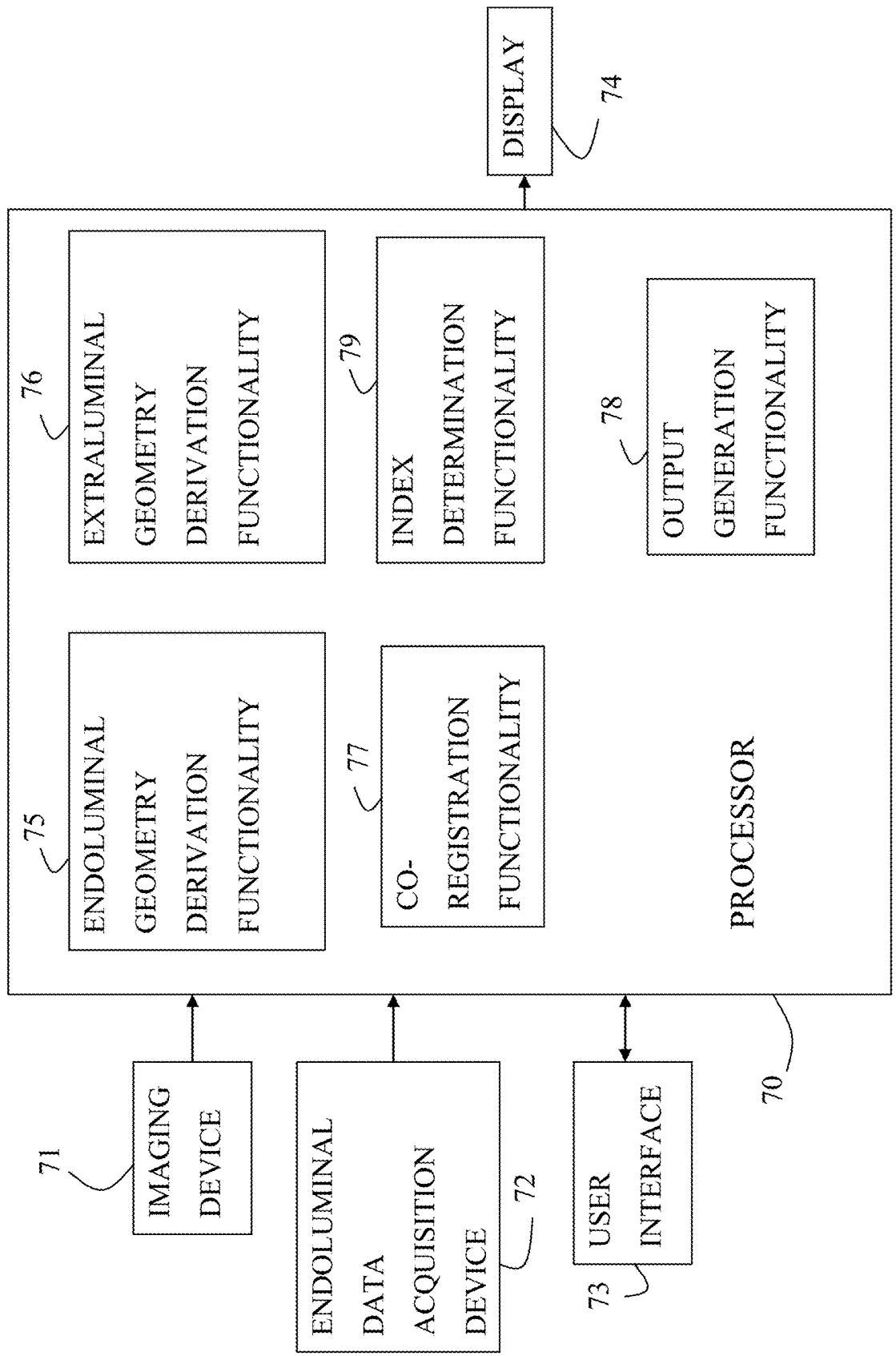
FIG. 7 is a schematic illustration of a processor that is used to co-register endoluminal data points to locations along the lumen within an extraluminal image, in accordance with some applications of the present invention.

Reference is now made to FIG. 7, which is a schematic illustration of a processor 70 that is used to co-register at least some of the endoluminal data points to locations along the lumen within an extraluminal image, in accordance with some applications of the present invention. Processor 70 typically receives inputs via imaging device 71, data-acquisition device 72, and a user interface 73, and generates an output on display 74. Typically, the processor receives extraluminal images of the lumen that are acquired by an extraluminal imaging device 71. Further typically, the processor receives endoluminal data points of the lumen that are acquired by an endoluminal data-acquisition device 72. The extraluminal imaging device, the user interface, and the display are typically generally similar to those described with reference to FIG. 1. For some applications, functionalities described with reference to processor 70 are performed in conjunction with functionalities performed with one or more of the other processors described herein.

Typically, processor 70 includes endoluminal-geometry-derivation-functionality 75, which is configured, for at least some of the endoluminal data points, to derive from the endoluminal data point a value of a geometrical parameter of the lumen (e.g., cross-sectional area of the lumen, and/or a diameter of the lumen) at a location within the lumen at which the endoluminal data point was acquired. Further typically, processor 70 includes extraluminal-geometry-derivation-functionality 76, which is configured to derive values of the geometrical parameter of the lumen (e.g., cross-sectional area of the lumen, and/or a diameter of the lumen) at a plurality of locations along the lumen, by performing image processing on the at least one extraluminal image of the lumen (e.g., using techniques described hereinabove). Co-registration functionality 77 of the processor is configured to co-register at least some of the endoluminal data points to locations along the lumen within the extraluminal image by correlating (a) the values of the geometrical parameters (e.g., a sequence of values of the geometrical parameters) corresponding to the endoluminal data points with (b) the values of the geometrical parameter (e.g., a sequence of values of the geometrical parameters) determined by performing image processing on the at least one extraluminal image. For some applications, the co-registration functionality correlates (a) a variation (e.g., a mathematical derivative) of the values of the geometrical parameter corresponding to a sequence of endoluminal data points with (b) a variation (e.g., a mathematical derivative) of the values of the geometrical parameter corresponding to a sequence of locations within the extraluminal image. Output-generation functionality 78 of the processor generates an output on the display based upon the co-registration (e.g., an output indicating that a given endoluminal data point corresponds to a given location along the lumen).

For some applications, the endoluminal data-acquisition device acquires endoluminal images, and endoluminal-geometry-derivation-functionality 75 derives the value of the geometrical parameter of the lumen at the location within the lumen at which an endoluminal image was acquired by performing image processing on the endoluminal image. Alternatively or additionally, the endoluminal data-acquisition device acquires blood velocity, flow, and/or blood pressure data points, and endoluminal-geometry-derivation-functionality 75 derives the value of the geometrical parameter of the lumen from the blood velocity, flow, and/or blood pressure data points, e.g., using techniques described hereinabove.

For some applications, processor 70 includes index-determination functionality 79 (and/or other functionalities described with reference to FIG. 1), and the processor is configured to determine a luminal-flow-related index of the subject in a non-invasive manner, e.g., using techniques described hereinabove. By performing the co-registration, it is determined that respective endoluminal data points correspond to respective values of the luminal flow-related index. The output-generation functionality generates an output on the display based upon determining that respective endoluminal data points correspond to respective values of the luminal flow-related index (e.g., by generating an output indicating that a given endoluminal data point corresponds to a given value of the luminal flow-related index).

For some applications, the endoluminal data-acquisition device, while being moved through the lumen, acquires endoluminal data points (e.g., endoluminal images (such as IVUS images or OCT images), or functional endoluminal data points) in addition to acquiring blood velocity data (e.g., using a velocity sensor that is coupled to the endoluminal data-acquisition device). Typically, the endoluminal data acquisition device, while being moved through the lumen, acquires a set of the endoluminal data points, and a set of blood velocity data points, the blood velocity data points being indicative of the blood velocity within the lumen (and therefore being indicative of the cross-sectional area of the lumen) at respective locations within the lumen. For some applications, the blood velocity data points from the endoluminal imaging device pullback are used to co-register the endoluminal data points to respective locations along the lumen within an extraluminal image (such as an angiogram) of the lumen. For example, the following technique may be used:

It is assumed that flow in the lumen is constant and that the blood velocity within the lumen is therefore inversely proportional to the cross-section of the lumen. Cross-sectional areas of the lumen at respective locations along the lumen are determined, by performing image processing on the extraluminal image of the lumen, e.g., by automatically performing QCA on the extraluminal image, and/or by performing densitometry on the extraluminal image. The blood velocity data points acquired by the endoluminal data-acquisition device are correlated with the cross-sectional areas determined from the extraluminal image, such as to determine locations within the extraluminal image that correspond to the location of the endoluminal imaging device at the time of the acquisition of respective endoluminal images by the endoluminal imaging device.

For example, the pullback of the endoluminal imaging device may commence when the endoluminal imaging device is at a known location with respect to the lumen within the extraluminal image. It may be determined, based upon the blood velocity data, that when the $n^{th}$ endoluminal image was acquired, the cross-section of the lumen at the location of the endoluminal imaging device was 50 percent of the cross-section of the lumen at the location of the endoluminal imaging device within the lumen when pullback commenced. The extraluminal image may then be analyzed to determine the location within the extraluminal image at which the cross-section of the lumen is 50 percent of the cross-section of the lumen at the location of the endoluminal imaging device when pullback commenced. Based upon this analysis, the processor determines the location within the extraluminal image that corresponds to the $n^{th}$ endoluminal image. In general, the co-registration functionality determines that a blood velocity data point acquired in temporal proximity to a given endoluminal data point is associated with a given location along the lumen. In response thereto, the co-registration functionality determines that the given endoluminal data point is associated with the given location along the lumen.

For some applications, techniques described in US 2012/0004537 and/or in International Patent Application PCT/IL2013/050438 (published as WO 13/175472), both of which application are incorporated herein by reference, are used in conjunction with the above-described co-registration technique. Typically, an output is generated in response to the co-registration. For some applications, the endoluminal data points include endoluminal images, and, based upon the co-registration, the endoluminal images are arranged in an image stack. Typically, the endoluminal image stack is generated by extracting endoluminal images at locations along the lumen. From each image, a cross section of the image (typically, one line of pixels) is extracted and placed in the stack at a location corresponding to the determined location of the endoluminal image along the lumen. Thus, the images are positioned at locations within the stack corresponding to relative locations along the lumen at which the images were acquired. For some applications, the endoluminal data points are functional endoluminal data points, and a display of the endoluminal data points is generated, in which the endoluminal data points are positioned at locations corresponding to relative locations within the lumen at which the endoluminal data points were acquired. Typically, the functional endoluminal data points are displayed in the stack by displaying a stack of indications of the functional endoluminal data points, locations of the indications within the stack corresponding to relative locations within the lumen at which the endoluminal data points were acquired. For example, numerical indications of the functional endoluminal data points may be displayed and/or representations of the functional endoluminal data points (which may be based upon a color legend, for example) may be displayed. For some applications, indications of non-functional endoluminal data points are displayed in the described manner.

For some applications, while observing an extraluminal image of the lumen, one or more locations along the lumen are indicated by a user. In response thereto, based upon the co-registration, previously-acquired endoluminal data points (e.g., images) corresponding to the one or more locations are displayed. For some applications, user interface 73 is used to select the one or more locations. Typically, the user designates a location using the user interface, and, in response thereto, typically automatically and on-line, the system identifies a location along the lumen as corresponding to the designated location, and retrieves and displays a corresponding endoluminal data point (e.g., image).

For some applications, data acquired by a first endoluminal modality (e.g., IVUS) are co-registered with the extraluminal image, e.g., in accordance with the techniques described hereinabove. Subsequently, data acquired by a second endoluminal modality (e.g., OCT) are co-registered with the extraluminal image, e.g., in accordance with the techniques described hereinabove. Consequently, due to both data sets being co-registered with the extraluminal image, the two data sets are co-registered to one another. For some applications, the two endoluminal data sets are displayed overlaid or otherwise merged with one another.

For some applications, movement (e.g., pullback) of the endoluminal data-acquisition device is performed in the course of a continuous injection of contrast agent performed under fluoroscopic imaging. For example, the endoluminal data-acquisition device may be an OCT probe, which typically requires concurrent flushing of the lumen during image acquisition, in order to remove blood from the lumen, since the blood interferes with the OCT imaging. Therefore, typically, during endoluminal imaging with an OCT probe, contrast agent is continuously injected into the lumen. As described hereinabove, typically, extraluminal images of the lumen are acquired in the presence of contrast agent, in order to determine the cross-sectional area of the lumen (e.g., by performing QCA and/or densitometry on the extraluminal images). For some applications, a single injection of contrast agent is used (a) to facilitate the acquisition of a set of endoluminal data points, and (b) to facilitate determination of the cross-sectional area of the lumen. For some applications, based upon the determined cross-sectional area of the lumen, the endoluminal data points are co-registered to the extraluminal image, e.g., using the techniques described hereinabove.

In general, the scope of the present invention includes non-invasively determining a value of a luminal-flow-related index of the subject at a plurality of locations along the lumen, at least partially by performing image processing on the two-dimensional angiographic images, in accordance with the techniques described herein, and co-registering the luminal-flow-related index at the locations to a set of endoluminal data points (e.g., endoluminal images, or endoluminal functional data points). Typically, while an endoluminal data-acquisition device is being moved through the lumen, the device acquires a set of endoluminal data points of the lumen at a plurality of locations within the lumen. Co-registration functionality 77 of the processor determines that respective endoluminal data points correspond to respective locations along the lumen, for example using techniques described in US 2012/0004537 and/or in International Patent Application PCT/IL2013/050438 (published as WO 13/175472), both of which application are incorporated herein by reference. Thus, the co-registration functionality determines that respective endoluminal data points correspond to respective values of the luminal flow-related index. Typically, an output is generated in response to the aforementioned co-registration. For example, an endoluminal image frame may be displayed together with an indication of the value of the luminal-flow-related index at the location along the lumen at which the endoluminal image was acquired.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. Apparatus comprising:
    an image-acquisition device configured to acquire a plurality of angiographic image frames of a lumen of a subject; and at least one processor configured:
to control the image-acquisition device to acquire the plurality of angiographic image frames of the lumen of the subject,
to determine an angiographic image-based fractional flow reserve (FFR) value at a given location within the lumen, wherein the angiographic image-based FFR value is determined based only on image processing of the plurality of angiographic image frames,
to compare the first angiographic image-based FFR value to a first threshold value and a second threshold value,
to drive a display in communication with the processor to provide a visual indication of a treatment for the lumen of the subject, in response to the angiographic image-based FFR value passing the first threshold value, and
to drive the display, in response to the angiographic image-based FFR value passing the second threshold value but not passing the first threshold value, to provide a visual indication that an intraluminal FFR value be determined in a further procedure using a modality different than the image-acquisition device, wherein the further procedure comprises obtaining intraluminal measurements using a sensor that is inserted into the lumen.

2. The apparatus according to claim 1, wherein the processor is configured to determine the angiographic image-based FFR value by:
determining geometry of the lumen at the given location, by analyzing the plurality of angiographic image frames,
determining a time it takes a contrast agent to travel a known distance through the lumen, by analyzing the plurality of angiographic image frames, and
determining a value of a current flow-related parameter of the lumen based upon the time it takes the contrast agent to travel the known distance through the lumen and the determined geometry of the lumen.

3. The apparatus according to claim 2, wherein:
the processor is further configured to receive an indication of a value of a second flow-related parameter of the subject; and
the processor is configured to determine the angiographic image-based FFR value by determining a relationship between the value of the current flow-related parameter and the value of the second flow-related parameter.

4. The apparatus according to claim 3, wherein the processor is configured to determine the angiographic image-based FFR value based upon a determined blood velocity and geometry of the lumen at the location, using a machine-learning classifier.

5. The apparatus according to claim 3, wherein the processor is configured to determine the relationship between the value of the current flow-related parameter and the value of the second flow-related parameter using a machine-learning classifier.

6. The apparatus according to claim 3, wherein the indication of the value of the second flow-related parameter of the subject is based on a historic angiographic image sequence obtained when the lumen was healthy.

7. The apparatus according to claim 1, wherein the given location includes a location in a vicinity of a stenosis within the lumen, and wherein the processor is configured to determine the angiographic image-based FFR value by determining the angiographic image-based FFR value in the vicinity of the stenosis.

8. The apparatus according to claim 1, wherein the processor is configured to determine a value of instantaneous wave-free ratio of the subject at the location based on the plurality of angiographic image frames.

9. The apparatus according to claim 1, wherein the processor is configured to:
generate a stabilized image stream, by:
identifying at least a portion of the lumen in the plurality of angiographic image frames, and
aligning the plurality of angiographic image frames with respect to one another such that the portion of the lumen in each of the plurality of angiographic image frames is aligned with the portion of the lumen in the other angiographic image frames of the plurality of angiographic image frames, and
generate, at a location that corresponds to the location and that is within the stabilized image stream, an indication of the angiographic image-based FFR value at the location.

10. The apparatus according to claim 1, wherein the processor is configured to generate an indication of the angiographic image-based FFR value using a color legend, on an image of the lumen.

11. The apparatus according to claim 1, wherein the processor is configured to determine the angiographic image-based FFR value by:
performing a quantitative coronary angiography (QCA) measurement on at least one image frame of the plurality of angiographic image frames to determine a cross-sectional area of the lumen at the given location;
tracking flow of a contrast agent to travel a known distance through the lumen; and
determine a value of a current flow-related parameter of the lumen based upon an amount of time it takes the contrast agent to travel the known distance through the lumen and the determined cross-sectional area of the lumen; and
determine the first FFR value based on the value of the current flow-related parameter of the lumen.

12. A method for use with a plurality of angiographic image frames of a lumen of a subject, the method comprising:
acquiring the plurality of angiographic image frames of a lumen of a subject, using an image-acquisition device; and
using at least one processor:
controlling, by the at least one processor, the image-acquisition device to acquire the plurality of angiographic image frames of the lumen of the subject;
determining an angiographic image-based fractional flow reserve (FFR) value at a given location within the lumen, based only on image processing of the plurality of angiographic image frames;
comparing the angiographic image-based FFR value to a first threshold value and a second threshold value,
driving a display in communication with the processor to provide a visual indication of a treatment for the lumen of the subject, in response to the angiographic image-based FFR value passing the first threshold value; and
driving the display, in response to the angiographic image-based FFR value passing the second threshold value but not passing the first threshold value, to provide a visual indication that an intraluminal FFR value be determined in a further procedure using a modality different than the image-acquisition device, wherein the further procedure comprises obtaining intraluminal measurements using a sensor that is inserted into the lumen.

13. The method according to claim 12, wherein determining the first angiographic image-based FFR value comprises:
determining geometry of the lumen at the given location within the lumen, by analyzing the plurality of angiographic image frames,
determining a time it takes a contrast agent to travel a known distance through the lumen, by analyzing the plurality of angiographic image frames, and
determining a value of a current flow-related parameter of the lumen based upon the time it takes the contrast agent to travel the known distance through the lumen and the determined geometry of the lumen.

14. The method according to claim 13, further comprising, using the processor receiving an indication of a value of a second flow-related parameter of the subject, wherein determining the value of the angiographic image-based FFR value of the subject at the given location within the lumen comprises determining a relationship between the value of the current flow-related parameter and the value of the second flow-related parameter.

15. The method according to claim 14, wherein determining the value of the current flow-related parameter at the location within the lumen comprises, using a machine-learning classifier, determining the value of the current flow-related parameter at the location within the lumen, based upon a determined blood velocity and geometry of the lumen at the location.

16. The method according to claim 14, wherein determining the relationship between the value of the current flow-related parameter and the value of the second flow-related parameter comprises determining the relationship between the value of the current flow-related parameter and the value of the second flow-related parameter using a machine-learning classifier.

17. The method according to claim 12, wherein the given location includes a location in a vicinity of a stenosis within the lumen, and wherein determining the angiographic image-based FFR value comprises determining the angiographic image-based FFR value in the vicinity of the stenosis.

18. The method according to claim 12, further comprising determining a value of instantaneous wave-free ratio of the subject at the location.

19. The method according to claim 12, further comprising:
generating a stabilized image stream, by:
identifying at least a portion of the lumen in the plurality of angiographic image frames, and
aligning the plurality of angiographic image frames with respect to one another such that the portion of the lumen in each of the plurality of angiographic image frames is aligned with the portion of the lumen in the other angiographic image frames in the plurality of angiographic image frames; and
generating an indication of the angiographic image-based FFR value on the stabilized image stream.

20. The method according to claim 12, further comprising generating, on an image of the lumen, an indication of the angiographic image-based FFR value using a color legend.

21. Apparatus comprising:
an image-acquisition device configured to acquire a plurality of angiographic image frames of a lumen of a subject; and
at least one processor configured:
to control the image-acquisition device to acquire the plurality of angiographic image frames of the lumen of the subject;
to determine an angiographic image-based fractional flow reserve (FFR) value at a given location within the lumen, wherein the angiographic image-based FFR value is calculated based only on image processing of angiographic image frames,
to compare the angiographic image-based FFR value to a first threshold value and a second threshold value, and
to drive a display in communication with the processor, in response to the angiographic image-based FFR value passing the second threshold value but not passing the first threshold value, to provide a visual indication that an intraluminal FFR value be determined in a further procedure using a modality different than the image-acquisition device, wherein the further procedure comprises obtaining intraluminal measurements using a sensor that is inserted into the lumen.

* * * * *